(12) United States Patent
Kutchan et al.

(10) Patent No.: US 7,037,674 B1
(45) Date of Patent: May 2, 2006

(54) CYTOCHROME P450 REDUCTASES FROM POPPY PLANTS

(75) Inventors: Toni M. Kutchan, Halle (DE);
Meinhart H. Zenk, Halle (DE); David G. Atkins, New York, NY (US);
Anthony J. Fist, Norwood (AU)

(73) Assignee: Johnson & Johnson Research PTY Limited, Strawberry Hill (AU)

( * ) Notice: Subject to any disclaimer, the term of this patent is extended or adjusted under 35 U.S.C. 154(b) by 0 days.

(21) Appl. No.: 09/486,757

(22) PCT Filed: Aug. 28, 1998

(86) PCT No.: PCT/AU98/00705

§ 371 (c)(1),
(2), (4) Date: Jul. 3, 2000

(87) PCT Pub. No.: WO99/11765

PCT Pub. Date: Mar. 11, 1999

(30) Foreign Application Priority Data

Aug. 29, 1997 (AU) .................................. PO8872

(51) Int. Cl.
C12P 21/06 (2006.01)
C12N 15/82 (2006.01)
C12Q 1/68 (2006.01)
C07H 21/02 (2006.01)
C07H 21/04 (2006.01)

(52) U.S. Cl. .................. 435/69.1; 435/6; 435/91.1; 435/468; 530/200; 536/23.1; 536/23.2; 536/23.6; 935/60; 935/61

(58) Field of Classification Search ............. 435/6, 435/69.1, 468, 183, 91.1; 530/200, 228, 530/300, 350, 370; 935/35, 60, 61; 536/23.1, 536/23.6, 23.2
See application file for complete search history.

(56) References Cited

U.S. PATENT DOCUMENTS 6,376,221 B1 * 4/2002 Fist et al. .................. 435/118

FOREIGN PATENT DOCUMENTS

WO     WO 93/21326 A2    10/1993

OTHER PUBLICATIONS

Rosco, A. et al., Archives of Biochem. and Biophysics, vol. 348, No. 2, pp. 369-377 (1997).*
EMBL Seq ID:G 2580496, Nov. 6, 1997, A Rosco et al, 'Cloning and heterologous expressionof cytochrome P-450 reductases from the Papaveraceae (opium poppy)'.
EMBL Seq ID:G 2580497, Nov. 12, 1997, A Rosco et al, NADPH-ferrihemoprotein oxidoreductase from PAPaver somniferum (opium poppy).
EMBL Seq ID:G2580498, Nov. 5, 1997, A Rosco et al, 'Cloning and heterologous expression of cytochrome P-450 reductases of the Papaveraceae(California poppy)'.

(Continued)

Primary Examiner—Jane Zara

(57) ABSTRACT

The present invention relates to production of alkaloids from poppy plants and in particular togenes encoding enzymes in the alkaloid pathway, to proteins encoded by the gens, to plants transformed or transfected with the genes and to methods of altering alkaloid content or blend of poppy plants.

6 Claims, 20 Drawing Sheets

OTHER PUBLICATIONS

EMBL Seq ID:G2580499 Nov. 12, 1997, A. Rosco et al, ferrohemoprotein oxidoreductase from Exchscholzia california poppy).

Proc Natl Acad sci USA, vol. 90, 1993, M S Shet et al, Purification, characterization and cDNA cloning of an NADPH-cytochrome P-450 reductase from *Vigna radiata* (mung bean), pp. 2890-2894 see entire document.

EMBL Seq ID: G400532, Nov. 1, 1996, I Benveniste et al, 'NADPH-ferrihemoprotein reductase from *Vicia sativa* (Spring vetch)'.

EMBL Seq ID:G16189, Nov. 1, 1996, C Mignote-Vieux et al, NADPH-ferrihemoprotein reductase from *Arabidopsis thaliana*(mouse ear cress).

Plant Journal, vol. 4, No.: 1, 1993, A H Meijer et al, "Isolation and characterization of a cDNA clone from *Catharanthus roseus* encoding NADPH-cytochrome P-450 mono-oxygenases in plants" pp. 47-60 (see entire document).

Kraus, P. F. X. et al., "Molecular cloning and heterologous expression of a cDNA encoding berbamunine synthase, a C—O phenol-coupling cytochrome P450 from the higher plant *Berberis stolonifera*," *Proc. Natl. Acad. Sci. USA,* Mar. 1995, 92(6), 2071-2075.

Stadler, R. et al., "The Purification and Characterization of a Unique Cytochrome P-450 Enzyme from *Berberis stolonifera* Plant Cell Cultures," *J. Biol. Chem.,* Jan. 15, 1993, 268(2), 823-831.

Tanahashi, T. et al., "Elicitor Induction and Characterization of Microsomal Protopine-6-Hydroxylase, the Central Enzyme in Benzophenanthridine Alkaloid Biosynthesis," *Phytochemistry*, 1990, 29(4), 1113-1122.

* cited by examiner

FIG. 2

Peptide 1  KVTIFFGTQK

Peptide 2  KVVDLDDYAADDDEFEEK
                         E

Peptide 3  KWFTEVAK
               D

Peptide 4  KVVDEIIVEK

Peptide 5  KYADLLNFPK

Peptide 6  KAALHALAK

Peptide 7  KDVHRTLHTIVQEQGSLDSSK

FIG. 3

```
Arabidopsis thaliana  .. 350  GSPLES-AVPPPFPGPCT
Catharanthus roseus   .. 389  GTPLAGSSLPPPFP-PCT
Helianthus tuberosus  .. 331  GTPLGGPTLQPPFP-PCT
Vigna radiata         .. 366  GTSLGG-SLLPPFPGPCS
Vicia sativa          .. 367  GTSLGG-SLLPPFPGPCT
                              *_ *   __ **** **_
                                     ─────────→

LGTGLARYADLLNPPRKSALVALAAYATEPSEARKLKHLTSPDGKD
LRTALTRYADLLNTPKKSALLALAAYASDPNEADRLKYLASPAGKD
LRKALTNYADLLSSPKKSTLLALAAEASDATEADRLQFLASREGKD
LRTALARYADLLNPPRKAALLALATEASEPS-DKRLXFLSSPQGKD
VRTALACYADLLNPPRKAAIVALAAHASEPSEARRLKFLSSPQGKD
_  *  ***** *_*  _*** *_    *    ** ***

EYSQWIVASQRSLLEVMAAFPSAKPPLGVFFAAIAPRLQPRYYSIS
EYAQSLVANQRSLLEVMAEFPSAKPPLGVFFAAIAPRLQPRFYSIS
EYAEWIVANQRSLLEVMEAFPSAKPPLGVFFAAIAPRLQPRYYSIS
EYSKWVVGSQRSLVEVMAEFPSAKPPLGVFFAAIAPRLQPRYYSIS
EYSKWVVGSQRSLLEVMADFPSAKPPLGVFFAAIAPRLQPRYYSIS
**   _* ****_***  ******************_****
                              ←─────────

SCQDWAPSRVHVTSALVYGPTPTGRIHKGVCSTWMKNAVP  498..
SSPRMAPSRIHVTCALVYEKTPGGRIHKGVCSTWMKNAIP  537..
SSPKMVPNRIHVTCALVYEKTPGGRIHKGICSTWMKNAVP  479..
SSPRFAPQRVHVTCALVYGPTPTGRIHKGVCSTWMKNAIP  513..
SSPRFAPQRVHVTCALVEGPTPTGRIHKGVCSTWMKSATP  515..
*_    * *_***_***   ** ******_****** * *
                              ←─────────
```

FIG. 5

```
1                                                                              50
MEQTAVKVSL  FDLFSSILNG  KLDPSNFSSD  SSAAILIENR  EILMILTTAI
MGSNNLANSI  ESMLG.ISIG  ....SEYISD  P.........  .IFIMVTTVA
*           *    *  *              *    **     *     **

51                                                                            100
AVFIGCGFLY  VWRRSSNKSS  KIVETQKLIV  EKEPE.PEVD  DGKKKVTIFF
SMLIGFGFFV  CMK.SSSSQS  KPIETYKPII  DKEEEEIEVD  PGKIKLTIFF
 ** **        **   *    * ** *  *   ** * ***    ** * ****

101                                                                           150
GTQTGTAEGF  AKALAEEAKA  RYEKAIFKVI  DLDDYGADDD  EFEEKLKKET
GTQTGTAEGF  AKALAEEIKA  KYKKAVVKVV  DLDDYAAEDD  QYEEKLKKES
**********  ******* **   *  **  **  ***** * **   *******

151                                                                           200
IALFFLATYG  DGEPTDNAAR  FYKWFTEGKE  REMWLQNLQF  GVFGLGNRQY
LVFFMVATYG  DGEPTDNAAR  FYKWFTQEHE  RGEWLQQLTY  GVFGLGNRQY
  *  ****  **********  ******  *   *  ***  *  **********

201                                                                           250
EHFNKVAKEV  DEILTEQGGK  RIVPVGLGDD  DQCIEDDFTA  WRELVWPELD
EHFNKIAVDV  DEQLGKQGAK  RIVQVGLGDD  DQCIEDDFTA  WRELLWTELD
*****  *  *  **  *  ** *   *** ******  **********  ****  *  ***

251                                                                           300
QLLLDESDKT  SVSTPYTAIV  PEYRVVFHDA  TDASLQDKNW  SNANGYTVYD
QLLKDEDAAP  SVATPYIATV  PEYRVVIHET  TVAALDDKHI  NTANGDVAFD
***  **      **  *** * *  ****** *   *  *  **    ***    *

301                                                                           350
VQHPCRANVV  VKKELHTPVS  DRSCIHLEFD  ISGTGLTYET  GDHVGVYSEN
ILHPCRTIVA  QQRELHKPKS  DRSCIHLEFD  ISGSSLTYET  GDHVGVYAEN
 ****  *     ***  * *   **********  ***  *****  ******* **

351                                                                           400
CVEVVEEAER  LLGYSSDTVF  SIHVDKEDGS  PISGSALAPP  FPTPCTLRTA
CDETVEEAGK  LLGQPLDLLF  SIHTDKEDGS  PQGSS..LPP  FPGPCTLRSA
*  *  ****    ***   *   *** ******    *    **  ** ***** *

401                                                                           450
LTRYADLLNS  PKKAALHALA  AYASDPKEAE  RLRYLASPAG  KDEYAQWIVA
LARYADLLNP  PRKASLIALS  AHASVPSEAE  RLRFLSSPLG  KNEYSKWVVG
*  *******  *  ** * **  * **  * ***  *** *  ** *  *  **  *  *

451                                                                           500
SQRSLLVVMA  EFPSAKAPIG  VFFAAVAPRL  LPRYYSISSS  NRMVPSRIHV
SQRSLLEIMA  EFPSAKPPLG  VFFAAVAPRL  PPRYYSISSS  PKFAPSRIHV
******  **  ****** * *  **********  *********     ******

501                                                                           550
TCALVHEKTP  AGRVHKGVCS  TWMKNSVSLE  ENHDCSSWAP  IFVRQSNFKL
TCALVYGQSP  TGRFHRGVCS  TWMKHAVPQD  S......WAP  IFVRTSNFKL
*****   *   ** * ****  ****  *            ***  ****  *****

551                                                                           600
PADSTVPIIM  IGPGTGLAPF  RGFMQERLAL  KNSGVELGPA  ILFFGCRNRQ
PADPSTPIIM  VGPGTGLAPF  RGFLQERMAL  KENGAQLGPA  VLFFGCRNRN
***  ****  **********  *** *** **   *  *  ****   ********

601                                                                           650
MDYIYEEELN  NFVKEGAISE  VVVAFSREGA  TKEYVQHKMA  EKASYIWEMI
MDFIYEDELN  NFVERGVISE  LVIAFSREGE  KKEYVQHKMM  EKATDVWNVI
** *** ***  ***  *  ***  *  ******  ********  ***  *    *

651                                                                           700
SQGAYLYVCG  DAKGMARDVH  RTLHTIAQEQ  GSLDNSKTES  LVKNLQMDGR
SGDGYLYVCG  DAKGMARDVH  RTLHTIAQEQ  GSMESSAABA  AVKKLQVEER
*   ******  **********  **********   **  *  *   **  **   *

701
YLRDVW
YLRDVW
******
```

FIG. 6a

```
CGGCACGAGCTTGTTAGTATCTCTTCTAGGGTTTGAAAAGAAGCACAGGGAGGAAGCAAAAGTCGAATCTACTTGAAATACAT
TCGATTGCTTCTCTCTGTTAAGCTTCAGAGTCTTCAGAGTCTCTGCTAATTATGGGTTCGAATAATTTAGCTAATTCGATTGAATCGA
TGTTAGGAATATCAATAGGATCAGAATATATTTCTGACCCATTTCATTATGGTCACAACTGTAGCTTCAATGCTGATT
GGATTTGGTTTCTTCGCATGTATGAAATCTTCGTCTTCTCAATCAAAACCTATTGAAACTTATAAACCAATAATTGATAA
AGAAGAAGAGGAGATTGAAGTTGATCCTGGTAAAATTAAGCTCACTATATTTTTGGTTACTCAGACTGGTACTGCTGAAG
GATTTGCTAAGGCATTGCAGAAGAATTAAGGCAAAGTACAAGAAAGCAGTTGTTAAAGTAGTTGACCTGGATGACTAT
GCAGCCGAGGATGATCAATATGAAGAAGAGAAATTAAAGAGAGAAGAGTCTTTGGTGTTGTTTTCATGGAGTCCACTTATGGTGATGG
TGAGCCAACTGACAATGCTGCGAGATTTACAATGGTTCACTCAGGAACATGAAAGGGGAGAGTGGCTTCAGCAACTAA
CTTATGGTGTTTTTGGGTTGGGTAACCGTCAATACGAGCATTTCAACAGATCGCGGTAGATGTGGATGAGCAACTCGGT
AACAAGGTGCAAAGCGCATTGTTCAAGTGGGGCTGTCAAGAACTACGGTCGCGGCTACCATCAATGATTTTACTGCTTGGCG
AGAATTGTTGTGGACTGAATTGGATCAGTTGCTCAAAGATGAGGATGCTGCTCCTTCAGTGGCTACACCGTATATTGCTA
CTGTTCCTGAATACAGGGTAGTGATTCACGAAACTACGGTCGCGGCTCGGATGATAAACACATAAATACTGCTAACGGC
GATGTTGCATTTGATATTTCCATCTTGCAGAACATCAGGCTCTCCTCCCTTGCTCAACAAAGAGAGCTCACAAACCAAGTCTGATAG
ATCCTGTATACATCTGGAGTTCGACATCTGGACATATCAGGCGTCAACCCTGGATTTGCTGTTTTCAATTCACACGGAT
AGAACTGCGATGAAACTGTCGAGGAAGCAGGAAGCTGTGTGGGTCAACCTGGATTTGCTGTTTTCAATTCACACGGAT
AAAGAAGACGGGTCACCCAGGGAAGCTCATTACCACCTCCTTCTGATTGCTCTTGCCACCTTACCGATCTGCCCTAGCACG
CTATGCTGATCTTTTGAATCCTCCTAGAAAGGCTTCTGAGAAGAATGAGTATTCAAAATGGGTAGTTGGAAGTCAGAGGAGTCTTTG
AGAGATTGCGCTTTTGTCATCACCTCTGGGAAAGACCCCCTCTTGGTGTTTTCTTTGCTGCAGTAGCCCCTCGCTTATGTGTATCG
GAGATCATGGCCGAGTTTCATCCTCTCCTAAGTTTGCTCCCTCAAGAATTCATGTCACGTGTCGTTGCTGACGTGCTTTAGTATGTCAAAGCC
ATACTATTCTATCTAAGGGTTCACCGAGGAGTGTGTTCGACAGCTGTGTTCGACAGCATGAAGCATCAGTTCCTCAGGATAGCTGGGCTCCTATTTT
CTACCGGAAGGGTCACCCAGGGAGTGTGTTCGACAGCTGTGACCGTGACCCTGAACCTCAATTATCATGGTGGGACCTGGTACAGGGTTAGCTCC
GTTCGAACGTCAAACTTCAAGTTACCAGCTGACCCCTGAACCTCAATTATCATGGTGGGACCTGGTACAGGGTTAGCTCC
TTTCAGAGGATTTCTGCAGGAAACATGGCCCTCAAGGAAACTAAACAACTTCGTGGAACAGGAGCAACCTGTGGAACAACTTCGGAGCTAGTT
GTAGGAATCGTAATATGGACTTCATTTATCAAGACGAACTAAACAACTTGTCAACATAAGATGATGAGAAAGCAACGGATGTATGGAATGT
ATGCCTTTCACGTGAAGGGGAAAGAAAGGAATATGTTCAACATAAGATGATGAGAAAGCAACGGATGTATGGAATGT
GATATCAGGGACGGTTATCTCTATGTGTGTGATGCCAAGGAATGCCAGAGATGTCCATCGCACGTTGCATACCA
TTGCCCAAGAACAGGGACCCATGAATCATCTGCTGCCAGTCATCTGCCAAGTCATCTGCCAAGTGCAGTAAAGAAACTCCAAGTGCAGTAAACGATATCTA
AGAGATGTCTGGTGATCAGTAGCTTGCCAAGCACTTCCAGACATCCCTTGATTCTTCCTCCAGTGGTTCCAAATCGAAGCTGGTATAA
ATCCTCCTGAAAATCCCAAGCACTTCCAGACATCCCTTGATTCTTCCTCCAGTGGTTCCAAATCGAAGCTGGTATAA
TTGAGAGCAGTGCAATTGTGACTACATGAGAGAAGCAAACATGAATAGAGACCATAGAATTAGAAAAGATCAAAATTCTCTTATCA
GAACAATGTTACAGGCAAAACTGTGTTTGCTTAATATAAATTCACACCATGGGTGTGACAACACTGAAACAGTATTAG
CTATACCAACAAAGTTATGCAAGGAAACAAAACTAGTTAGATCTTCTTTGGATTGATTACTGTAAGTTCTAACCAGA
TGATAGATTGTACTTAAAGATTCTTGTTTCTTATGGCTACCGAGAGGAGTATATTAATGCATTTAGAGTTTGAGAAAAAAAAAAAAAA
```

FIG. 6b

```
TTCTTCTTCCAATCGCATTCGAGAAAATTCAATCATCATCTTCAACTTCAGGAAGAAGAATCATCAGAAACACTGAAGCTCAT
CATCATCCTTGAAACTTATCGTCTTTGTTGACCTTTTGAAAAACTATGGAACAAACTGCGGTTAAAGTCTCTTTGTTTG
ATCTATTTTCTTCGATACTTAATGGAAAGTTGGATCCGTCGAACTTTTCTTCAGATTCAAGTGCTGCTATTTGATTGAA
AATCGTGAGATTTTAATGATCTTAACAACTGCTATTGCTGTTTTTATCGGTTGTGGTTTTCTCTACGTTTGGAGAAGATC
TTCAATAAGTCGAGTAAAATTGTTGAAACTCAAACTGTTGAAACTGATCGTTGAAAAGGAACCAGAACCTGAAGTTGATGGAA
AGAAGAAGGTTACTATCTTCTTCTTGGTACTCAAACTGGTACTGATTCGCAAAGGCACTTGCTGAAGAAGCAAAA
GCAAGATATGAAAAGGCAATCTTTAAAGTGATTGATCTGGATGATTACGGAGCAGATGATGATGAAGAGAAATT
GAAAAGGAAACTATAGCTCTTTCTTTTCTTGGCTACCTATGGAGATGGTGAACCTACAGATAATGCTGCAAGATTTTATA
AATGGTTCACGAGGGGAGAGGGAAATGTGGCTCCAGAATCTTCAATTTGGTGTCTTCGGTCTAGGCAATAGACAGTA
TGAGCATTTCAATAAGGTGGCAAAGGAGGTGGACGAGATATTCACTGCGTGGGCGGAGTTGGTATGGCCTGAATTGGATCAGTTGCTC
TAGGAGATGATGATCAATGCATAGAAGATGATTTCACTCCTTACACTCGCTACCACTGTTACGACGTTCAACACCATGCAGAG
CTTGATGAAAGTGATAAAACATCTGTTCTACTCCTTACACTGGCTACCACTGTTTTACGACGTTCAACACCATGCAGAG
TACTGATGCATCACTACAGACAAAAACTGGAGCAATGCAAATGGCTACTCCAGATACACTGTTACGACGTTCAACACCATGCAGAG
CCAATGTCGTTGTAAAGAGGAGCTTCACACTCCAGTATCTGATCGTTCTTGTATTCATCTGGAATTTGACATTTCTGGC
ACTGGGCTCACGTATGAAACAGGAGACCATGTCGGTGTTTACTCTGAGAATTGTGTTGAAGTTGTCGAGGAAGCAGAGAG
GCTATTGGGTTACTCATCAGACACCGTTTTTCAATCCATGTCGATAAAGAGGACGGCTCACCCATTAGTGGAAGCGCTC
TAGCTCCTCCTTTCCAACTCCCTGCACTCAAGAACACTAAACAGCACTAACACGATACGCTGATCTGTTGAATTCTCCAAGAAG
GCTGCTCTGCATGCTTTGGCTGCTTATGCATCCGATCAAAGGAAGCGGAGCGACTAAGGTATCTTGCTCTCCTGCTGG
GAAGGACGAATACGCCCAGTGGATACGTAGTCAGCAGTAGCTCCTGCCAAGATACTATTCATCTTCCAATAGGATG
CTCCAATTGGGGTTTTCTTGCAGCAGTAGCTCTGAAGAATTCTGGTGTAGAATTTGTGAAAGAGGGAGCTTCTCCGAAGTTGTTTCTTCAC
GTACCATCTAGGATTCATGTCACATGTGCATTGGTGCATGAAAAAACACCGGCAGGTCGGGTTCACAAGGAGTGTGTTC
AACCTGGATGAAGAATTCTGTGTCTTTGGAAGAAAACCATGATTGCAGCAGCTGGGCACCAATCTTTGTCAGGCAATCCA
ACTTCAAACTTCCTGCTGATTCTACAGTACCAATTATATTGATTGGGACCCGCTATCTCTCTTTGGATGCAGAAACAGACA
ATGCAGGAGCGATTAGCTCTGAAGAATTCTGGTGTAGAATTTGTGAAAGAGGGAGCTTCCACACCTGAACTCTGCCAGGAACA
GATGGATTACATATATGAAGGAGGAATACGTACAACAACTTTGTGAAAGAGGGAGAAGGCTTCCACACCTCTGCCAGGAACA
GTGAGGGAGCTACCAAGGAATACGTACAACAACTATAAAATGGCGGAGAAGCTACAGATGATGAAGGTATCACGTGATGTGTGGT
GCTTATCTTTATGTATGTGGTGATGCAAGGCATGGCTAGAGACGTAGAAGAATCTACAGATGATGAAGGTATCACGTGATGTGTGGT
GGGATCTTTGGACAACTCGAAGACCGAAAGCTTGGTGAAGAGCTTCATCAAAGAACGCGACATTAAGTTATATTCTCTAAACTGTTAATCCTGT
GATTGATTTTTCAGAAGAAATGCTTTATATACTTGAGGTAGCGGACATTAAGTTATATATTCTCTAAACTGTTAATCCTGT
TTGATTTCAGAAGAAATGCTTTATATACTTGAGGTAGCGGACATTAAGTTATATATTCTCTAAACTGTTAATCCTGT
AAAAAGGGATTGCTGTTTGTGTTTGCTCGCAATCAATATGACATATGAAACAAAAGAACTTCTGTTTGGAGGAAGAGAAAAAAAAAAAAAAA
ATTAACGAGTTTGTCCGTTATATATGACATATGACATATGAAACAAAAGAACTTCTGTTTGGAGGAAGAGAAAAAAAAAAAAAAA
```

FIG. 9a (1)

```
1/1                                             31/11
CGG CAC GAG CTT GTT AGT ATC TTC TAG GGT TTG AAA AGA AGC ACA GGG AGA AGC AAA AGT
 R   H   E   L   V   S   I   F   *   G   L   K   R   S   T   G   R   S   K   S
61/21                                           91/31
CGA ATC TAC TTG AAA TAC ATT CGA TTG CTT CTC TCT GTT TAA GCT TCA GAG TCT CTG CTA
 R   I   Y   L   K   Y   I   R   L   L   L   S   V   *   A   S   E   S   L   L
121/41                                          151/51
ATT ATG GGT TCG AAT AAT TTA GCT AAT TCG ATT GAA TCG ATG TTA GGA ATA TCA ATA GGA
 I   M   G   S   N   N   L   A   N   S   I   E   S   M   L   G   I   S   I   G
181/61                                          211/71
TCA GAA TAT ATT TCT GAC CCA ATT TTC ATT ATG GTC ACA ACT GTA GCT TCA ATG CTG ATT
 S   E   Y   I   S   D   P   I   F   I   M   V   T   T   V   A   S   M   L   I
241/81                                          271/91
GGA TTT GGT TTC TTC GCA TGT ATG AAA TCT TCG TCT TCT CAA TCA AAA CCT ATT GAA ACT
 G   F   G   F   F   A   C   M   K   S   S   S   S   Q   S   K   P   I   E   T
301/101                                         331/111
TAT AAA CCA ATA ATT GAT AAA GAA GAA GAG GAG ATT GAA GTT GAT CCT GGT AAA ATT AAG
 Y   K   P   I   I   D   K   E   E   E   E   I   E   V   D   P   G   K   I   K
361/121                                         391/131
CTC ACT ATA TTT TTT GGT ACT CAG ACT GGT ACT GCT GAA GGA TTT GCT AAG GCA TTG GCA
 L   T   I   F   F   G   T   Q   T   G   T   A   E   G   F   A   K   A   L   A
421/141                                         451/151
GAA GAA ATT AAG GCA AAG TAC AAG AAA GCA GTT GTT AAA GTA GTT GAC CTG GAT GAC TAT
 E   E   I   K   A   K   Y   K   K   A   V   V   K   V   V   D   L   D   D   Y
481/161                                         511/171
GCA GCC GAG GAT GAT CAA TAT GAA GAG AAA TTA AAG AAA GAG TCT TTG GTG TTT TTC ATG
 A   A   E   D   D   Q   Y   E   E   K   L   K   K   E   S   L   V   F   F   M
541/181                                         571/191
GTA GCC ACT TAT GGT GAT GGT GAG CCA ACT GAC AAT GCT GCG AGA TTT TAC AAA TGG TTC
 V   A   T   Y   G   D   G   E   P   T   D   N   A   A   R   F   Y   K   W   F
601/201                                         631/211
ACT CAG GAA CAT GAA AGG GGA GAG TGG CTT CAG CAA CTA ACT TAT GGT GTT TTT GGT TTG
 T   Q   E   H   E   R   G   E   W   L   Q   Q   L   T   Y   G   V   F   G   L
661/221                                         691/231
GGT AAC CGT CAA TAC GAG CAT TTC AAC AAG ATC GCG GTA GAT GTG GAT GAG CAA CTC GGT
 G   N   R   Q   Y   E   H   F   N   K   I   A   V   D   V   D   E   Q   L   G
721/241                                         751/251
AAA CAA GGT GCA AAG CGC ATT GTT CAA GTG GGG CTC GGT GAC GAT GAT CAA TGC ATT GAA
 K   Q   G   A   K   R   I   V   Q   V   G   L   G   D   D   D   Q   C   I   E
781/261                                         811/271
GAT GAT TTT ACT GCT TGG CGA GAA TTG TTC TGG ACT GAA TTG GAT CAG TTG CTC AAA GAT
 D   D   F   T   A   W   R   E   L   L   W   T   E   L   D   Q   L   L   K   D
841/281                                         871/291
GAG GAT GCT GCT CCT TCA GTG GCT ACA CCG TAT ATT GCT ACT GTT CCT GAA TAC AGG GTA
 E   D   A   A   P   S   V   A   T   P   Y   I   A   T   V   P   E   Y   R   V
901/301                                         931/311
GTG ATT CAC GAA ACT ACG GTC GCG GCT CTG GAT GAT AAA CAC ATA AAT ACT GCT AAC GGC
 V   I   H   E   T   T   V   A   A   L   D   D   K   H   I   N   T   A   N   G
961/321                                         991/331
GAT GTT GCA TTT GAT ATT CTC CAT CCT TGC AGA ACC ATT GTT GCT CAA CAA AGA GAG CTC
 D   V   A   F   D   I   L   H   P   C   R   T   I   V   A   Q   Q   R   E   L
1021/341                                        1051/351
```

FIG. 9a (2)

```
CAC AAA CCC AAG TCT GAT AGA TCC TGT ATA CAT CTG GAG TTC GAC ATA TCA GGC TCT TCC
 H   K   P   K   S   D   R   S   C   I   H   L   E   F   D   I   S   G   S   S
1081/361                                1111/371
CTT ACA TAT GAG ACT GGA GAT CAT GTT GGT GTT TAT GCT GAG AAC TGC GAT GAA ACT GTC
 L   T   Y   E   T   G   D   H   V   G   V   Y   A   E   N   C   D   E   T   V
1141/381                                1171/391
GAG GAA GCA GGG AAG CTG TTG GGT CAA CCC CTG GAT TTG CTG TTT TCA ATT CAC ACG GAT
 E   E   A   G   K   L   L   G   Q   P   L   D   L   L   F   S   I   H   T   D
1201/401                                1231/411
AAA GAA GAC GGG TCA CCC CAG GGA AGC TCA TTA CCA CCT CCT TTC CCA GGT CCT TGC ACC
 K   E   D   G   S   P   Q   G   S   S   L   P   P   P   F   P   G   P   C   T
1261/421                                1291/431
TTA CGA TCT GCC CTA GCA CGC TAT GCT GAT CTT TTG AAT CCT CCT AGA AAG GCT TCT CTG
 L   R   S   A   L   A   R   Y   A   D   L   L   N   P   P   R   K   A   S   L
1321/441                                1351/451
ATT GCT CTG TCC GCT CAT GCA TCT GTA CCC AGT GAA GCA GAG AGA TTG CGC TTT TTG TCA
 I   A   L   S   A   H   A   S   V   P   S   E   A   E   R   L   R   F   L   S
1381/461                                1411/471
TCA CCT CTG GGA AAG AAT GAG TAT TCA AAA TGG GTA GTT GGA AGT CAG AGG AGT CTT TTG
 S   P   L   G   K   N   E   Y   S   K   W   V   V   G   S   Q   R   S   L   L
1441/481                                1471/491
GAG ATC ATG GCC GAG TTT CCA TCA GCA AAA CCC CCT CTT GGT GTT TTC TTT GCT GCA GTA
 E   I   M   A   E   F   P   S   A   K   P   P   L   G   V   F   F   A   A   V
1501/501                                1531/511
GCC CCT CGC TTA CCG CCT CGA TAC TAT TCT ATC TCA TCC TCT CCT AAG TTT GCT CCC TCA
 A   P   R   L   P   P   R   Y   Y   S   I   S   S   S   P   K   F   A   P   S
1561/521                                1591/531
AGA ATT CAT GTG ACG TGT GCT TTA GTA TAT GGT CAA AGC CCT ACC GGA AGG GTT CAC CGA
 R   I   H   V   T   C   A   L   V   Y   G   Q   S   P   T   G   R   V   H   R
1621/541                                1651/551
GGA GTG TGT TCG ACA TGG ATG AAG CAT GCA GTT CCT CAG GAT AGC TGG GCT CCT ATT TTT
 G   V   C   S   T   W   M   K   H   A   V   P   Q   D   S   W   A   P   I   F
1681/561                                1711/571
GTT CGA ACG TCA AAC TTC AAG TTA CCA GCT GAC CCC TCA ACT CCA ATT ATC ATG GTG GGA
 V   R   T   S   N   F   K   L   P   A   D   P   S   T   P   I   I   M   V   G
1741/581                                1771/591
CCT GGT ACA GGG TTA GCT CCT TTC AGA GGA TTT CTG CAG GAA AGA ATG GCC CTC AAG GAA
 P   G   T   G   L   A   P   F   R   G   F   L   Q   E   R   M   A   L   K   E
1801/601                                1831/611
AAT GGT GCT CAA CTT GGC CCA GCA GTG CTC TTT TTC GGA TGT AGG AAT CGT AAT ATG GAC
 N   G   A   Q   L   G   P   A   V   L   F   F   G   C   R   N   R   N   M   D
1861/621                                1891/631
TTC ATT TAT GAA GAC GAA CTA AAC AAC TTC GTG GAA CGA GGA GTA ATT TCG GAG CTA GTT
 F   I   Y   E   D   E   L   N   N   F   V   E   R   G   V   I   S   E   L   V
1921/641                                1951/651
ATT GCC TTT TCA CGT GAA GGG GAA AAG AAG GAA TAT GTT CAA CAT AAG ATG ATG GAG AAA
 I   A   F   S   R   E   G   E   K   K   E   Y   V   Q   H   K   M   M   E   K
1981/661                                2011/671
GCA ACG GAT GTA TGG AAT GTG ATA TCA GGG GAC GGT TAT CTC TAT GTG TGT GGT GAT GCC
 A   T   D   V   W   N   V   I   S   G   D   G   Y   L   Y   V   C   G   D   A
2041/681                                2071/691
```

FIG. 9a (3)

```
AAG GGA ATG GCC AGA GAT GTC CAT CGC ACG TTG CAT ACC ATT GCC CAA GAA CAG GGA CCC
 K   G   M   A   R   D   V   H   R   T   L   H   T   I   A   Q   E   Q   G   P
2101/701                                2131/711
ATG GAA TCA TCT GCT GCC GAA GCT GCA GTA AAG AAA CTC CAA GTT GAA GAA CGA TAT CTA
 M   E   S   S   A   A   E   A   A   V   K   K   L   Q   V   E   E   R   Y   L
2161/721                                2191/731
AGA GAT GTC TGG TGA TCG AAT GTA GCT TGC CAA GTC CCC TTT TCT TGG CTG GTC TGT TTA
 R   D   V   W   *   S   N   V   A   C   Q   V   P   F   S   W   L   V   C   L
2221/741                                2251/751
TGG TTT CTA TTA TAT TAT TGA TCC TCC TCT GAA AAT CCC AAG CAC TTC CAG ACA TCC CTC
 W   F   L   L   Y   Y   *   S   S   S   E   N   P   K   H   F   Q   T   S   L
2281/761                                2311/771
GAT TCT TCC TCC AGT GGT TCC AAA TCG AAG CTC GGT ATA ATT GAG AGC AGT GCA ATT GTG
 D   S   S   S   S   G   S   K   S   K   L   G   I   I   E   S   S   A   I   V
2341/781                                2371/791
ACT ACA TGA GAA GCA AAC ATC GAA TAC CAT AGA ATT AGA AAG ATC AAA ATT CTC TTA TCA
 T   T   *   E   A   N   I   E   Y   H   R   I   R   K   I   K   I   L   L   S
2401/801                                2431/811
GAA CAA TGT TAC AGG CAA AAC TGT GTT TGC TTA ATA TAA ATT TCA CAC CAT GGG TGT GGA
 E   Q   C   Y   R   Q   N   C   V   C   L   I   *   I   S   H   H   G   C   G
2461/821                                2491/831
CAA CAC TGA AAC AGT ATT AGC TAT ACC AAC AAA GTT ATG CAA GGA AAC ACA AAC TAG TTA
 Q   H   *   N   S   I   S   Y   T   N   K   V   M   Q   G   N   T   N   *   L
2521/841                                2551/851
GAT CTT CTC TTT GGA TTG ATT ACT GTA AGT TCT AAC CAG ATG ATA GAT TGT ACT TAA AGA
 D   L   L   F   G   L   I   T   V   S   S   N   Q   M   I   D   C   T   *   R
2581/861                                2611/871
TTC TTG TTT TCT TAT GGC TAC CGA GAG GAG TAT ATT AAT GCA TTT AGA GTT TTG AGA AAA
 F   L   F   S   Y   G   Y   R   E   E   Y   I   N   A   F   R   V   L   R   K
2641/881
AAA AAA AAA A
 K   K   K
```

FIG. 9b (1)

```
1/1                                       31/11
TTC TTC TTC CAA TCG CAT TCG AGA AAA TTC   AAT CAT CTT CAA CTT CAG GAA GAA GAA TCA
 F   F   F   Q   S   H   S   R   K   F     N   H   L   Q   L   Q   E   E   E   S
61/21                                     91/31
TCA GAA ACA CTG AAG CTC ATC ATC ATC CTT   GAA ACT TAT CGT CTT TGT TTG ACC TTT TGA
 S   E   T   L   K   L   I   I   I   L     E   T   Y   R   L   C   L   T   F   *
121/41                                    151/51
AAA ACT ATG GAA CAA ACT GCG GTT AAA GTC   TCT TTG TTT GAT CTA TTT TCT TCG ATA CTT
 K   T   M   E   Q   T   A   V   K   V     S   L   F   D   L   F   S   S   I   L
181/61                                    211/71
AAT GGA AAG TTG GAT CCG TCG AAC TTT TCT   TCA GAT TCA AGT GCT GCT ATT TTG ATT GAA
 N   G   K   L   D   P   S   N   F   S     S   D   S   S   A   A   I   L   I   E
241/81                                    271/91
AAT CGT GAG ATT TTA ATG ATC TTA ACA ACT   GCT ATT GCT GTT TTT ATC GGT TGT GGT TTT
 N   R   E   I   L   M   I   L   T   T     A   I   A   V   F   I   G   C   G   F
301/101                                   331/111
CTC TAC GTT TGG AGA AGA TCT TCA AAT AAG   TCG AGT AAA ATT GTT GAA ACT CAG AAA TTG
 L   Y   V   W   R   R   S   S   N   K     S   S   K   I   V   E   T   Q   K   L
361/121                                   391/131
ATC GTT GAA AAG GAA CCA GAA CCT GAA GTT   GAT GAT GGA AAG AAG AAG GTT ACT ATC TTC
 I   V   E   K   E   P   E   P   E   V     D   D   G   K   K   K   V   T   I   F
421/141                                   451/151
TTT GGT ACT CAA ACT GGT ACA GCT GAA GGA   TTC GCA AAG GCA CTT GCT GAA GAA GCA AAA
 F   G   T   Q   T   G   T   A   E   G     F   A   K   A   L   A   E   E   A   K
481/161                                   511/171
GCA AGA TAT GAA AAG GCA ATC TTT AAA GTG   ATT GAT CTG GAT GAT TAC GGA GCA GAT GAT
 A   R   Y   E   K   A   I   F   K   V     I   D   L   D   D   Y   G   A   D   D
541/181                                   571/191
GAT GAA TTC GAA GAG AAA TTG AAA AAG GAA   ACT ATA GCT CTT TTC TTT TTG GCT ACC TAT
 D   E   F   E   E   K   L   K   K   E     T   I   A   L   F   F   L   A   T   Y
601/201                                   631/211
GGA GAT GGT GAA CCT ACA GAT AAT GCT GCA   AGA TTT TAT AAA TGG TTC ACA GAG GGA GAG
 G   D   G   E   P   T   D   N   A   A     R   F   Y   K   W   F   T   E   G   E
661/221                                   691/231
AGG GAA ATG TGG CTC CAG AAT CTT CAA TTT   GGT GTC TTC GGT CTA GGC AAT AGA CAG TAT
 R   E   M   W   L   Q   N   L   Q   F     G   V   F   G   L   G   N   R   Q   Y
721/241                                   751/251
GAG CAT TTC AAT AAG GTG GCA AAG GAG GTG   GAC GAG ATA CTC ACT GAA CAG GGT GGG AAG
 E   H   F   N   K   V   A   K   E   V     D   E   I   L   T   E   Q   G   G   K
781/261                                   811/271
CGT ATT GTT CCC GTG GGT CTA GGA GAT GAT   GAT CAA TGC ATA GAA GAT GAT TTC ACT GCG
 R   I   V   P   V   G   L   G   D   D     D   Q   C   I   E   D   D   F   T   A
841/281                                   871/291
TGG CGG GAG TTG GTA TGG CCT GAA TTG GAT   CAG TTG CTC CTT GAT GAA AGT GAT AAA ACA
 W   R   E   L   V   W   P   E   L   D     Q   L   L   L   D   E   S   D   K   T
901/301                                   931/311
TCT GTT TCT ACT CCT TAC ACT GCC ATC GTA   CCA GAA TAC AGG GTA GTA TTC CAT GAT GCT
 S   V   S   T   P   Y   T   A   I   V     P   E   Y   R   V   V   F   H   D   A
961/321                                   991/331
ACT GAT GCA TCA CTA CAA GAC AAA AAC TGG   AGC AAT GCA AAT GGC TAC ACT GTT TAC GAC
 T   D   A   S   L   Q   D   K   N   W     S   N   A   N   G   Y   T   V   Y   D
1021/341                                  1051/351
```

FIG. 9b (2)

```
GTT CAA CAC CCA TGC AGA GCC AAT GTC GTT GTA AAG AAG GAG CTT CAC ACT CCA GTA TCT
 V   Q   H   P   C   R   A   N   V   V   V   K   K   E   L   H   T   P   V   S
1081/361                                   1111/371
GAT CGT TCT TGT ATT CAT CTG GAA TTT GAC ATT TCT GGC ACT GGG CTC ACG TAT GAA ACA
 D   R   S   C   I   H   L   E   F   D   I   S   G   T   G   L   T   Y   E   T
1141/381                                   1171/391
GGA GAC CAT GTC GGT GTT TAC TCT GAG AAT TGT GTT GAA GTT GTC GAG GAA GCA GAG AGG
 G   D   H   V   G   V   Y   S   E   N   C   V   E   V   V   E   E   A   E   R
1201/401                                   1231/411
CTA TTG GGT TAC TCA TCA GAC ACC GTT TTT TCA ATC CAT GTC GAT AAA GAG GAC GGC TCA
 L   L   G   Y   S   S   D   T   V   F   S   I   H   V   D   K   E   D   G   S
1261/421                                   1291/431
CCC ATT AGT GGA AGC GCT CTA GCT CCT CCT TTT CCA ACT CCC TGC ACT CTA AGA ACA GCA
 P   I   S   G   S   A   L   A   P   P   F   P   T   P   C   T   L   R   T   A
1321/441                                   1351/451
CTA ACA CGA TAC GCT GAT CTG TTG AAT TCT CCC AAG AAG GCT GCT CTG CAT GCT TTG GCT
 L   T   R   Y   A   D   L   L   N   S   P   K   K   A   A   L   H   A   L   A
1381/461                                   1411/471
GCT TAT GCA TCC GAT CCA AAG GAA GCG GAG CGA CTA AGG TAT CTT GCG TCT CCT GCT GGG
 A   Y   A   S   D   P   K   E   A   E   R   L   R   Y   L   A   S   P   A   G
1441/481                                   1471/491
AAG GAC GAA TAC GCC CAG TGG ATA GTA GCT AGT CAG AGA AGT CTG CTA GTG GTC ATG GCT
 K   D   E   Y   A   Q   W   I   V   A   S   Q   R   S   L   L   V   V   M   A
1501/501                                   1531/511
GAA TTC CCA TCA GCA AAG GCT CCA ATT GGG GTT TTC TTT GCA GCA GTA GCT CCT CGC TTG
 E   F   P   S   A   K   A   P   I   G   V   F   F   A   A   V   A   P   R   L
1561/521                                   1591/531
CTG CCA AGA TAC TAT TCT ATT TCA TCT TCC AAT AGG ATG GTA CCA TCT AGG ATT CAT GTC
 L   P   R   Y   Y   S   I   S   S   S   N   R   M   V   P   S   R   I   H   V
1621/541                                   1651/551
ACA TGT GCA TTG GTG CAT GAA AAA ACA CCG GCA GGT CGG GTT CAC AAA GGA GTG TGT TCA
 T   C   A   L   V   H   E   K   T   P   A   G   R   V   H   K   G   V   C   S
1681/561                                   1711/571
ACC TGG ATG AAG AAT TCT GTG TCT TTG GAA GAA AAC CAT GAT TGC AGC AGC TGG GCA CCA
 T   W   M   K   N   S   V   S   L   E   E   N   H   D   C   S   S   W   A   P
1741/581                                   1771/591
ATC TTT GTC AGG CAA TCC AAC TTC AAA CTT CCT GCT GAT TCT ACA GTA CCA ATT ATA ATG
 I   F   V   R   Q   S   N   F   K   L   P   A   D   S   T   V   P   I   I   M
1801/601                                   1831/611
ATT GGT CCT GGG ACT GGA TTA GCT CCC TTT AGG GGA TTC ATG CAG GAG CGA TTA GCT CTG
 I   G   P   G   T   G   L   A   P   F   R   G   F   M   Q   E   R   L   A   L
1861/621                                   1891/631
AAG AAT TCT GGT GTA GAA TTG GGA CCC GCT ATC CTC TTC TTT GGA TGC AGA AAC AGA CAG
 K   N   S   G   V   E   L   G   P   A   I   L   F   F   G   C   R   N   R   Q
1921/641                                   1951/651
ATG GAT TAC ATA TAT GAA GAG GAG CTA AAC AAC TTT GTG AAA GAG GGA GCT ATC TCC GAA
 M   D   Y   I   Y   E   E   E   L   N   N   F   V   K   E   G   A   I   S   E
1981/661                                   2011/671
GTT GTT GTT GCT TTC TCA CGT GAG GGA GCT ACC AAG GAA TAC GTA CAA CAT AAA ATG GCG
 V   V   V   A   F   S   R   E   G   A   T   K   E   Y   V   Q   H   K   M   A
2041/681                                   2071/691
```

FIG. 9b (3)

```
GAG AAG GCT TCC TAC ATC TGG GAA ATG ATC TCT CAA GGT GCT TAT CTT TAT GTA TGT GGT
 E   K   A   S   Y   I   W   E   M   I   S   Q   G   A   Y   L   Y   V   C   G
2101/701                                    2131/711
GAT GCC AAG GGC ATG GCT AGA GAC GTA CAT CGA ACT CTC CAC ACC ATT GCC CAG GAA CAG
 D   A   K   G   M   A   R   D   V   H   R   T   L   H   T   I   A   Q   E   Q
2161/721                                    2191/731
GGA TCT TTG GAC AAC TCG AAG ACC GAA AGC TTG GTG AAG AAT CTA CAG ATG GAT GGA AGG
 G   S   L   D   N   S   K   T   E   S   L   V   K   N   L   Q   M   D   G   R
2221/741                                    2251/751
TAT CTA CGT GAT GTG TGG TGA TTG ATT TTT TCA GCA CGG TTA CAA TCT AGC TTC ATC AAA
 Y   L   R   D   V   W   *   L   I   F   S   A   R   L   Q   S   S   F   I   K
2281/761                                    2311/771
GAA CGC GCT TGA GAA GCA TAA ATC TTA GTT GCA GAG ATG TTG ATT TCA GAA GAA ATG CTT
 E   R   A   *   E   A   *   I   L   V   A   E   M   L   I   S   E   E   M   L
2341/781                                    2371/791
TAT ATA CTT GAG GTA GCG GAC ATT AAT CCT TTT CTC TCT CTC TAA ACT GTT AAT CCT GTA
 Y   I   L   E   V   A   D   I   N   P   F   L   S   L   *   T   V   N   P   V
2401/801                                    2431/811
AAA AAG GGA TTG CTG TTT GTG TTT GCT CGC AAT CAA TTA AGT TAT ATT CTT TGG TCT ATG
 K   K   G   L   L   F   V   F   A   R   N   Q   L   S   Y   I   L   W   S   M
2461/821                                    2491/831
GCA TTC GTT AGA CAA ATA TAT TAA CGA GTT TGT CCG TTA TAT ATG ACA TAT GAA ACA AAA
 A   F   V   R   Q   I   Y   *   R   V   C   P   L   Y   M   T   Y   E   T   K
2521/841                                    2551/851
GAA CTT CTG TTT GGA GGA AGA GAA AAA AAA AAA AA
 E   L   L   F   G   G   R   E   K   K   K
```

FIG. 10a (1)

```
   1 AAGCTTCAGAGTCTCTGCTAATT ATG GGT TCG AAT AAT TTA GCT AAT TCG ATT GAA TCG ATG TTA  65
   1                         M   G   S   N   N   L   A   N   S   I   E   S   M   L    14

66 GGA ATA TCA ATA GGA TCA GAA TAT ATT TCT GAC CCA ATT TTC ATT ATG GTC ACA ACT GTA 125
  15 G   I   S   I   G   S   E   Y   I   S   D   P   I   F   I   M   V   T   T   V    34

126 GCT TCA ATG CTG ATT GGA TTT GGT TTC TTC GCA TGT ATG AAA TCT TCG TCT TCT CAA TCA 185
  35 A   S   M   L   I   G   F   G   F   F   A   C   M   K   S   S   S   S   Q   S    54

186 AAA CCT ATT GAA ACT TAT AAA CCA ATA ATT GAT AAA GAA GAA GAG GAG ATT GAA GTT GAT 245
  55 K   P   I   E   T   Y   K   P   I   I   D   K   E   E   E   E   I   E   V   D    74

246 CCT GGT AAA ATT AAG CTC ACT ATA TTT TTT GGT ACT CAG ACT GGT ACT GCT GAA GGA TTT 305
  75 P   G   K   I   K   L   T   I   F   F   G   T   Q   T   G   T   A   E   G   F    94

306 GCT AAG GCA TTG GCA GAA GAA ATT AAG GCA AAG TAC AAG AAA GCA GTT GTT AAA GTA GTT 365
  95 A   K   A   L   A   E   E   I   K   A   K   Y   K   K   A   V   V   K   V   V   114

366 GAC CTG GAT GAC TAT GCA GCC GAG GAT GAT CAA TAT GAA GAG AAA TTA AAG AAA GAG TCT 425
 115 D   L   D   D   Y   A   A   E   D   D   Q   Y   E   E   K   L   K   K   E   S   134

426 TTG GTG TTT TTC ATG GTA GCC ACT TAT GGT GAT GGT GAG CCA ACT GAC AAT GCT GCG AGA 485
 135 L   V   F   F   M   V   A   T   Y   G   D   G   E   P   T   D   N   A   A   R   154

486 TTT TAC AAA TGG TTC ACT CAG GAA CAT GAA AGG GGA GAG TGG CTT CAG CAA CTA ACT TAT 545
 155 F   Y   K   W   F   T   Q   E   H   E   R   G   E   W   L   Q   Q   L   T   Y   174

546 GGT GTT TTT GGT TTG GGT AAC CGT CAA TAC GAG CAT TTC AAC AAG ATC GCG GTA GAT GTG 605
 175 G   V   F   G   L   G   N   R   Q   Y   E   H   F   N   K   I   A   V   D   V   194

606 GAT GAG CAA CTC GGT AAA CAA GGT GCA AAG CGC ATT GTT CAA GTG GGG CTC GGT GAC GAT 665
 195 D   E   Q   L   G   K   Q   G   A   K   R   I   V   Q   V   G   L   G   D   D   214

666 GAT CAA TGC ATT GAA GAT GAT TTT ACT GCT TGG CGA GAA TTG TTG TGG ACT GAA TTG GAT 725
 215 D   Q   C   I   E   D   D   F   T   A   W   R   E   L   L   W   T   E   L   D   234

726 CAG TTG CTC AAA GAT GAG GAT GCT GCT CCT TCA GTG GCT ACA CCG TAT ATT GCT ACT GTT 785
 235 Q   L   L   K   D   E   D   A   A   P   S   V   A   T   P   Y   I   A   T   V   254

786 CCT GAA TAC AGG GTA GTG ATT CAC GAA ACT ACG GTC GCG GCT CTG GAT GAT AAA CAC ATA 845
 255 P   E   Y   R   V   V   I   H   E   T   T   V   A   A   L   D   D   K   H   I   274

846 AAT ACT GCT AAC GGC GAT GTT GCA TTT GAT ATT CTC CAT CCT TGC AGA ACC ATT GTT GCT 905
 275 N   T   A   N   G   D   V   A   F   D   I   L   H   P   C   R   T   I   V   A   294

906 CAA CAA AGA GAG CTC CAC AAA CCC AAG TCT GAT AGA TCC TGT ATA CAT CTG GAG TTC GAC 965
 295 Q   Q   R   E   L   H   K   P   K   S   D   R   S   C   I   H   L   E   F   D   314

966 ATA TCA GGC TCT TCC CTT ACA TAT GAG ACT GGA GAT CAT GTT GGT GTT TAT GCT GAG AAC 1025
 315 I   S   G   S   S   L   T   Y   E   T   G   D   H   V   G   V   Y   A   E   N   334

1026 TGC GAT GAA ACT GTC GAG GAA GCA GGG AAG CTG TTG GGT CAA CCC CTG GAT TTG CTG TTT 1085
 335 C   D   E   T   V   E   E   A   G   K   L   L   G   Q   P   L   D   L   L   F   354

1086 TCA ATT CAC ACG GAT AAA GAA GAC GGG TCA CCC CAG GGA AGC TCA TTA CCA CCT CCT TTC 1145
 355 S   I   H   T   D   K   E   D   G   S   P   Q   G   S   S   L   P   P   P   F   374
```

FIG. 10a (2)

```
1146 CCA GGT CCT TGC ACC TTA CGA TCT GCC CTA GCA CGC TAT GCT GAT CTT TTG AAT CCT CCT 1205
 375 P   G   P   C   T   L   R   S   A   L   A   R   Y   A   D   L   L   N   P   P   394

1206 AGA AAG GCT TCT CTG ATT GCT CTG TCC GCT CAT GCA TCT GTA CCC AGT GAA GCA GAG AGA 1265
 395 R   K   A   S   L   I   A   L   S   A   H   A   S   V   P   S   E   A   E   R   414

1266 TTG CGC TTT TTG TCA TCA CCT CTG GGA AAG AAT GAG TAT TCA AAA TGG GTA GTT GGA AGT 1325
 415 L   R   F   L   S   S   P   L   G   K   N   E   Y   S   K   W   V   V   G   S   434

1326 CAG AGG AGT CTT TTG GAG ATC ATG GCC GAG TTT CCA TCA GCA AAA CCC CCT CTT GGT GTT 1385
 435 Q   R   S   L   L   E   I   M   A   E   F   P   S   A   K   P   P   L   G   V   454

1386 TTC TTT GCT GCA GTA GCC CCT CGC TTA CCG CCT CGA TAC TAT TCT ATC TCA TCC TCT CCT 1445
 455 F   F   A   A   V   A   P   R   L   P   P   R   Y   Y   S   I   S   S   S   P   474

1446 AAG TTT GCT CCC TCA AGA ATT CAT GTG ACG TGT GCT TTA GTA TAT GGT CAA AGC CCT ACC 1505
 475 K   F   A   P   S   R   I   H   V   T   C   A   L   V   Y   G   Q   S   P   T   494

1506 GGA AGG GTT CAC CGA GGA GTG TGT TCG ACA TGG ATG AAG CAT GCA GTT CCT CAG GAT AGC 1565
 495 G   R   V   H   R   G   V   C   S   T   W   M   K   H   A   V   P   Q   D   S   514

1566 TGG GCT CCT ATT TTT GTT CGA ACG TCA AAC TTC AAG TTA CCA GCT GAC CCC TCA ACT CCA 1625
 515 W   A   P   I   F   V   R   T   S   N   F   K   L   P   A   D   P   S   T   P   534

1626 ATT ATC ATG GTG GGA CCT GGT ACA GGG TTA GCT CCT TTC AGA GGA TTT CTG CAG GAA AGA 1685
 535 I   I   M   V   G   P   G   T   G   L   A   P   F   R   G   F   L   Q   E   R   554

1686 ATG GCC CTC AAG GAA AAT GGT GCT CAA CTT GGC CCA GCA GTG CTC TTT TTC GGA TGT AGG 1745
 555 M   A   L   K   E   N   G   A   Q   L   G   P   A   V   L   F   F   G   C   R   574

1746 AAT CGT AAT ATG GAC TTC ATT TAT GAA GAC GAA CTA AAC AAC TTC GTG GAA CGA GGA GTA 1805
 575 N   R   N   M   D   F   I   Y   E   D   E   L   N   N   F   V   E   R   G   V   594

1806 ATT TCG GAG CTA GTT ATT GCC TTT TCA CGT GAA GGG GAA AAG AAG GAA TAT GTT CAA CAT 1865
 595 I   S   E   L   V   I   A   F   S   R   E   G   E   K   K   E   Y   V   Q   H   614

1866 AAG ATG ATG GAG AAA GCA ACG GAT GTA TGG AAT GTG ATA TCA GGG GAC GGT TAT CTC TAT 1925
 615 K   M   M   E   K   A   T   D   V   W   N   V   I   S   G   D   G   Y   L   Y   634

1926 GTG TGT GGT GAT GCC AAG GGA ATG GCC AGA GAT GTC CAT CGC ACG TTG CAT ACC ATT GCC 1985
 635 V   C   G   D   A   K   G   M   A   R   D   V   H   R   T   L   H   T   I   A   654

1986 CAA GAA CAG GGA CCC ATG GAA TCA TCT GCT GCC GAA GCT GCA GTA AAG AAA CTC CAA GTT 2045
 655 Q   E   Q   G   P   M   E   S   S   A   A   E   A   A   V   K   K   L   Q   V   674

2046 GAA GAA CGA TAT CTA AGA GAT GTC TGG TGA TCGA ATG TAG CTTGCCAAtcactag        2100
 675 E   E   R   Y   L   R   D   V   W   *    M   *                              2
```

FIG. 10b (1)

```
   1 tgcagcccgggggatccgccCT ATG GAA CAA ACT GCG GTT AAA GTC TCT TTG TTT GAT CTA TTT  64
   1                        M   E   Q   T   A   V   K   V   S   L   F   D   L   F    14

65 TCT TCG ATA CTT AAT GGA AAG TTG GAT CCG TCG AAC TTT TCT TCA GAT TCA AGT GCT GCT 124
  15 S   S   I   L   N   G   K   L   D   P   S   N   F   S   S   D   S   S   A   A   34

125 ATT TTG ATT GAA AAT CGT GAG ATT TTA ATG ATC TTA ACA ACT GCT ATT GCT GTT TTT ATC 184
  35 I   L   I   E   N   R   E   I   L   M   I   L   T   T   A   I   A   V   F   I   54

185 GGT TGT GGT TTT CTC TAC GTT TGG AGA AGA TCT TCA AAT AAG TCG AGT AAA ATT GTT GAA 244
  55 G   C   G   F   L   Y   V   W   R   R   S   S   N   K   S   S   K   I   V   E   74

245 ACT CAG AAA TTG ATC GTT GAA AAG GAA CCA GAA CCT GAA GTT GAT GAT GGA AAG AAG AAG 304
  75 T   Q   K   L   I   V   E   K   E   P   E   P   E   V   D   D   G   K   K   K   94

305 GTT ACT ATC TTC TTT GGT ACT CAA ACT GGT ACA GCT GAA GGA TTC GCA AAG GCA CTT GCT 364
  95 V   T   I   F   F   G   T   Q   T   G   T   A   E   G   F   A   K   A   L   A   114

365 GAA GAA GCA AAA GCA AGA TAT GAA AAG GCA ATC TTT AAA GTG ATT GAT CTG GAT GAT TAC 424
 115 E   E   A   K   A   R   Y   E   K   A   I   F   K   V   I   D   L   D   D   Y   134

425 GGA GCA GAT GAT GAT GAA TTC GAA GAG AAA TTG AAA AAG GAA ACT ATA GCT CTT TTC TTT 484
 135 G   A   D   D   D   E   F   E   E   K   L   K   K   E   T   I   A   L   F   F   154

485 TTG GCT ACC TAT GGA GAT GGT GAA CCT ACA GAT AAT GCT GCA AGA TTT TAT AAA TGG TTC 544
 155 L   A   T   Y   G   D   G   E   P   T   D   N   A   A   R   F   Y   K   W   F   174

545 ACA GAG GGA GAG AGG GAA ATG TGG CTC CAG AAT CTT CAA TTT GGT GTC TTC GGT CTA GGC 604
 175 T   E   G   E   R   E   M   W   L   Q   N   L   Q   F   G   V   F   G   L   G   194

605 AAT AGA CAG TAT GAG CAT TTC AAT AAG GTG GCA AAG GAG GTG GAC GAG ATA CTC ACT GAA 664
 195 N   R   Q   Y   E   H   F   N   K   V   A   K   E   V   D   E   I   L   T   E   214

665 CAG GGT GGG AAG CGT ATT GTT CCC GTG GGT CTA GGA GAT GAT GAT CAA TGC ATA GAA GAT 724
 215 Q   G   G   K   R   I   V   P   V   G   L   G   D   D   D   Q   C   I   E   D   234

725 GAT TTC ACT GCG TGG CGG GAG TTG GTA TGG CCT GAA TTG GAT CAG TTG CTC CTT GAT GAA 784
 235 D   F   T   A   W   R   E   L   V   W   P   E   L   D   Q   L   L   L   D   E   254

785 AGT GAT AAA ACA TCT GTT TCT ACT CCT TAC ACT GCC ATC GTA CCA GAA TAC AGG GTA GTA 844
 255 S   D   K   T   S   V   S   T   P   Y   T   A   I   V   P   E   Y   R   V   V   274

845 TTC CAT GAT GCT ACT GAT GCA TCA CTA CAA GAC AAA AAC TGG AGC AAT GCA AAT GGC TAC 904
 275 F   H   D   A   T   D   A   S   L   Q   D   K   N   W   S   N   A   N   G   Y   294

905 ACT GTT TAC GAC GTT CAA CAC CCA TGC AGA GCC AAT GTC GTT GTA AAG AAG GAG CTT CAC 964
 295 T   V   Y   D   V   Q   H   P   C   R   A   N   V   V   V   K   K   E   L   H   314

965 ACT CCA GTA TCT GAT CGT TCT TGT ATT CAT CTG GAA TTT GAC ATT TCT GGC ACT GGG CTC 1024
 315 T   P   V   S   D   R   S   C   I   H   L   E   F   D   I   S   G   T   G   L   334

1025 ACG TAT GAA ACA GGA GAC CAT GTC GGT GTT TAC TCT GAG AAT TGT GTT GAA GTT GTC GAG 1084
 335 T   Y   E   T   G   D   H   V   G   V   Y   S   E   N   C   V   E   V   V   E   354

1083 GAA GCA GAG AGG CTA TTG GGT TAC TCA TCA GAC ACC GTT TTT TCA ATC CAT GTC GAT AAA 1144
 355 E   A   E   R   L   L   G   Y   S   S   D   T   V   F   S   I   H   V   D   K   374
```

FIG. 10b (2)

```
1145 GAG GAC GGC TCA CCC ATT AGT GGA AGC GCT CTA GCT CCT CCT TTT CCA ACT CCC TGC ACT 1204
375  E   D   G   S   P   I   S   G   S   A   L   A   P   P   F   P   T   P   C   T   394

1205 CTA AGA ACA GCA CTA ACA CGA TAC GCT GAT CTG TTG AAT TCT CCC AAG AAG GCT GCT CTG 1264
395  L   R   T   A   L   T   R   Y   A   D   L   L   N   S   P   K   K   A   A   L   414

1265 CAT GCT TTG GCT GCT TAT GCA TCC GAT CCA AAG GAA GCG GAG CGA CTA AGG TAT CTT GCG 1324
415  H   A   L   A   A   Y   A   S   D   P   K   E   A   E   R   L   R   Y   L   A   434

1325 TCT CCT GCT GGG AAG GAC GAA TAC GCC CAG TGG ATA GTA GCT AGT CAG AGA AGT CTG CTA 1384
435  S   P   A   G   K   D   E   Y   A   Q   W   I   V   A   S   Q   R   S   L   L   454

1385 GTG GTC ATG GCT GAA TTC CCA TCA GCA AAG GCT CCA ATT GGG GTT TTC TTT GCA GCA GTA 1444
455  V   V   M   A   E   F   P   S   A   K   A   P   I   G   V   F   F   A   A   V   474

1445 GCT CCT CGC TTG CTG CCA AGA TAC TAT TCT ATT TCA TCT TCC AAT AGG ATG GTA CCA TCT 1504
475  A   P   R   L   L   P   R   Y   Y   S   I   S   S   S   N   R   M   V   P   S   494

1505 AGG ATT CAT GTC ACA TGT GCA TTG GTG CAT GAA AAA ACA CCG GCA GGT CGG GTT CAC AAA 1564
495  R   I   H   V   T   C   A   L   V   H   E   K   T   P   A   G   R   V   H   K   514

1565 GGA GTG TGT TCA ACC TGG ATG AAG AAT TCT GTG TCT TTG GAA GAA AAC CAT GAT TGC AGC 1624
515  G   V   C   S   T   W   M   K   N   S   V   S   L   E   E   N   H   D   C   S   534

1625 AGC TGG GCA CCA ATC TTT GTC AGG CAA TCC AAC TTC AAA CTT CCT GCT GAT TCT ACA GTA 1684
535  S   W   A   P   I   F   V   R   Q   S   N   F   K   L   P   A   D   S   T   V   554

1685 CCA ATT ATA ATG ATT GGT CCT GGG ACT GGA TTA GCT CCC TTT AGG GGA TTC ATG CAG GAG 1744
555  P   I   I   M   I   G   P   G   T   G   L   A   P   F   R   G   F   M   Q   E   574

1745 CGA TTA GCT CTG AAG AAT TCT GGT GTA GAA TTG GGA CCC GCT ATC CTC TTC TTT GGA TGC 1804
575  R   L   A   L   K   N   S   G   V   E   L   G   P   A   I   L   F   F   G   C   594

1805 AGA AAC AGA CAG ATG GAT TAC ATA TAT GAA GAG GAG CTA AAC AAC TTT GTG AAA GAG GGA 1864
595  R   N   R   Q   M   D   Y   I   Y   E   E   E   L   N   N   F   V   K   E   G   614

1865 GCT ATC TCC GAA GTT GTT GTT GCT TTC TCA CGT GAG GGA GCT ACC AAG GAA TAC GTA CAA 1924
615  A   I   S   E   V   V   V   A   F   S   R   E   G   A   T   K   E   Y   V   Q   634

1925 CAT AAA ATG GCG GAG AAG GCT TCC TAC ATC TGG GAA ATG ATC TCT CAA GGT GCT TAT CTT 1984
635  H   K   M   A   E   K   A   S   Y   I   W   E   M   I   S   Q   G   A   Y   L   654

1985 TAT GTA TGT GGT GAT GCC AAG GGC ATG GCT AGA GAC GTA CAT CGA ACT CTC CAC ACC ATT 2044
655  Y   V   C   G   D   A   K   G   M   A   R   D   V   H   R   T   L   H   T   I   674

2045 GCC CAG GAA CAG GGA TCT TTG GAC AAC TCG AAG ACC GAA AGC TTG GTG AAG AAT CTA CAG 2104
675  A   Q   E   Q   G   S   L   D   N   S   K   T   E   S   L   V   K   N   L   Q   694

2105 ATG GAT GGA AGG TAT CTA CGT GAT GTG TGG TGA TTGgggctagagcggcc                    2154
695  M   D   G   R   Y   L   R   D   V   W   *                                      705
```

CYTOCHROME P450 REDUCTASES FROM POPPY PLANTS

CROSS-REFERENCE TO RELATED APPLICATIONS

This application is the national stage filing under 35 U.S.C. § 371 of International Application No. PCT/AU98/00705 filed Aug. 28, 1998 and published Mar. 11, 1999 as International Publication No. WO 99/11765 which in turn claims benefit under 35 U.S.C. § 119 to Australian Application Number PP8872 filed Aug. 29, 1997.

TECHNICAL FIELD

The present invention relates to production of alkaloids from poppy plants and in particular to genes encoding enzymes in the alkaloid pathway, to proteins encoded by the genes, to plants transformed or transfected with the genes and to methods of altering alkaloid content or blend of poppy plants.

INTRODUCTION

The opium poppy *Papaver somniferum* is grown under strict government control, for the production of medically useful alkaloids such as morphine and codeine. The alkaloid content of poppy straw (includes threshed poppy capsules) is the most important parameter in the efficiency of opium alkaloid production. There have been numerous attempts to increase the yield of alkaloid per ton of poppy material. The vast majority of approaches focus on improving agricultural practices and on established methods of conventional breeding in the attempt to increase cultivation efficiencies and to modifying the genotype of the opium poppy plants.

In addition to increasing the overall yield of opium alkaloids, the relative content of particular alkaloids in the poppy plants is also of considerable importance and has an impact on efficiency of processing of the plant material and the ultimate yield and cost of an alkaloid.

Usually only one of the many alkaloids that can be produced by a poppy plant is found as the predominant alkaloid. In the opium poppy this is predominantly morphine which accumulates after flowering of the plant. However, before flowering thebaine is most abundant. The reason for such bias can be explained, at least in part, by analysis of what is currently known about alkaloid metabolism in the opium poppy and its regulation.

The network of reactions, enzymes, co-factors and metabolic intermediates leading to the synthesis of alkaloids in the opium poppy constitute a complex metabolic pathway which is regulated at numerous points. There are also thought to be a number of rate limiting steps ("bottlenecks") where limitations in the availability of either substrates, co-factors or certain enzymes, determine which particular branch of the synthetic pathway is favoured and therefore the ultimate "mix" of alkaloids and the type of alkaloid which is predominantly in the plant. A class of enzymes known as cytochrome P-450 are known to be involved in the synthesis of several intermediates in the pathway. However, unlike the enzymology of mammalian cytochrome P450 enzymes, similar plant enzymes are considerably less abundant (Biochimie 1987, 69:743–752) and have been less clearly described. It is known that plant P450 enzymes are like mammalian proteins and that they are hemoproteins which have a common prosthetic group containing iron and are membrane-bound proteins found within the endoplasmic reticulum. Generally, the P450-dependent enzymes catalyse the transferral of oxygen to the substrate and effectively remove one of the atoms from an oxygen molecule and are also referred to as monooxygenases. The reactions are dependent on a range of co-factors including NADPH and a second enzyme P450 cytochrome reductase.

More particularly, in the biosynthesis of alkaloids in plants, cytochrome P-450-dependent oxidases and monooxygenases have been shown to catalyse highly regio- and stereoselective reactions. Hydroxylases and oxidases specific to alkaloid biosynthesis have been identified and characterised for the protopine, berberine, bisbenzylisoquinoline, benzophenanthridine, morphinan and monoterpenoid indole alkaloid biosynthetic pathways. The role of cytochrome P-450s in alkaloid biosynthesis is exemplified by the biosynthesis of sanguinarine in *Eschscholzia californica* (California poppy). Of the six oxidative transformations involved in the conversion of (S)-reticuline to sanguinarine, four are thought to be catalysed by cytochrome P-450-dependent enzymes.

Thus, plant cytochrome P-450-dependent enzymes, including those from the alkaloid poppy, constitute a substrate-specific class of enzymes that differs from their mammalian counterpart in the high regio- and stereospecificity as well as in the novel nature of the reactions catalysed. The enzymes involved in the alkaloid biosynthetic pathway require among other things the presence of a cytochrome P-450 reductase enzyme. Plant cytochrome P-450 reductases have been purified or enriched from *C. roseus* (1, 8) sweet potato (9), *Helianthus tuberosus* (Jerusalem artichoke) (10), *Glycine max* (soybean) cell suspension cultures (11), *Pueraria lobata* (12) and petunia flowers (13). cDNA encoding cytochrome P-450 reductase has been isolated from *Vigna radiata* (mung bean) (14), *C. roseus* (15), *H. tuberosous* (accession Z26250, Z26251), *Vicia sativa* (accession Z26252) and *Arabidopsis* (16). cDNA cloning and heterologous expression in *E. coli* of the *C. roseus* cytochrome P-450 reductase has been reported (15).

The reductase is responsible for providing electrons to the P450 and is thought to be a relatively promiscuous enzyme in that a particular reductase species will reduce a range of distinct P450s. It is also known that the cytochrome P450 enzymes are in molar excess to the level of P450 reductase. This imbalance may be a regulatory step for the reduction and therefore be rate-limiting of the cytochrome P450 activity. Although there is some promiscuity within species, available data suggests that there is poor transferability of reductases from diverged species. For example, although cytochrome P-450 reductase from insect cell culture and porcine liver was shown to transfer electrons to heterologously expressed *Berberis* berbamunine synthase, the highest turnover number was achieved with the *Berberis* reductase (7).

Notwithstanding this body of work, to date it has not been possible to establish the exact nature of the "bottlenecks" in the alkaloid metabolism pathway or to identify the key enzymes which may be responsible and which could be used to manipulate alkaloid metabolism in the opium poppy in order to achieve higher yields of alkaloids generally, and specific alkaloids in particular.

As the cost of producing poppy alkaloids is very dependent on the alkaloid content of poppy straw, it would be a major advantage if high alkaloid containing straw could be obtained rather than to attempt to increase the yield of straw. In fact, it is possible that any increase in the yield of straw may result in the relative content of alkaloid decreasing through dilution. High alkaloid-containing straw would provide efficiencies throughout the CPS ("Concentrate of Poppy Straw") production process. If high crop yields can be achieved, either less hectares of crop need be grown or the preexisting areas can be used to increase production. High yield crops would also reduce the cost of harvest, transport, drying, storage, processing and waste disposal per unit weight of alkaloid. Thus, to increase the yield of an alkaloid it would be most efficient to manipulate the plants to increase alkaloid content of the straw rather than to increase the yield of straw.

SUMMARY OF THE INVENTION

It has now been found that among the rate-limiting steps in the production of morphine in *Papaver somniferum* are the steps which depend on the cytochrome P-450 enzymes, and therefore in turn on the cytochrome P-450 reductases. This observation has led to the identification and isolation of cytochrome P-450 reductase enzymes in the alkaloid poppy, the isolation and characterisation of polynucleotides encoding the reductase enzymes, the expression of the polynucleotides encoding the reductases in eukaryotic and prokaryotic expression systems, including plant cells and transfected or transformed plants. The identification of cytochrome P-450 reductase genes and their products in poppy plants now enables methods of controlling the total alkaloid content of a plant, the ultimate "mix" of alkaloids as well as the type of predominant alkaloid synthesised by the plant. This can be achieved by alleviating the "bottlenecks" in the pathway through overexpression of the relevant reductase genes in plants transformed or transfected with a nucleotide sequence encoding an appropriate P-450 reductase enzyme.

Thus, according to a first aspect there is an isolated and purified polynucleotide encoding a cytochrome P-450 reductase enzyme from an alkaloid poppy plant, or a variant, fragment or analog thereof.

The polynucleotide may be selected from the group consisting of genomic DNA (gDNA), cDNA, or synthetic DNA. The preferred polynucleotides encoding a cytochrome P-450 reductase are selected from those shown in FIGS. 9a and 9b or fragments thereof. It will be understood however that sequences shown in the FIGS. 9a and 9b may be expressed in the absence of the native leader sequences or any of the 5' or 3' untranslated regions of the polynucleotide. Such regions of the polynucleotide may be replaced with exogenous control/regulatory sequences in order to optimise/enhance expression of the sequence in an expression system. FIGS. 10a and 10b represent examples of truncated polynucleotide sequences encoding cytochrome P-450 reductases of *P. somniferum* and *E. californica* respectively, wherein the native leader sequences have been removed in order to enhance the expression of the enzyme.

The preferred alkaloid-producing poppy plants are *Eschscholzia californica* and *Papaver somniferum*.

It will also be understood that analogues and variants of the polynucleotide encoding a cytochrome P-450 reductase from alkaloid poppy plants fall within the scope of the present invention. Such variants will still encode an enzyme with cytochrome P-450 reductase properties and may include codon substitutions or modifications which do not alter the amino acid encoded by the codon but which enable efficient expression of the polynucleotide encoding cytochrome P-450 reductase enzyme in a chose expression system. Other variants may be naturally occurring, for example allelic variants or isoforms.

According to a second aspect there is provided an isolated and purified polynucleotide having a sequence which is complementary to all or part of the sequence of a polynucleotide according to the first aspect.

Such complementary polynucleotides are useful in the present invention as probes and primers, as antisense agents or may be used in the design of other suppressive agents such as ribozymes and the like.

According to a third aspect there is provided an isolated and purified polynucleotide which codes for prokaryotic or eukaryotic expression of a cytochrome P-450 reductase enzyme from an alkaloid poppy plant, or a variant, analog or fragment thereof, wherein the polynucleotide is expressed in an environment selected from the group consisting of the extracellular environment, an intracellular membranous compartment, intracellular cytoplasmic compartment or combinations thereof.

The polynucleotide encoding a cytochrome P-450 reductase may be coupled to another nucleotide sequence which would assist or directing the expression of the reductase with respect to a particular cellular compartment or the extracellular environment.

According to a fourth aspect there is provided a recombinant DNA construct comprising the polynucleotide according to any one of first to third aspects.

Preferably the recombinant DNA construct is a viral or plasmid vector. Such a vector may direct prokaryotic or eukaryotic expression of the polynucleotide encoding a cytochrome P-450 reductase or it may prevent or reduce its expression.

According to a fifth aspect there is provided an isolated and purified cytochrome P-450 reductase enzyme, being a product of prokaryotic or eukaryotic expression of the polynucleotide of any one of first to third aspects or a DNA construct of the fourth aspect.

Variants of the cytochrome P-450 reductase enzyme which incorporate amino acid deletions, substitutions, additions or combinations thereof, are also contemplated. The variants can be advantageously prepared by introducing appropriate codon mutations, deletions, insertions or combinations thereof, into the polynucleotide encoding the P-450 reductase enzyme. Such variants will retain the properties of the P-450 reductase enzyme, either in vivo or in vitro. Other variants may be naturally occurring, for example allelic variants or isoforms.

The cytochrome P-450 reductase may be expressed in and by a variety of eukaryotic and prokaryotic cells and organisms, including bacteria, yeasts, insect cells, mammalian and other vertebrate cells, or plant cells. Preferably the expression system is a plant expression system and even more preferred is an alkaloid poppy plant. Suitable alkaloid poppy plants are *Eschscholzia californica* and *Papaver somniferum*.

For expression of cytochrome P-450 reductase activity, a fragment of the polynucleotide encoding a cytochrome P-450 reductase may be employed, such fragment encodes functionally relevant regions, motifs or domains of the reductase protein. Similarly, fragments of the P-450 reductase enzyme resulting from the recombinant expression of the polynucleotide may be used. Functionally important domains of cytochrome P-450 reductase may be represented by individual exons or may be identified as being highly conserved regions of the protein molecule. Those parts of the cytochrome P-450 reductase which are not highly conserved may have important functional properties in a particular expression system.

According to a sixth aspect there is provided a cell transformed or transfected with a polynucleotide according to any one of first to third aspects or a DNA construct according to the fourth aspect.

Cells which may be transfected or transformed with a polynucleotide encoding a cytochrome P-450 reductase are bacterial, yeast, animal or plant cells. For preference the cells are plant cells. Even more preferred are cells from an alkaloid poppy plant, such as *Eschscholzia californica* or *Papaver somniferum*.

According to a seventh aspect there is provided a method for preparing plants which overexpress a cytochrome P-450 reductase enzyme, comprising transfecting or transforming a plant cell, a plant part or a plant, with the polynucleotide according to any one of first to third aspects or a DNA construct according to the fourth aspect.

Preferably, the plants overexpressing the P-450 reductase are *Eschscholzia californica* and *Papaver somniferum*. Suitable promoters to control the expression of the P-450 reductase gene may be derived from for example cauliflower mosaic virus or subterranean clover mosaic virus. Other virus promoters may also be suitable. Further, the use of the endogenous promoter may also be appropriate in certain circumstances. Such a promoter may be co-isolated with the gDNA encoding the P-450 reductase enzyme.

According to a eighth aspect there is provided a plant transformed or transfected with a polynucleotide according to any one of first to third aspects or a DNA construct according to the fourth aspect, wherein the plant exhibits altered expression of the cytochrome P-450 reductase enzyme.

For preference, the altered expression manifests itself in overexpression of the cytochrome P-450 reductase enzyme. However, reduced expression of cytochrome P-450 reductase can also be achieved if the plant is transformed or transfected with a polynucleotide which is complementary to the polynucleotide encoding the reductase.

Even more preferably, the transformed or transfected plant is an alkaloid poppy plant, wherein the plant has a higher or different alkaloid content when compared to a plant which has not been so transformed or transfected.

Preferably the transformed or transfected plants having higher or different alkaloid content are selected from *Eschscholzia californica* and *Papaver somniferum*. Even more preferred is *Papaver somniferum*.

According to a ninth aspect there is provided a method of altering the yield or type of alkaloid in a plant comprising transforming or transfecting a plant cell, a plant part or a plant with a polynucleotide encoding a cytochrome P-450 reductase enzyme or a variant, analog or fragment thereof, or with a polynucleotide which binds under stringent conditions to the polynucleotide encoding said enzyme.

According to a tenth aspect there is provided a method of increasing the yield of alkaloid in a plant comprising transforming or transfecting a plant cell, a plant part or a plant with a polynucleotide encoding a cytochrome P-450 reductase enzyme or a variant, analog or fragment thereof, wherein the enzyme is overexpressed in said plant.

According to a eleventh aspect there is provided a method of altering type or blend of alkaloid in a plant comprising transforming or transfecting a plant cell, a plant part or a plant with a polynucleotide encoding a cytochrome P-450 reductase enzyme or a variant, analog or fragment thereof, or with a polynucleotide which binds under stringent conditions to the polynucleotide encoding said enzyme.

According to a twelfth aspect there is provided a stand of stably reproducing alkaloid poppies transformed or transfected with a polynucleotide according to any one first to third aspects or a DNA construct according to the fourth aspect, having altered expression of the cytochrome P-450 reductase enzyme.

According to a thirteenth aspect there is provided a stand of stably reproducing alkaloid poppies transformed or transfected with a polynucleotide according to any one of first to third aspects or a DNA construct according to the fourth aspect, having a higher or different alkaloid content when compared to a plant which has not been so transformed or transfected.

Preferably the stably reproducing alkaloid poppy is *Papaver somniferum*.

According to a fourteenth aspect there is provided straw of stably reproducing poppies according twelfth or thirteenth aspect, having a higher or different alkaloid content when compared to the straw obtained from an alkaloid poppy which has not been transformed or transfected.

According to a fifteenth aspect there is provided a concentrate of straw according to the fourteenth aspect, having a higher or different alkaloid content when compared to the concentrate of straw obtained from an alkaloid poppy which has not been transformed or transfected.

According to a sixteenth aspect there is provided an alkaloid when isolated from the straw according to fourteenth aspect or the concentrate according to the fifteenth aspect.

According to a seventeenth aspect there is provided a method for the production of poppy plant alkaloids, comprising the steps of;
  a) harvesting capsules of an alkaloid poppy plant transformed or transfected with a polynucleotide according to any one of first to third aspects or a DNA construct according to the fourth aspect, to produce a straw where the poppy plant is such a plant that the straw has a higher or different alkaloid content when compared to the straw obtained from a poppy plant which has not been transformed or transfected.
  b) chemically extracting the alkaloids from the straw.

According to an eighteenth aspect there is provided a method for the production of poppy alkaloids, comprising the steps of;
  a) collecting and drying the latex of the immature capsules of an alkaloid poppy plant transformed or transfected with a polynucleotide according to any one of first to third aspects or a DNA construct according to the fourth aspect, to produce opium where the poppy plant is such a plant that the opium has a higher or different alkaloid content when compared to the opium obtained from a poppy plant which has not been transformed or transfected.

b) chemically extracting the alkaloids from the opium.

For preference the alkaloid is morphine, codeine, oripavine or thebaine, but it will be understood that other intermediates in the alkaloid metabolic pathway are also within the scope of the present invention, as are mixtures of alkaloids.

Unless the context clearly requires otherwise, throughout the description and the claims, the words 'comprise', 'comprising', and the like are to be construed in an inclusive as opposed to an exclusive or exhaustive sense; that is to say, in the sense of "including, but not limited to".

BRIEF DESCRIPTION OF FIGURES

FIG. 2. Amino acid sequences of seven endoproteinase Lys-C-generated peptides of the cytochrome P-450 reductase from *P. somniferum* cell suspension cultures. Peptide 1 is SEQ ID NO: 1, Peptide 2 is SEQ ID NO: 2, Peptide 2' is SEQ ID NO: 3, Peptide 3 is SEQ ID NO: 4, Peptide 3' is SEQ ID NO: 5, Peptide 4 is SEQ ID NO: 6, Peptide 5 is SEQ ID NO: 7, Peptide 6 is SEQ ID NO: 8, and Peptide 7 is SEQ ID NO: 9.

FIG. 3. Partial amino acid sequence comparison of plant cytochrome P-450 reductases. The shaded areas and arrows indicate the position and direction of the regions used for PCR oligodeoxynucleotide primer design. *Arabidopsis thaliana* is SEQ ID NO: 20, *Catharanthus roseus* is SEQ ID NO: 21, *Helianthus tuberosus* is SEQ ID NO: 22, *Vigna radiata* is SEQ ID NO: 23 and *Vicia sativa* is SEQ ID NO: 24.

FIG. 5. Comparison of the amino acid sequences of the cytochrome P-450 reductase from *P. somniferum* and from *E. californica*. Top sequence, *E. californica*, SEQ ID NO: 25; bottom sequence, *P. somniferum*, SEQ ID NO: 26; *, amino acid identity.

FIG. 6. Nucleotide sequences of cDNA from (a) *P. somniferum*, SEQ ID NO: 10 and (b) *E. californica*, SEQ ID NO: 11.

FIG. 9. Amino acid sequences of (a) *P. somniferum*, SEQ ID NO: 12 and SEQ ID NO: 13 and (b) *E. californica*, SEQ ID NO: 14 and SEQ ID NO: 15 predicted from their respective cDNA nucleotide sequences. The start and stop codons are depicted in bold.

FIG. 10. cDNA nucleotide sequences and their predicted amino acid sequences, of fragments subcloned into an expression vector: (a) *P. somniferum*, SEQ ID NO: 16 and SEQ ID NO: 17 and (b) *E. californica*. Both sequences are truncated versions of sequences represented in FIGS. 9a and 9b, lacking the leader sequences. Extra vector sequences/restriction sites derived during subcloning are shown in lowercase and the cDNA in uppercase.

DETAILED DESCRIPTION OF THE PREFERRED EMBODIMENTS

Figure 1:
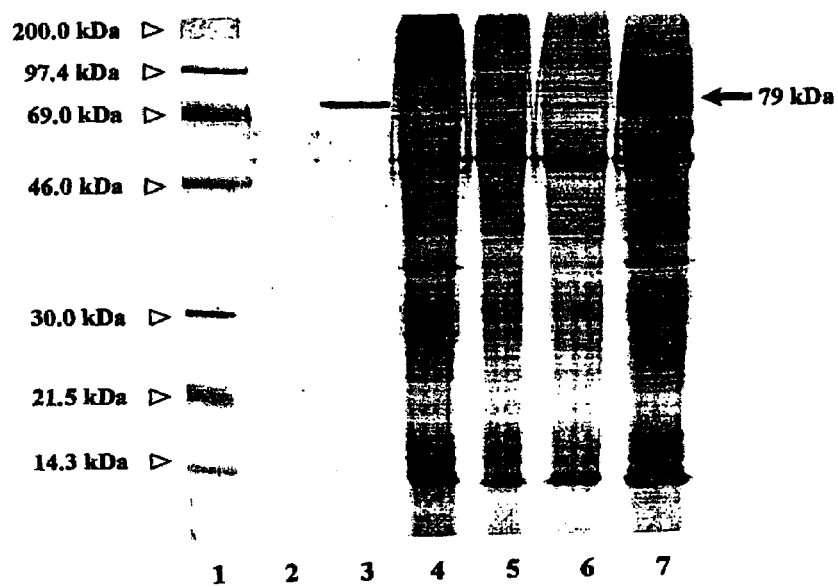
FIG. 1. SDS-PAGE analysis of fractions from the purification of cytochrome P-450 reductase from *P. somniferum* cell suspension cultures. Protein bands were visualised by silver staining. Lane 1, protein standards; lane 2, affinity chromatography elution buffer without protein: lane 3, 1 µg protein from the 2',5'-ADP Sepharose 4B eluate after dialysis; lane 4, 4 µg microsomal protein; lanes 5, 6, 4 µg solubilized microsomal protein; lane 7, 4 µg protein from the DEAE cellulose eluate.

The details of the metabolic pathway leading to synthesis of opium alkaloids in the opium poppy, *Papaver somniferum*, part of which is depicted in Scheme I. Typically, the P450 enzyme exists in a 15–20 fold excess as compared to the reductase level and as there is approximately a 6:1 dependence between the two enzymes, it is feasible that the reductase levels are limiting the rate of the cytochrome P450 enzyme. By supplying plant tissue with radiolabeled compounds and following the accumulation of radioactivity in the various intermediates in the pathway it was shown that addition of radiolabel (labelled reticuline, salutaridinol) before thebaine results in accumulation of radioactivity at thebaine. Addition of radiolabeled compounds after thebaine result in the accumulation of radioactivity at codeine.

Oripavine is an intermediate from a second route of conversion from thebaine to morphine. It is thought that thebaine is converted to oripivine by the same 3 demethylase that converts codeine to morphinone. The slow modification of the isotopic oripavine is probably due to the rate limitation of the 6 demethylase.

With the assistance of such experiments it has now been found that among the rate-limiting steps in the production of morphine in *Papaver somniferum* are the steps which depend on the reduction of cytochrome P-450 by the cytochrome P-450 reductases.

Thus the following steps are known or suspected to be catalysed by P-450 enzymes which are rate limiting:

1 (R)-reticuline→salutaridine 2 thebaine→neopinone→codeinone 3 codeine→morphine

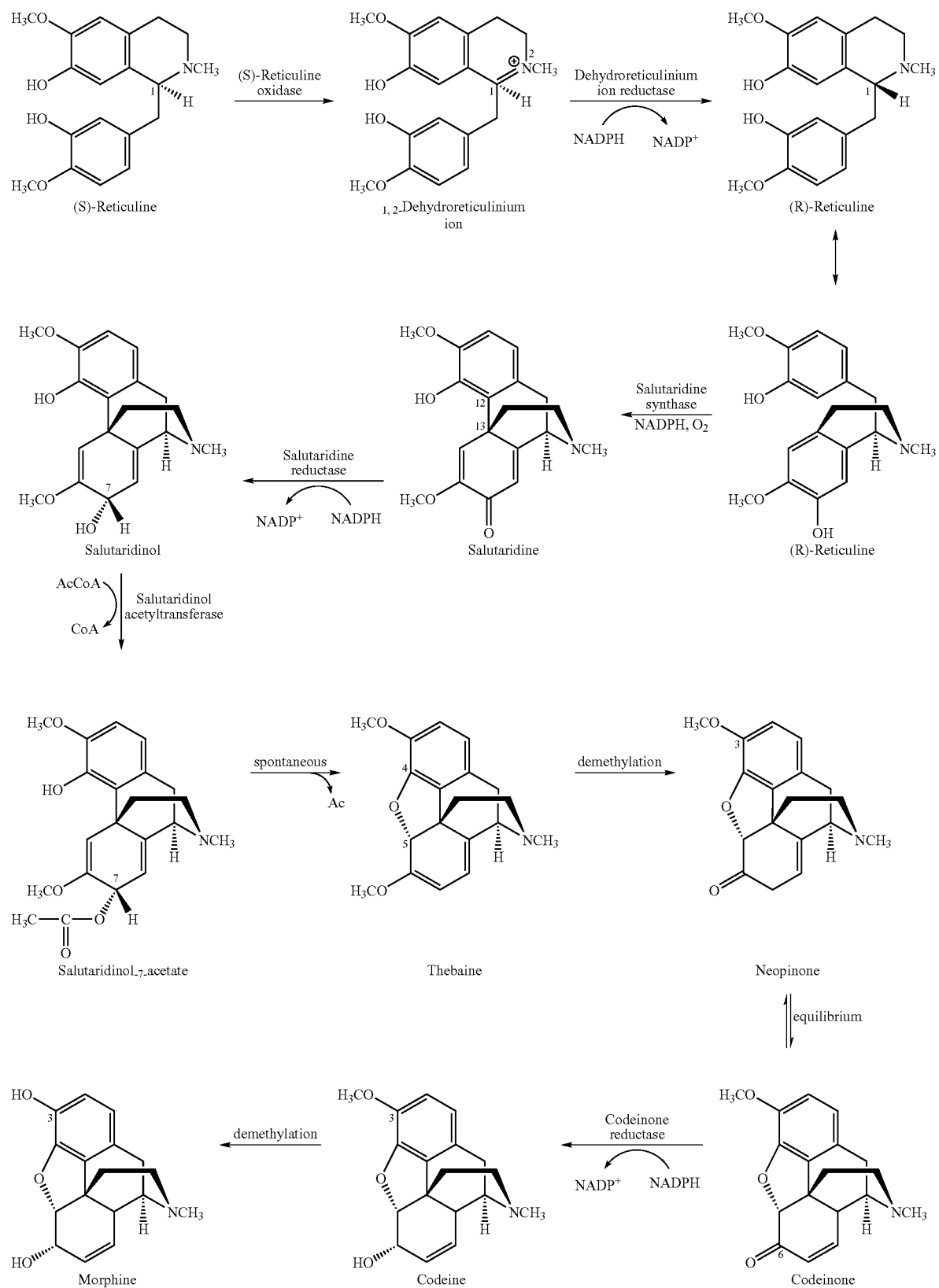

The importance of cytochrome P-450 in alkaloid biosynthesis is also exemplified by the biosynthesis of sanguinarine in *Eschscholzia californica* (California poppy). This biosynthetic pathway is shown in Scheme II.

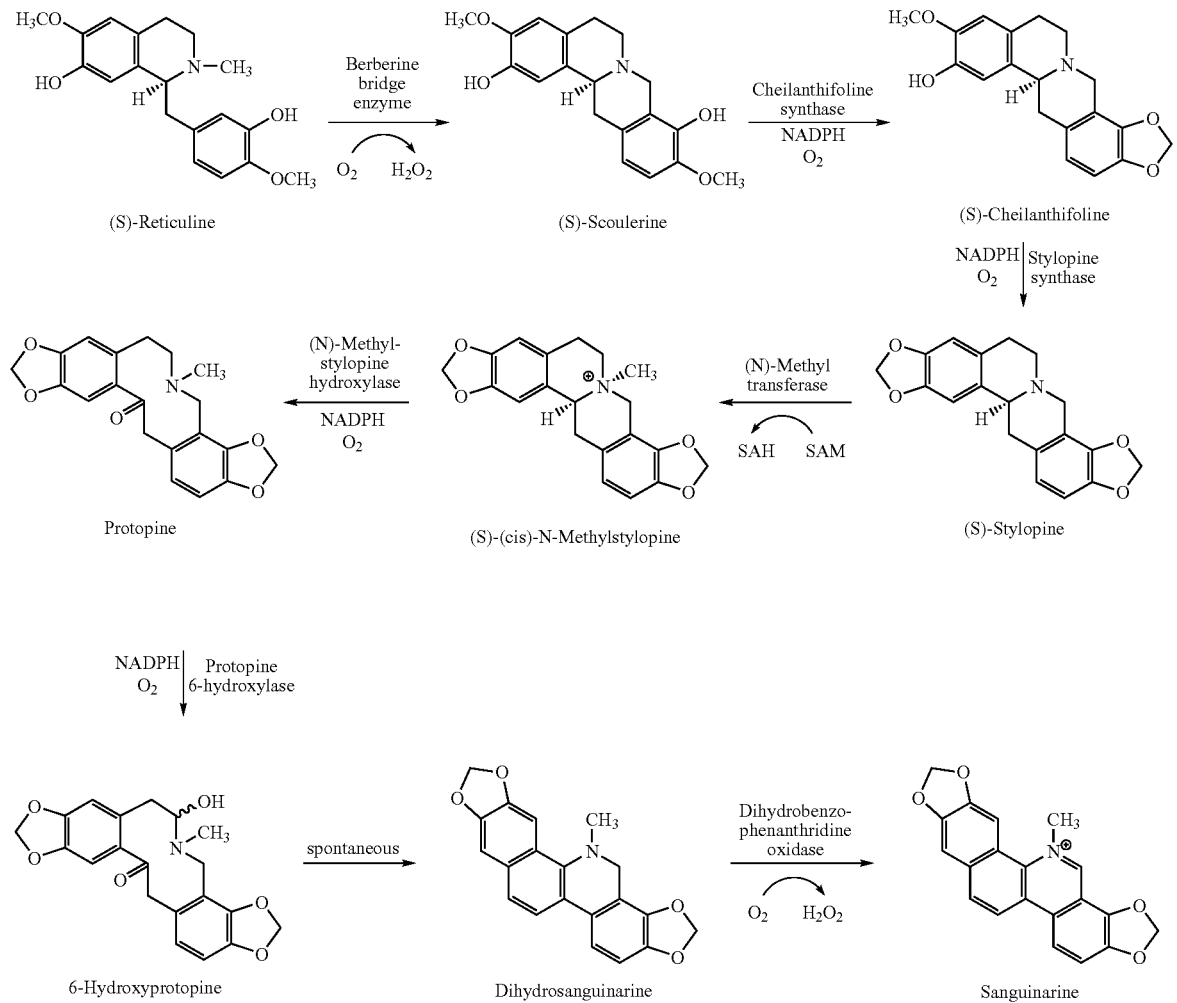

The present invention provides by way of example the sequence of the P-450 reductase enzyme genes from two poppy species, the opium poppy *Papaver somniferum* and the Californian poppy *Eschscholzia californica*. The sequence information has been shown to code for the enzymes by expression in a heterologous expression system followed by biochemical characterisation. These studies have also shown that the alteration of the ratio and species of reductase will significantly alter the interaction of the cytochrome P-450 with its substrate suggesting a lack of tolerance for general interchange of reductase genes.

The over-expression of the P-450 reductase gene in an alkaloid producing plant will alleviate the rate-limitation of the P450 by increasing the rate of reduction of the active P-450 enzyme. In brief, controlling the reductase should control the P-450 cytochrome.

The information on the protein coding region of cytochrome P-450 reductase enzymes may be applied to increase yields of alkaloids in the poppy plant as follows:

1) obtain the gDNA or cDNA sequence of the gene from the target plant and a closely related plant.
2) sub-clone the gDNA or cDNA into a plasmid vector that contains the following:
   a promoter suitable for overexpression of the cDNA in poppy, for example a promoter derived from the cauliflower mosaic virus or the subterranean clover mosaic virus.
   a selectable marker linked to a different promoter to facilitate the selection of transformants. Marker could be a dominant marker such as a herbicide resistance gene or an antibiotic resistance gene.

suitable selectable markers and replication origins for maintenance of the plasmid in bacteria suitable sequences to facilitate mobilisation of the plasmid by *Agrobacterium tumefaciens*-mediated transformation.

3) transform a suitable strain of *A. tumefaciens* and then co-cultivate the bacteria with suitable samples of plant tissue such as callus, embryonic tissue or hypocotyl tissue.

4) place treated tissue on selectable media and provide appropriate media to promote differentiation and plant re-generation.

5) characterise candidate plants by Southern and Northern blotting to confirm integration of gene and expression in appropriate tissues 6) self-pollinate transformed plants, analyse segregants to identify hemizygotes and 30 homozygotes 7) analyse biochemistry of transgenic plants.

Isotope labelling can be used to identify bottlenecks and HPLC analysis will determine levels of alkaloids.

In order to develop optimised convenient heterologous expression systems for the cytochrome P-450-dependent oxidases of select isoquinoline alkaloid-producing plant species, facile PCR-based method have been developed with which to clone cytochrome P-450 reductase and express the enzyme in yeast and insect cell culture as initial expression systems.

The invention will now be described with reference to specific examples.

EXAMPLES

Example 1

Enzyme Purification and Amino Acid Sequencing

Plant cell cultures. Cell suspension cultures of *P. somniferum* and *E. californica* were routinely grown in 1-liter conical flasks containing 400 mL of Linsmaier-Skoog medium (17) over 7 days at 23° C. on a gyratory shaker (100 rpm) in diffuse light (750 lux). Elicitation of *E. californica* cell suspension cultures was achieved by the aseptic addition of methyl jasmonate to a final concentration of 100 μM to the medium (18).

Purification and sequence analysis. Cells were harvested from seven-day-old suspension cultures of *P. somniferum* by vacuum filtration, immediately shock frozen and stored at −20° C. All of the following operations were carried out at 4° C. 500 g frozen tissue were then homogenised with a mortar and pestle in 1 liter 0.1 M tricine/NaOH, pH 7.5 containing 15 mM thioglycolic acid. Cell debris was removed by centrifugation at 10,000× g, 30 min. The supernatant was filtered through four layers of cheesecloth and the microsomes were then isolated by $MgCl_2$ precipitation according to (19). In a typical preparation, 500 g fresh weight of cells yielded 8–10 mg/mL microsomal protein. Microsomal protein was solubilized as follows. 2 mg CHAPS (3[(3-cholamidopropyl)dimethyl-ammonio]-1-propane-sulfonate, Roth) per mg microsomal protein was prepared in 1 mL of 0.1 M tricine/NaOH, pH 7.5 containing 15 mM thioglycolic acid. This solution was added dropwise to the microsomal suspension. 2% (v/v) Emulgen 911 (Kao Corporation) was then added and the solution slowly stirred for 1 h. Membrane fragments were removed by centrifugation at 105,000× g for 60 min. The total activity in the solubilized microsomes was assigned the value 100%. The solubilized cytochrome P-450 reductase was then purified to electrophoretic homogeneity according to (20). In this manner, 50 μg cytochrome P-450 reductase was purified from 8 kg *P. somniferum* cell suspension culture in 97% yield.

The purified enzyme preparation was subjected to SDS/PAGE to remove traces of Emulgen 911 and CHAPS, and the Coomassie brilliant blue R-250-visualized band representing the cytochrome P-450 reductase was digested in situ with endoproteinase Lys-C as reported in (21). The peptide mixture thereby obtained was resolved by reversed phase HPLC [column, Merck Lichrospher RP18; 5 μm (4×125 mm); solvent system, (A) 0.1% trifluoroacetic acid, (B) 0.1% trifluoroacetic acid/60% acetonitrile; gradient of 1% per min; flow rate of 1 mL/min] with detection at 206 nm. The scheme for the purification of the cytochrome P-450 reductase is given in Table I.

TABLE I

Purification of Cytochrome P-450 Reductase from *P. somniferum* Cell Suspension Cultures

| Purification Step | Total protein (mg) | Total activity (nkatal) | Specific activity (nkatal/mg) | Purification factor (fold) | Yield (%) |
|---|---|---|---|---|---|
| Microsomes | 308 | 59 | 0.2 | — | — |
| Solubilized microsomes | 244 | 71 | 0.3 | 1 | 100 |
| DEAE Cellulose | 21 | 71 | 3.4 | 11 | 100 |
| 2',5'-ADP Sepharose 4B | 0.05 | 47 | 927 | 3100 | 66 |
| Dialysis | 0.05 | 69 | 1385 | 4600 | 97 |

Following this facile purification procedure (20), 50 μg of enzyme could be purified to near electrophoretic homogeneity from 8 kg fresh weight of cell suspension culture with minimal loss of activity. Gel electrophoretic analysis of aliquots of the purification steps suggest that there may be two isoforms of the cytochrome P-450 reductase in *P. somniferum* as there were two protein bands present in the 2',5'-ADP Sepharose 4B eluate at 80 kDa (FIG. 1). To further test the possible presence of isoforms, 10 μg protein from the 2',5'-ADP Sepharose 4B eluate was subjected to native polyacrylamide gel electrophoresis, the two closely migrating protein bands were eluted and both tested positive for cytochrome c reduction. These two isozymes could not be chromatographically resolved and were therefore characterised together.

The purified reductase exhibited a pH optimum at 8.0 in 0.5 M Tricine buffer. The optimal molarity range of the Tricine buffer was determined to be 250–500 mM. At 100 mM and at 1 M Tricine, the activity declined to 21% and 77%, respectively. The $K_m$ value for cytochrome c was 8.3 μM and that for the cofactor NADPH was 4.2 μM. The distribution of the cytochrome P-450 reductase in a 3-month-old *P. somniferum* plant is given in Table II.

TABLE II

Distribution of Cytochrome P-450 Reductase Activity in a 3-Month-Old *P. somniferum* Plant

| Plant part | Specific activity (pkatal/g dry weight) | Specific activity (pkatal/mg protein) |
|---|---|---|
| Capsule | 2700 | 660 |
| stem | 2000 | 930 |
| Leaf | 840 | 390 |
| Root | 670 | 740 |

On a dry weight basis, the highest activity is present in the capsule.

Microsequencing was accomplished with an Applied Biosystems model 470 gas5 phase sequencer. The amino acid sequence of seven endoproteinase Lys-C-generated peptides was determined on the mixture of both isozymes (FIG. 2). A comparison of these amino acid sequences with those available for plant cytochrome P-450 reductases in the GenBank/EMBL sequence database allowed the relative positioning of the seven internal peptides due to high sequence homology. This also served as supportive evidence that the isozymes that were purified were indeed cytochrome P-450 reductases.

Example 2

Generation of Partial cDNAs from *P. somniferum* and *E. californica*.

Optimised PCR primers were then designed based on highly homologous sites on both the amino acid and nucleotide levels in the plant cytochrome P-450 reductase sequence comparison (FIG. 3). The precise sequence of the primers used for the first round of PCR was:

```
5'-CA ITI CII CCT CCT TTC CC-3'      SEQ ID NO: 27
                                      and
          T                           SEQ ID NO: 28

3'-ACC TAC TTC TTA CGI CAA GG-5'.    SEQ ID NO: 29

C       TGC                  SEQ ID NO: 30
```

Polymerase chain reaction (PCR) generated partial cDNAs encoding cytochrome P-450 reductases from *P. somniferum* and *E. californica* were produced by PCR using cDNA produced by reverse transcription of total RNA isolated from 3 to 5-day-old suspension cultured cells. DNA amplification was performed under the following conditions: 5 cycles of 94° C., 30 sec; 45° C., 1 min; 72° C., 1 min; 25 cycles of 94° C., 30 sec; 55° C., 30 sec, 72° C., 1 min. At the end of 30 cycles, the reaction mixtures were incubated for an additional 5 min at 72° C. prior to cooling to 4° C. The amplified DNA was then resolved by agarose gel electrophoresis, the bands of approximately the correct size were isolated and subcloned into pGEM-T (Promega) prior to nucleotide sequence determination.

Resolution of this first PCR experiment by agarose gel electrophoresis revealed a mixture of DNA products in the expected range of 400–450 bp. The bands in this size range were eluted from the gel and used as template for nested PCR with the following primers:

```
5'-CA ITI CII CCT CCT TTC CC-3'        SEQ ID NO: 27 and

T                             SEQ ID NO: 28

3'-AAA CGI CGI TAI CGI GGI GCI IGI GTT GG-5'   SEQ ID NO: 31

G                    C             SEQ ID NO: 32
```

The result from the nested PCR was a single DNA band with the expected size of 288 bp. The translation of the nucleotide sequence of this PCR product indicated that it was indeed encoding a cytochrome P-450 reductase. This 288 bp PCR-generated partial cDNA was then used as hybridisation probe to screen an amplified *P. somniferum* cell suspension culture cDNA library. In this manner, from a total of 300,000 clones screened, two positive clones were isolated. Of these two positive clones, one was determine to be full-length by a restriction endonuclease analysis. The nucleotide sequence of this full-length cDNA clone was then determined for both strands. The reading frame coded for 684 amino acids corresponding to a relative molecular mass of 77.5 kDa.

Figure 4:
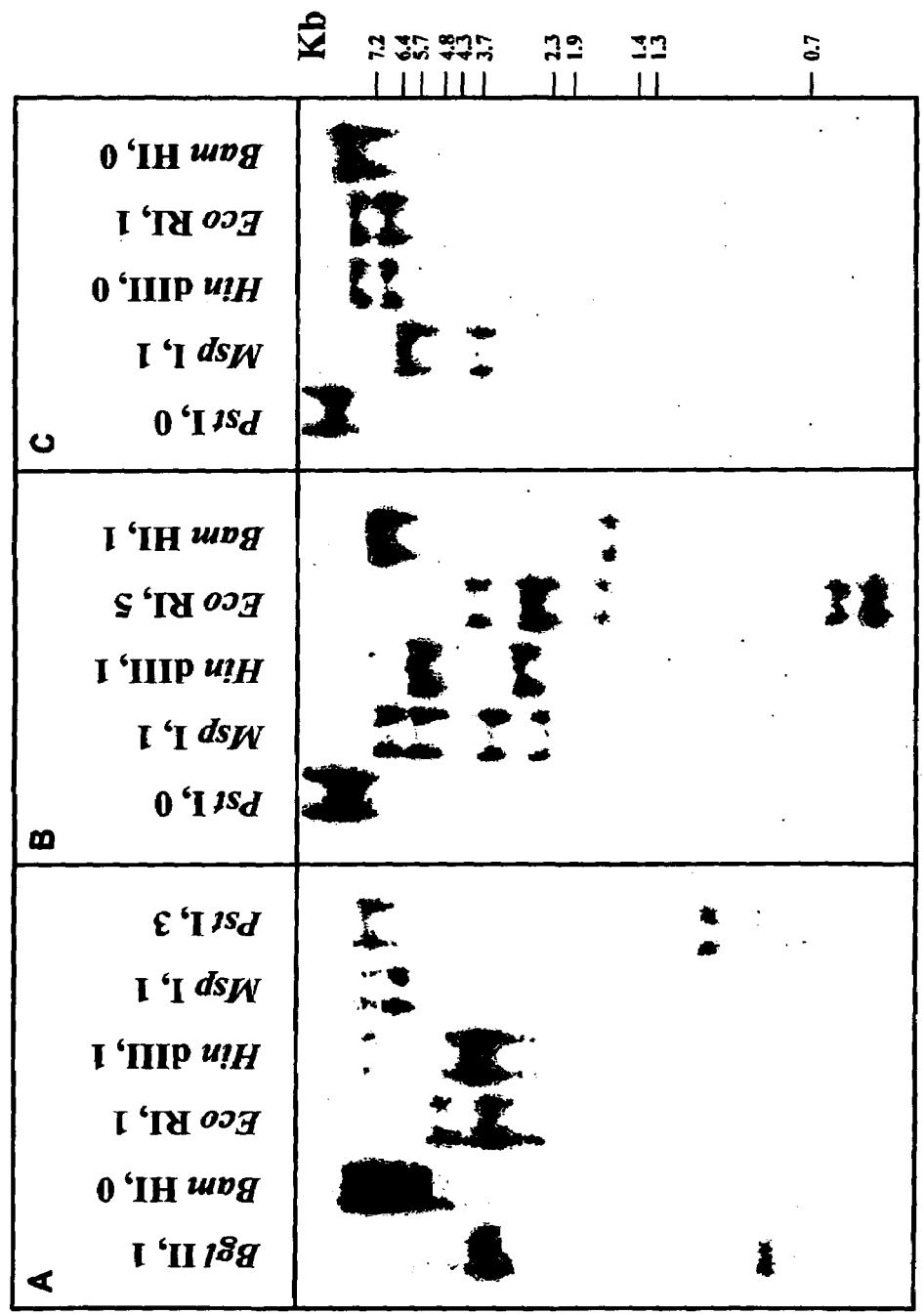
FIG. 4. Genomic DNA gel blot analysis of (A) *P. somniferum* hybridized to the *P. somniferum* full-length cDNA and (B) *E. californica* hybridzed to the *E. californica* full-length cDNA and to (C) the 288 bp PCR fragment corresponding to the second isoform. The numbers following the restriction enzyme names indicate the number of recognition sites that occur in the reading frame. For the second *E. californica* isoform, this is known only over a 288 bp region.

An identical PCR-based approached was also carried out with RNA isolated from methyl jasmonate-induced *E. californica* cell suspension cultures (26). Nucleotide sequence determination of the 288 bp DNA fragment indicated that in *E. californica* one cytochrome P-450 reductase form is present. However, screening of 400,000 clones of a primary cDNA library prepared from RNA isolated from methyl jasmonate-induced *E. californica* cell suspension cultures resulted in the isolation of one partial and one full-length clone, both of which encoded a second isoform. The nucleotide sequence of this full-length cDNA clone was then determined for both strands. The reading frame encoded 705 amino acids that corresponded to a relative molecular mass of 78.7 kDa. RNA gel blot analysis indicated that this isoform gene is weakly induced two-fold by treatment of the cell cultures with methyl jasmonate. Genomic DNA gel blot analysis of each reductase indicates that one gene encodes each isoform in *E. californica* and that one gene also encodes the cloned isoform in *P. somniferum* (FIG. 4).

The overall sequence homology of the cytochrome P-450 reductase from *P. somniferum* and that from *E. californica* is 63% identity at the nucleotide level and 69% identity at the amino acid level (FIG. 5). This compares to an overall sequence identity to other plant cytochrome P-450 reductases of approximately 50% at both the nucleotide and amino acid levels.

Nucleotide sequence determination. The entire nucleotide sequence on both DNA strands of full-length cDNA clones in pBluescript was determined by dideoxy cycle sequencing using internal DNA sequences for the design of deoxyoligonucleotides as sequencing primers. Nucleotide sequences of cDNAs of *P. somniferum* and *E. californica* are given in FIGS. 6A and 6B, respectively.

Alternative approaches. cDNA can also be prepared by isolating RNA from either plant cell suspension cultures or from different material, according to a method using LiCl precipitation of ribonucleic acid as described in "Current Protocols in Molecular Biology" Ausubel F M, Brent R, Kingston R E, Moore D D, Seidman J G, Smith J A, Struhl K, eds John Wiley & Sons, Inc. New York (1987). mRNA was then isolated from the total RNA using either an oligo dT cellulose column or oligo dT beads (Oligotex beads, QIAGEN) according to the manufacturers instructions. The cDNA libraries were prepared from mRNA with cDNA and lambda ZAP kits from Stratagen (La Jolla, Calif., USA), according to the manufacturers instructions.

Example 3 cDNA Isolation and Heterologous Expression of Cytochrome P-450 Reductase in *Saccharomyces cerevisiae* cDNA clones encoding the *Papaver* and *Eschscholzia* cytochrome P-450 reductases were isolated by screening of cDNA libraries prepared in either 1-ZAP II or Uni-ZAP XR (Stratagene) using the partial clones generated by PCR as hybridization probe. The clones that yielded positive results through a third screening were converted to pBluescript KS (+) by excision. After determination of the nucleotide sequence on both strands, the full length reading frame, free of the 5'- and 3'-flanking sequences, was generated by PCR using either Taq DNA polymerase (Perkin Elmer) and was subcloned into pGEM-T (Promega) or Pfu DNA polymerase and was subcloned into pCR-Script SK (+) (Stratagene).

The *P. somniferum* cytochrome P-450 reductase cDNA in pGEM-T, designated pGEM-T/PsoCPR, was digested with the restriction endonucleases Not I and Hin dIII and the 2096 bp fragment was ligated into Not I/Hin dIII digested pYES2 (autonomously replicating yeast expression vector from Invitrogen) to produce the expression plasmid pYES2/PsoCPR1. This particular construction had 27 bp of a noncoding region upstream from the AUG start codon. This was reduced to 6 bp by digestion of pYES2/PsoCPR1 with Hin dIII and Cla I. This 55 bp restriction fragment was then replaced by ligation with a synthetic DNA adaptor of a sequence that replaced the reading frame from the internal Cla I site through the start codon, which was immediately preceded by a Hin dIII recognition sequence. The resulting construct was termed pYES2/PsoCPR11.

The *E. californica* cytochrome P-450 reductase cDNA in pGEM-T, designated pGEM-T/EcaCPR, was digested with the restriction endonucleases Sal I and Not I and the 2289 bp fragment was ligated into Sal I/Not I digested pGEM-9Zf (−) (Promega). pGEM-9Zf/EcaCPR was then digested with Sst I and Not I and the 2292 bp fragment was ligated into Sst I/Not I digested pYES2 to produce the expression plasmid pYES2/EcaCPR1. The noncoding sequences upstream of the start codon were minimized by digestion with Sma I and Eco ICR1 and the vector recircularized by bluntend ligation (plasmid termed pYES2/EcaCPRII). These autonomously replicating expression plasmids were then introduced into the *Saccharomyces cerevisiae* strain INVSC1 under uracil selection.

Figure 7:
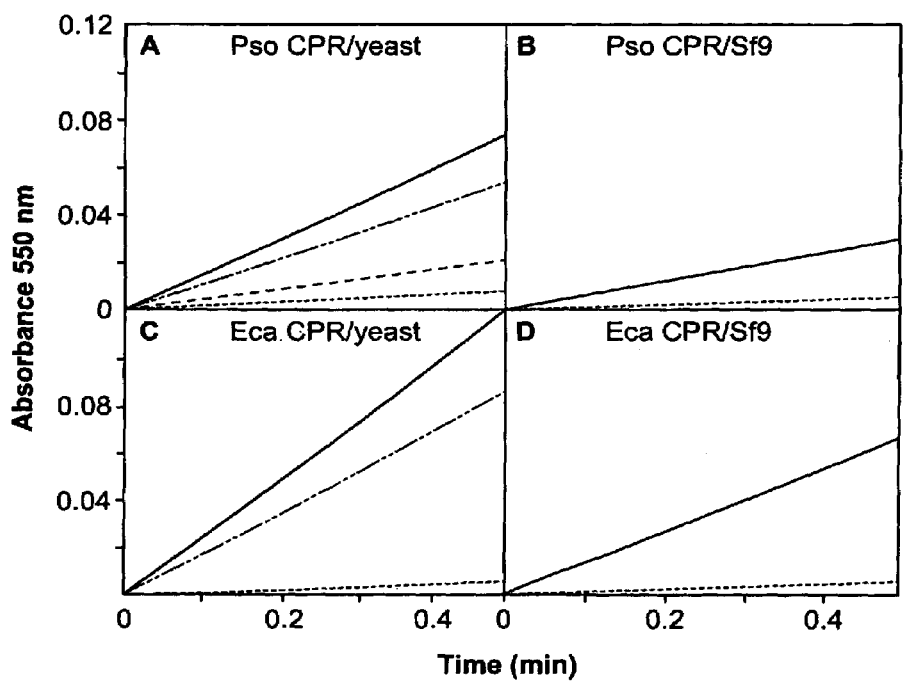
FIG. 7. Functional expression of cytochrome P-450 reductases in yeast and insect cell culture. (A) Expression of pYES2/PsoCPRI (___), pRS405/PsoCPRII (.......), pYES2/PsoCP (.......), control (.......); (B) pFastBac/PsoCPRII (___), control (.......); (C) pYES2/EcaCPRII (___), pRS405/EcaCPRII (.......), control (.......); (D) pFastBac/EcaCPRII (___), control (.......). Pso CPR, *P. somniferum* cytochrome P-450 reductase; Eca CPR, *E. californica* cytochrome P-450 reductase; Sf9, *S. frugiperda* Sf9 cell culture.
Figure 8A:
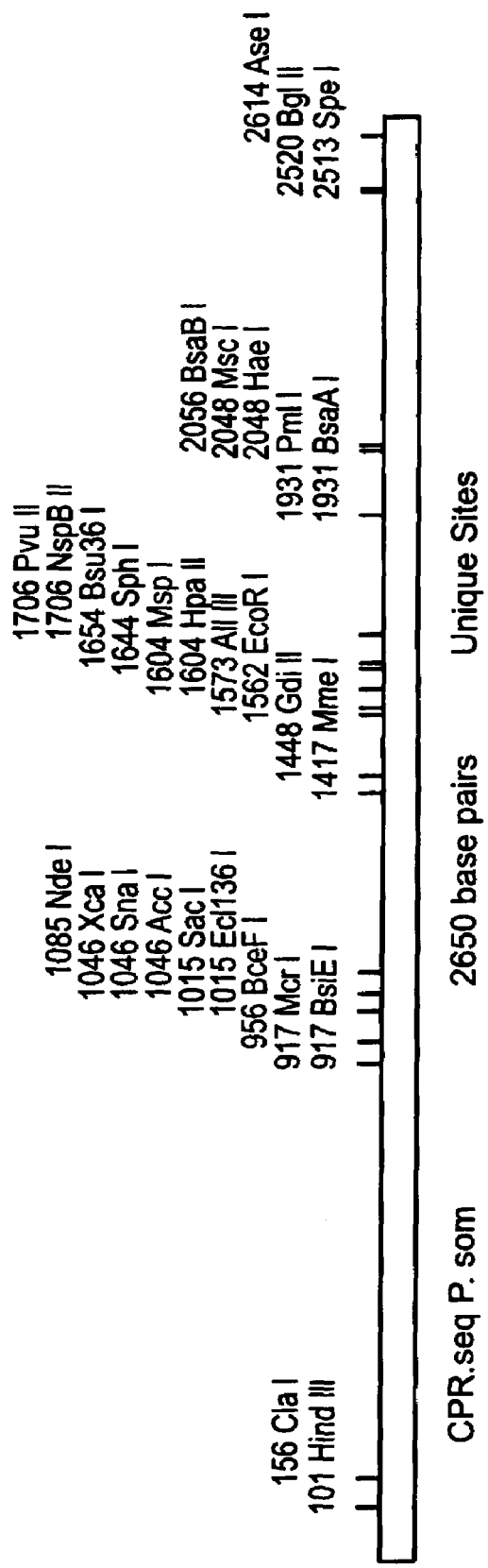
FIG. 8. Restriction enzyme map (unique sites) for cDNA sequences of (a) *P. somniferum*, and (b) *E. californica*.
Figure 8B:
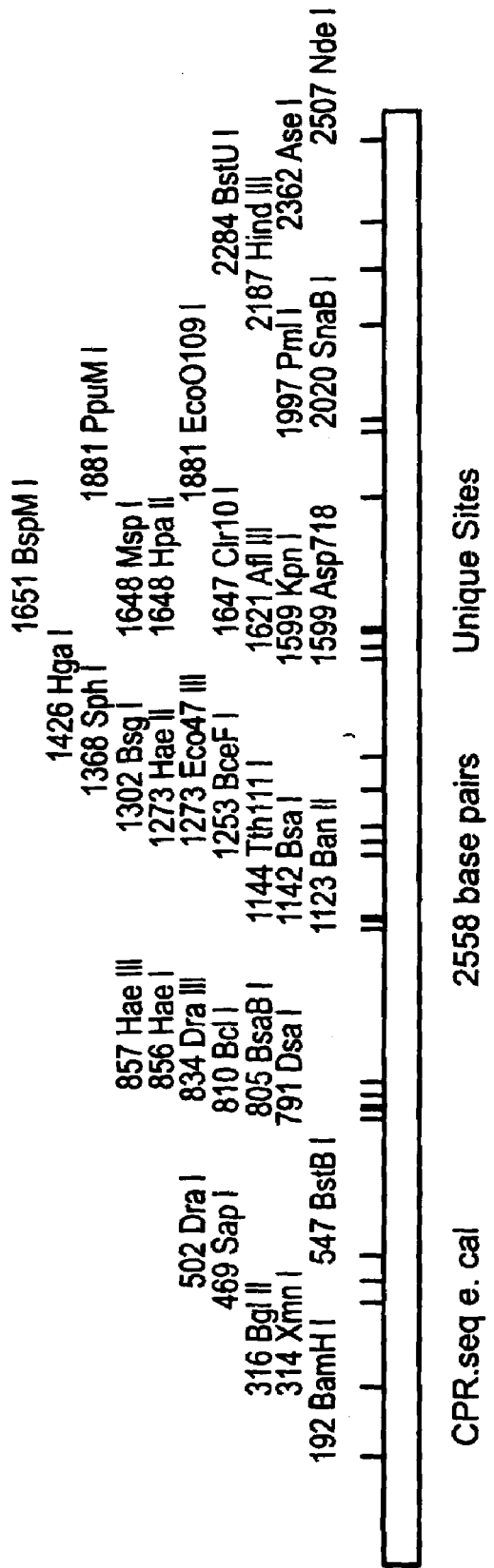

Expression of the vector pYES2/PsoCPR1 containing 27 noncoding nucleotides upstream of the start codon resulted in increased enzyme activity that was 2.6-fold greater than the yeast endogenous reductase (FIG. 7A). Shortening of this noncoding sequence to 6 bp in vector pYES2/PsoCPRII resulted in 9-fold greater enzyme activity than in the control yeast strain containing only the vector pYES2. Expression using the integrative yeast vector pRS405 was also investigated for the eventual possible heterologous co-expression of both a plant cytochrome P-450 reductase and a plant oxidase in yeast. Expression of the vector pRS405/PsoCPRII, in which transcription of the *P. somniferum* cytochrome P-450 reductase was also driven by the GAL1 gene promoter, resulted in 67% of the enzyme activity compared to the autonomously replicating vector pYES2/PsoCPRII.

Expression of pYES2/EcaCPRII and of pRS405/EcaCPRII resulted in a 15-fold and 10-fold increase in activity over the endogenous yeast reductase, respectively (FIG. 7C).

The *P. somniferum* cytochrome P-450 reductase reading frame downstream from the GAL 1 promoter was generated by PCR from pYES2/PsoCPRII. The 2598 bp PCR product was ligated into pCRScript and then excised by digestion with Not I and Sal I. This 2669 bp Not I/Sal I fragment was ligated into the Not II/Sal I digested yeast integrative expression vector pRS405 (Stratagene).

The *E. californica* cytochrome P-450 reductase reading frame downstream from the GAL 1 promoter was introduced into the yeast integrative expression vector pRS405 by digestion of pYES2/EcaCPRII with Pst I and Not I and the 2835 bp fragment was ligated into Pst I/Not I digested vector. The integrative expression plasmids pRS405/PsoCPRII and pRS405/EcaCPRII were then introduced into the *S. cerevisiae* strain INVSC1 under leucine selection.

Yeast microsomes were isolated according to either (22) or (23) and the presence cytochrome P-450 reductase was measured as the ability to reduce cytochrome c (24).

Example 4

Heterologous Expression of Cytochrome P-450 Reductase in *Spodoptera frugiperda* Sf9 Cells The *P. somniferum* cytochrome P-450 reductase cDNA construct pYES2/PsoCPRII was digested with Hin dIII and Xba I and the resultant 2096 bp fragment was ligated into Hin dIII/Xba I digested pGEM-7Zf (+) (Promega). pGEM7Zf/PsoCPRII was then digested with Bam HI and Xho I and the 2090 bp fragment was ligated into Bam HI/Xho I digested pFastBac1 (Life Technologies).

The *E. californica* cytochrome P-450 reductase clone pGEM-T/EcaCPRII was digested with the restriction endonucleases Sma I and Not I and the 2251 bp fragment was ligated into pFastBac1 that had been digested first with Bam HI, then with Pfu DNA polymerase to produce blunt ends, and finally with Not I. pFastBac/PsoCPRII and pFastBac/EcaCPRII were transposed into baculovirus DNA and then transfected into *Spodoptera frugiperda* Sf9 cells according to the manufacturer's instructions. The insect cells were propagated and the recombinant virus was amplified according to (7). Isolation of insect cell microsomes was performed as published (7) and the cytochrome c reducing activity measured as for the yeast expression.

Heterologous expression in insect cell culture (*S. frugiperda* Sf9 cells) of pFastBac/PsoCPRII produced 4-fold more activity than the insect cell endogenous reductase, representing 40% of the activity produced by pYES2/PsoCPRII in yeast (FIG. 7B). Expression of pFastBac/PsoCPRI, the construction containing a 27 bp long 5'-noncoding region, resulted in no measurable enzyme activity above that from the endogenous insect cell reductase.

Expression of pFastBac/EcaCPRII in insect cell culture produced a 10-fold increase in reductase activity (FIG. 7D). The overexpression in insect cell culture was 54% of that achieved in yeast.

Example 5

Co-expression of cytochrome P-450 reductase and berbamunine synthase in S19 cells To test for the possible effects of a plant cytochrome P-450 reductase as opposed to either yeast or insect cell reductase, several coexpressions were undertaken.

Recombinant baculovirus containing either the *P. somniferum* or *E. californica* cytochrome P-450 cDNA was added simultaneously to *S. frugiperda* Sf9 cells (GibcoBRL) with recombinant virus containing the berbamunine synthase (CYP 80) cDNA (7). The oxidase virus was infected at a multiplicity of infection (MOI) of approximately 5 and the amount of reductase virus varied from an MOI from 1–5. The infection were carried out as described in (25).

The cytochrome P-450 oxidase that was used in these experiments was the C—O phenol coupling enzyme of bisbenzylisoquinoline alkaloid biosynthesis from *B. stolonifera*, berbamunine synthase (7). In the presence of equimolar concentrations of the two substrates (S)-N-methylcoclaurine and (R)-N-methylcoclaurine, the native enzyme produces two products in a ratio of 90:10 (berbamunine (R,S-dimer):guattegaumerine (R,R-dimer)) that correspond to the ratio of these two alkaloids found in the *Berberis* plant (6). Berbamunine synthase expressed in insect cells produced, however, the dimers R,S:R,R in a ratio of 15:85 (7). Co-infection of insect cell culture with two baculovirus preparations, one containing berbamunine synthase cDNA and the other containing *E. californica* cytochrome P-450 reductase, in varying ratios resulted in a shift in the ratio of the enzymatic products formed as follows: oxidase:reductase (5:1), R,S:R,R (29:71); oxidase:reductase (1:1), R,S:R,R (35:65); oxidase:reductase (1:2), R,S:R,R (37:63).

The isolation and functional expression of cDNAs encoding cytochrome P-450 reductases from *E. californica* and *P. somniferum* described above were undertaken to develop suitable heterologous expression systems optimal for the active expression of select cytochrome P-450-dependent oxidases of alkaloid biosynthesis, thus providing a convenient test system. Initial characterisation of the cytochrome P-450 reductase from *P. somniferum* indicated that with respect to molecular weight, $K_m$ and pH optimum, the reductase is similar to those characterised from other plant species (9, 13, 14). The purified reductase resolved into two closely migrating bands on SDS-PAGE, suggesting that isoforms are present in *P. somniferum*. This is similar to the finding that multiple reductase isoforms are present in *Arabidopsis thaliana* (16) and *H. tuberosus*. The presence of isoforms in *P. somniferum* was further supported by amino acid sequence analysis of the purified reductase as compared to the sequence identified through cDNA cloning. In addition, isolation of a cDNA encoding cytochrome P-450 reductase from *E. californica* indicated the presence of two isoforms in this plant species as well. The presence of at least two genes in each genome was corroborated by genomic DNA gel blot analysis.

The cDNA encoding one cytochrome P-450 reductase isoform from each *P. somniferum* and *E. californica* was functionally expressed in yeast in an autonomously replicating vector and in an integrative vector with transcription under the control of the GAL1 gene promoter. These vector constructions resulted in a 6- to 15-fold increase in reductase activity as compared to the activity from the endogenous yeast reductase alone. Likewise, expression of the reductases in insect cell culture using a baculovirus expression vector produced a 4- to 10-fold increase in reductase activity. Improved heterologous expression was obtained when the 5'-noncoding sequences were completely removed from the cDNAs.

Co-expression of the *Eschscholzia* reductase with the plant oxidase berbamunine synthase (7) in insect cell culture indicated that the amount of plant reductase present exerted an influence on the ratio of the products that were enzymatically formed. A first indication of this effect was shown by reconstitution of purified heterologously expressed berbamunine synthase reconstituted with *Berberis* reductase or with porcine reductase (7). Since it is difficult to standardise the lipids when reductase and oxidase are purified from microsomal membranes originating from different organisms, a co-infection of insect cells with reductase and oxidase is one method by which to avoid the varying effects of lipids. An increasing amount of plant reductase resulted in a shift in the ratio of products formed by berbamunine synthase from R,S:R,R in a ratio of 15:85 in the absence of *Eschscholzia* reductase to R,S:R,R (37:63) when a two-fold excess of baculovirus containing the *Eschscholzia* reductase was used for the co-infection. These results indicate that the cytochrome P-450 reductase may influence the binding of substrate to berbamunine synthase. Although the FMN, FAD and NADPH-binding domains of cytochrome P-450 reductase have been identified by sequence comparisons with well studied flavoproteins, less is known about the substrate binding sites (27, 28). Interaction with the non-physiological substrate cytochrome c has been demonstrated by chemical cross-linking (29) and by site-directed mutagenesis (30) to involve an acidic region between amino acid residues 200–220 of rat cytochrome P-450 reductase, but an elucidation of the specific interaction between reductase and cytochrome P-450 has not yet been reported.

Example 6

Transformation of Poppy Plant Cells with Nucleotide Sequences Encoding Cytochrome P-450 Reductase Proteins Plant Material The genotypes of *Papaver somniferum* used was C 048-6-14-64 obtained from Tasmanian Alkaloids, Australia. Seeds were surface sterilised by washing for 30–60 seconds in 70% ethanol then in 1% (w/v) sodium hypochlorite solution plus 1–2 drops of autoclaved Tween 20 or Triton X for 20 minutes with agitation. Seeds were rinsed three to four times in sterile distilled water or until no smell of bleach remains and placed on 90×25 mm Petri dishes containing B50 medium (see below). Dishes were sealed with Micropore tape and were usually stored at 4° C. for 24 to 48 hours. Seeds were germinated at 24° C. in a 16 hour light-8 hour dark cycle. Hypocotyls were excised from seedlings after 7–8 days of culture and were cut into 3–6 mm explants (usually 1–3 explants per seedling) and used in transformation experiments.

Tissue Culture Media and Conditions

All culture media consisted of B5 macronutrients, micronutrients, iron salts and vitamins (32) and 20 g/L sucrose. pH was adjusted with 1M KOH to pH 5.6, media was buffered with 10 mM MES (2-[N-Morpholino]ethanesulfonic acid) and the gelling agent was 0.8% Sigma Agar. Growth regulators were added to media prior to autoclaving at 121° C. for 20 minutes. B50 has no growth regulators and Callusing Medium (CM) has 1 mg/L 2,4-D. Antibiotics were added after autoclaving and cooling to 55–65° C. Explant and type I callus cultures were grown in Petri dishes sealed with Micropore tape at 24° C. Type II callus and somatic embryos were cultured at 18° C.

Bacterial strains and binary vectors

The disarmed *Agrobacterium tumefaciens* strains AGLO and AGLI (33) were used in transformation experiments. DNA constructs were based on the binary vector pPZP201 (34), e.g. pTAB101, with 35S 5':pat:35S 3'. *Agrobacterium* strains were maintained in glycerol at −80° C. or on LB agar plates plus appropriate selection at 4° C. Fresh cultures were grown overnight at 28° C. in 10 mL MG broth (35) without antibiotics. This *Agrobacterium* suspension was diluted to approximately $5 \times 10^8$ cells mL$^{-1}$ (OD$_{600}$=0.25) for use in transformation experiments.

Transformation and Embryogenesis

Hypocotyls were excised from seedlings and immediately inoculated by immersion in liquid *Agrobacterium* culture for 10–15 minutes. Explants were then transferred directly to CM. After four to five days co-cultivation explants were washed in sterile distilled water, until the water was clear of *Agrobacterium*, blotted on sterile filter paper and transferred to CM containing 150 mg/L Timentin plus 10 mg/L PPT (phosphinothricin, the active ingredient of Basta herbicide). Explants were transferred to fresh CM at three weekly intervals. They initially produced friable brownish type I callus which subsequently formed small regions of very white, compact embryogenic callus (type II) by about 7–8 weeks culture.

Type II callus was transferred to B50 containing 150 mg/L Timentin plus 10 mg/L PPT and cultures were transferred to fresh medium every three weeks. Meristemoid/embryo development usually occured after one or two periods on B50 medium and were seen from about 14–16 weeks total culture time.

Plantlet development from embryos was slow and required a further 3 months in tissue culture before shoot and root growth was sufficient to ensure successful transplantation to soil.

If the initial pH of the medium was 5.8 and MES was omitted, the pH of poppy cultures rapidly rose to pH 8.0 or higher. Fresh agar-solidified B5-based medium adjusted to pH 5.6 rose to pH>6.4 in the immediate area around type II callus within 30 mins. The inclusion of chlorophenol red in the medium was used to observe these localised increases in pH; the medium turns purple at pH6.4. The whole plate was pH>7 within 24 h. At the end of the culture period pH values were measured at 8.7. This rapid rise in pH resulted in very poor growth which is not compensated for by frequent changes of medium. The rapid rise was significantly delayed even by 2.5 mM MES, but 10 mM MES was preferred to adequately buffer the medium and support improved growth over the 3 week subculture period.

The identification and cloning of genes for cytochrome P-450 reductase enzymes now provides means by which the pathway of alkaloid metabolism can be regulated, specifically by alleviating the rate limiting steps which rely on cytochrome P-450. This in turn provides means of obtaining poppy plants with increased yield of alkaloids.

However, there will be instances where it may be preferable to manipulate the alkaloid metabolism of a poppy plant by suppression of genes encoding the P-450 reductases. The expression in the poppy of the cDNA encoding a P-450 reductase enzyme or part thereof, in an antisense orientation can be used to achieve this such that the expression directs the inhibition of the endogenous cytochrome P-450 reductase gene or homologues. In addition, the cDNA encoding the P-450 reductase enzyme or part thereof could be expressed in the sense orientation to direct the co-suppression of the endogenous cytochrome P-450 reductase gene or homologues. Furthermore, the cloned cDNA sequence can be used to design ribozyme sequences such as the hammerhead or hairpin ribozymes that can be used to suppress the target gene by inactivation of the endogenous cytochrome P-450 reductase gene mRNA. The genes encoding the sense, antisense or ribozymes can be delivered as transgenes stably integrated into the poppy genome or transiently in the form of a viral vector.

Although the invention has been described with reference to specific embodiments, modifications that are within the knowledge of those skilled in the art are also contemplated as being within the scope of the present invention.

REFERENCES

1. Madyastha, K. M., Meehan, T. D., and Coscia, C. J. (1976) *Biochemistry* 15, 10971102.
2. Rueffer, M., and Zenk, M. H. (1987) *Tetrahedron Lett.* 28, 5307–5310.
3. Tanahashi, T., and Zenk, M. H. (1990) *Phytochemistry* 29, 1113–1122.
4. Bauer, W., and Zenk, M. H. (1991) *Phytochemistry* 30, 2953–2961.
5. Zenk, M. H., Gerardy, R., and Stadler, R. (1989) *J. Chem. Soc., Chem. Commun.* 1725–1727.
6. Stadler, R., and Zenk, M. H. (1993) *J. Biol. Chem.* 268, 823–831.
7. Kraus, P. F. X., and Kutchan, T. M. (1995) *Proc. Natl. Acad. Sci. USA* 92, 2071–2075.
8. Madyastha, K. M., and Coscia, C. J. (1979) *J. Biol. Chem.* 254, 2419–2427.
9. Fujita, M., and Asahi, T. (1985) *Plant Cell Physiol.* 26, 397–405.
10. Benveniste, I., Gabriac, B., and Durst, F. (1986) *Biochem. J.* 235, 365–373.
11. Kochs, G., and Grisebach, H. (1989) *Arch. Biochem. Biophys.* 273, 543–553.
12. Hakamatsuka, T., Hashim, M., Ebizuka, Y., and Sankawa, U. (1991) *Tetrahedron* 47, 5969–5978.
13. Menting, J. G. T., Comish, E., and Scopes, R. K. (1994) *Plant Physiol.* 106, 643650.
14. Shet, M. S., Sathasivan, K., Arlotto, M. A., Mehdy, M. C. and Estabrook, R. W. (1993) *Proc. Natl. Acad. Sci. USA* 90, 2890–2894.
15. Meijer, A. H., Lopes Cardoso, M. I., Voskuilen, J. T., de Waal, A., Verpoorte, R., and Hoge, J. H. C. (1993) *Plant J.* 4, 47–60.
16. Pompon, D., Louerat, B., Bronine, A,. and Urban, P. (1996) *Methods Enzymol.* 272, 51–64.
17. Linsmaier, E. M., and Skoog, F. (1965) *Physiol. Plant* 18, 100–127.
18. Gundlach, H. Müller, M. J., Kutchan, T. M., and Zenk, M. H. (1992) *Proc. Natl. Acad. Sci. USA* 89, 2389–2393.
19. Diesperger, H., Müller, C. R., and Sandermann, H. Jr. (1974) *FEBS Lett.* 43, 155158.
20. Shet, M. S., Sathasivan, K., Arlotto, M. A., Mehdy, M. C. and Estabrook, R. W. (1993) *Proc. Natl. Acad. Sci. USA* 90, 2890–2894.
21. Eckerskom, C., and Lottspeich, F. (1989) *Chromatographia* 28, 92–94.
22. Cullin, C. and Pompon, D. (1988) *Gene* 65, 203–217.

23. Guengerich, F. P., Brian, W. R., Sari, M.-A., and Ross, J. T. (1991) *Methods Enzymol.* 206, 130–145.
24. Lord, J. M. (1983) in Isolation of Membranes and Organelles from Plant Cells (Hall, J. L., and Moore, A. L., Eds.), pp. 119–134, Academic Press, London.
25. Kutchan, T. M., Bock, A, and Dittrich, H. (1994) *Phytochemistry* 35, 353–360.
26. Kutchan, T. M. (1993) *J. Plant Physiol.* 142, 502–505.
27. Porter, T. D., and Kasper, C. B. (1986) *Biochemistry* 25, 1682–1687.
28. Porter, T. D. (1991) *Trends Biochem. Sci.* 16, 154–158.
29. Nisimoto, Y. (1986) *J. Biol. Chem.* 261, 14232–14239.
30. Shen, A. L., and Kasper, C. B. (1995) *J. Biol. Chem.* 270, 27475–27480.
31. Rogers, S. O. and Bendich A. J. (1985), *Plant Molec Biol* 5, 69–76
32. Gamborg, O. L., Miller, R. A. and Ojima, K. (1968). *Exp. Cells Res.* 50, 151–158.
33. Lazo, G. R., Stein, P. A. and Ludwig, R. A. (1991), *Bio/Technology,* 9, 963–967.
34. Hajdukiewicz, P., Svab, Z and Maliga, P. (1994). *Plant Mol. Biol.* 25, 989–994.
35. Garfinkle, D. J. and Nester, E. W. (1980) *J. Bacteriol.* 144, 732–743.

---

The invention claimed is:

1. A method for the production of a poppy plant alkaloid, comprising the steps of:
   a) harvesting capsules of an alkaloid poppy plant transformed or transfected with a polynucleotide comprising the coding region of SEQ ID NO: 10 to produce a straw; and
   b) chemically extracting the alkaloid or alkaloids selected from the group consisting of morphine, codeine, oripavine and thebaine from the straw obtained from the transformed or transfected alkaloid poppy plant.

2. A method for the production of a poppy alkaloid comprising the steps of:
   a) collecting and drying latex of immature capsules of an alkaloid poppy plant transformed or transfected with a polynucleotide comprising the coding region of SEQ ID NO: 10 to produce opium; and
   b) chemically extracting from the opium the alkaloid or alkaloids selected from the group consisting of morphine, codeine, oripavine and thebaine.

3. The method according to claim 1, wherein the alkaloid is selected from the group consisting of morphine, codeine and thebaine.

4. The method according to claim 2, whereas the alkaloid is selected from the group consisting of morphine, codeine and thebaine.

5. The method according to claim 1 wherein the polynucleotide comprises SEQ ID NO:10.

6. The method according to claim 2 wherein the polynucleotide comprises SEQ ID NO:10.

* * * * *

SEQUENCE LISTING

<160> NUMBER OF SEQ ID NOS: 32

<210> SEQ ID NO 1
<211> LENGTH: 10
<212> TYPE: PRT
<213> ORGANISM: Papaver somniferum

<400> SEQUENCE: 1

Lys Val Thr Ile Phe Phe Gly Thr Gln Lys
1               5                   10

<210> SEQ ID NO 2
<211> LENGTH: 18
<212> TYPE: PRT
<213> ORGANISM: Papaver somniferum

<400> SEQUENCE: 2

Lys Val Val Asp Leu Asp Asp Tyr Ala Ala Asp Asp Asp Glu Phe Glu
1               5                   10                  15

Glu Lys

<210> SEQ ID NO 3
<211> LENGTH: 18
<212> TYPE: PRT
<213> ORGANISM: Papaver somniferum

<400> SEQUENCE: 3

Lys Val Val Asp Leu Asp Asp Tyr Ala Ala Asp Asp Glu Glu Phe Glu
1               5                   10                  15

Glu Lys

<210> SEQ ID NO 4
<211> LENGTH: 8
<212> TYPE: PRT
<213> ORGANISM: Papaver somniferum

<400> SEQUENCE: 4

Lys Trp Phe Thr Glu Val Ala Lys
1               5

<210> SEQ ID NO 5
<211> LENGTH: 8
<212> TYPE: PRT
<213> ORGANISM: Papaver somniferum

<400> SEQUENCE: 5

Lys Asp Phe Thr Glu Val Ala Lys
1               5

<210> SEQ ID NO 6
<211> LENGTH: 10
<212> TYPE: PRT
<213> ORGANISM: Papaver somniferum

<400> SEQUENCE: 6

Lys Val Val Asp Glu Ile Ile Val Glu Lys
1               5                   10

<210> SEQ ID NO 7
<211> LENGTH: 10
<212> TYPE: PRT
<213> ORGANISM: Papaver somniferum

<400> SEQUENCE: 7

Lys Tyr Ala Asp Leu Leu Asn Phe Pro Lys
1               5                   10

<210> SEQ ID NO 8
<211> LENGTH: 9
<212> TYPE: PRT
<213> ORGANISM: Papaver somniferum

<400> SEQUENCE: 8

Lys Ala Ala Leu His Ala Leu Ala Lys
1               5

<210> SEQ ID NO 9
<211> LENGTH: 21
<212> TYPE: PRT
<213> ORGANISM: Papaver somniferum

<400> SEQUENCE: 9

Lys Asp Val His Arg Thr Leu His Thr Ile Val Gln Glu Gln Gly Ser
1               5                   10                  15

Leu Asp Ser Ser Lys
            20

<210> SEQ ID NO 10
<211> LENGTH: 2649
<212> TYPE: DNA
<213> ORGANISM: Papaver somniferum

<400> SEQUENCE: 10

| | | | | | |
|---|---|---|---|---|---|
| cggcacgagc | ttgttagtat | cttctagggt | ttgaaaagaa | gcacagggag | aagcaaaagt | 60 |
| cgaatctact | tgaaatacat | tcgattgctt | ctctctgttt | aagcttcaga | gtctctgcta | 120 |
| attatgggtt | cgataatttt | agctaattcg | attgaatcga | tgttaggaat | atcaatagga | 180 |
| tcagaatata | tttctgaccc | aatttcatt | atggtcacaa | ctgtagcttc | aatgctgatt | 240 |
| ggatttggtt | tcttcgcatg | tatgaaatct | tcgtcttctc | aatcaaaacc | tattgaaact | 300 |
| tataaaccaa | taattgataa | agaagaagag | gagattgaag | ttgatcctgg | taaaattaag | 360 |
| ctcactatat | tttttggtac | tcagactggt | actgctgaag | gatttgctaa | ggcattggca | 420 |
| gaagaaatta | aggcaaagta | caagaaagca | gttgttaaag | tagttgacct | ggatgactat | 480 |
| gcagccgagg | atgatcaata | tgaagagaaa | ttaaagaaag | agtctttggt | gttttttcatg | 540 |
| gtagccactt | atggtgatgg | tgagccaact | gacaatgctg | cgagatttta | caatggttc | 600 |
| actcaggaac | atgaaagggg | agagtggctt | cagcaactaa | cttatggtgt | ttttggtttg | 660 |
| ggtaaccgtc | aatacgagca | tttcaacaag | atcgcggtag | atgtggatga | gcaactcggt | 720 |

-continued

```
aaacaaggtg caaagcgcat tgttcaagtg gggctcggtg acgatgatca atgcattgaa      780
gatgatttta ctgcttggcg agaattgttg tggactgaat tggatcagtt gctcaaagat      840
gaggatgctg ctccttcagt ggctacaccg tatattgcta ctgttcctga atacagggta      900
gtgattcacg aaactacggt cgcggctctg gatgataaac acataaatac tgctaacggc      960
gatgttgcat ttgatattct ccatccttgc agaaccattg ttgctcaaca agagagctc      1020
cacaaaccca gtctgatag  atcctgtata catctggagt cgacatatc  aggctcttcc     1080
cttacatatg agactggaga tcatgttggt gtttatgctg agaactgcga tgaaactgtc     1140
gaggaagcag ggaagctgtt gggtcaaccc ctggatttgc tgttttcaat tcacacggat     1200
aaagaagacg ggtcaccca  gggaagctca ttaccacctc ctttcccagg tccttgcacc     1260
ttacgatctg ccctagcacg ctatgctgat cttttgaatc ctcctagaaa ggcttctctg     1320
attgctctgt ccgctcatgc atctgtaccc agtgaagcag agagattgcg cttttttgtca    1380
tcacctctgg gaaagaatga gtattcaaaa tgggtagttg gaagtcagag gagtcttttg     1440
gagatcatgg ccgagtttcc atcagcaaaa ccccctcttg gtgtgttctt tgctgcagta     1500
gcccctcgct taccgcctcg atactattct atctcatcct ctcctaagtt tgctccctca     1560
agaattcatg tgacgtgtgc tttagtatat ggtcaaagcc ctaccggaag ggttcaccga     1620
ggagtgtgtt cgacatggat gaagcatgca gttcctcagg atagctgggc tcctattttt     1680
gttcgaacgt caaacttcaa gttaccagct gaccccctcaa ctccaattat catggtggga    1740
cctggtacag ggttagctcc tttcagagga tttctgcagg aaagaatggc cctcaaggaa     1800
aatggtgctc aacttggccc agcagtgctc tttttcggat gtaggaatcg taatatggac     1860
ttcatttatg aagacgaact aaacaacttc gtggaacgag gagtcatttc ggagctagtt     1920
attgcctttt cacgtgaagg ggaaaagaag gaatatgttc aacataagat gatggagaaa     1980
gcaacggatg tatggaatgt gatatcaggg gacggttatc tctatgtgtg tggtgatgcc     2040
aagggaatgg ccagagatgt ccatcgcacg ttgcatacca ttgcccaaga acagggaccc     2100
atggaatcat ctgctgccga agctgcagta aagaaactcc aagttgaaga acgatatcta     2160
agagatgtct ggtgatcgaa tgtagcttgc caagtcccct tttcttggct ggtctgttta     2220
tggtttctat tatattattg atcctcctct gaaaatccca agcacttcca gacatccctc     2280
gattcttcct ccagtggttc aaatcgaagc tcggtataa ttgagagcag tgcaattgtg      2340
actacatgag aagcaaacat cgaataccat agaattagaa agatcaaaat tctcttatca     2400
gaacaatgtt acaggcaaaa ctgtgtttgc ttaatataaa tttcacacca tgggtgtgga    2460
caacactgaa acagtattag ctataccaac aaagttatgc aaggaaacac aaactagtta     2520
gatcttctct ttggattgat tactgtaagt tctaaccaga tgatagattg tacttaaaga    2580
ttcttgtttt cttatggcta ccgagaggag tatattaatg catttagagt tttgagaaaa    2640
aaaaaaaaa                                                              2649
```

```
<210> SEQ ID NO 11
<211> LENGTH: 2558
<212> TYPE: DNA
<213> ORGANISM: Eschscholzia californica

<400> SEQUENCE: 11
ttcttcttcc aatcgcattc gagaaaattc aatcatcttc aacttcagga agaagaatca       60
tcagaaacac tgaagctcat catcatcctt gaaacttatc gtctttgttt gacctttga      120
aaaactatgg aacaaactgc ggttaaagtc tctttgtttg atctattttc ttcgatactt     180
```

```
aatggaaagt tggatccgtc gaacttttct tcagattcaa gtgctgctat tttgattgaa      240
aatcgtgaga ttttaatgat cttaacaact gctattgctg tttttatcgg ttgtggtttt      300
ctctacgttt ggagaagatc ttcaaataag tcgagtaaaa ttgttgaaac tcagaaattg      360
atcgttgaaa aggaaccaga acctgaagtt gatgatggaa agaagaaggt tactatcttc      420
tttggtactc aaactggtac agctgaagga ttcgcaaagg cacttgctga agaagcaaaa      480
gcaagatatg aaaaggcaat ctttaaagtg attgatctgg atgattacgg agcagatgat      540
gatgaattcg aagagaaatt gaaaaaggaa actatagctc ttttctttttt ggctacctat      600 ggagatggtg aacctacaga taatgctgca agattttata atggttcac agaggggaga       660 gagggaaatg tggctccaga atcttcaatt tggtgtcttc ggtctaggca atagacagta      720
tgagcatttc aataaggtgg caaggaggt ggacgagata ctcactgaac agggtgggaa       780
gcgtattgtt cccgtgggtc taggagatga tgatcaatgc atagaagatg atttcactgc      840
gtggcgggag ttggtatggc ctgaattgga tcagttgctc cttgatgaaa gtgataaaac      900
atctgtttct actccttaca ctgccatcgt accagaatac agggtagtat tccatgatgc      960
tactgatgca tcactacaag acaaaaactg gagcaatgca aatggctaca ctgtttacga     1020
cgttcaacac ccatgcagag ccaatgtcgt tgtaaagaag gagcttcaca ctccagtatc     1080
tgatcgttct tgtattcatc tggaatttga catttctggc actgggctca cgtatgaaac     1140
aggagaccat gtcggtgttt actctgagaa ttgtgttgaa gttgtcgagg aagcagagag     1200
gctattgggt tactcatcag acaccgtttt ttcaatccat gtcgataaag aggacggctc     1260
acccattagt ggaagcgctc tagctcctcc ttttccaact ccctgcactc taagaacagc     1320
actaacacga tacgctgatc tgttgaattc tcccaagaag gctgctctgc atgctttggc     1380
tgcttatgca tccgatccaa aggaagcgga gcgactaagg tatcttgcgt ctcctgctgg     1440
gaaggacgaa tacgcccagt ggatagtagc tagtcagaga agtctgctag tggtcatggc     1500
tgaattccca tcagcaaagg ctccaattgg ggttttcttt gcagcagtag ctcctcgctt     1560
gctgccaaga tactattcta tttcatcttc caataggatg gtaccatcta ggattcatgt     1620
cacatgtgca ttggtgcatg aaaaaacacc ggcaggtcgg gttcacaaag gagtgtgttc     1680
aacctggatg aagaattctg tgtctttgga agaaaaccat gattgcagca gctgggcacc     1740
aatctttgtc aggcaatcca acttcaaact tcctgctgat tctacagtac aattataat      1800 gattggtcct gggactggat agctcccctt taggggattc atgcaggagc gattagctct     1860
gaagaattct ggtgtagaat tgggacccgc tatcctcttc tttggatgca gaaacagaca     1920 gatgattac atatatgaag aggagctaaa caactttgtg aaagagggag ctatctccga      1980
agttgttgtt gctttctcac gtgagggagc taccaaggaa tacgtacaac ataaaatggc     2040
ggagaaggct tcctacatct gggaaatgat ctctcaaggt gcttatcttt atgtatgtgg     2100
tgatgccaag ggcatggcta gagacgtaca tcgaactctc cacaccattg cccaggaaca     2160
gggatctttg acaactcga agaccgaaag cttggtgaag aatctacaga tggatggaag     2220
gtatctacgt gatgtgtggt gattgatttt ttcagcacgg ttacaatcta gcttcatcaa     2280
agaacgcgct tgagaagcat aaatcttagt tgcagagatg ttgatttcag aagaaatgct     2340
ttatatactt gaggtagcgg acattaatcc ttttctctct ctctaaactg ttaatcctgt     2400
aaaaaaggga ttgctgtttg tgtttgctcg caatcaatta agttatattc tttggtctat     2460
ggcattcgtt agacaaatat attaacgagt ttgtccgtta tatatgacat atgaaacaaa     2520
```

-continued

| agaacttctg tttggaggaa gagaaaaaaa aaaaaaaa | 2558 |

<210> SEQ ID NO 12
<211> LENGTH: 2650
<212> TYPE: DNA
<213> ORGANISM: Papaver somniferum

<400> SEQUENCE: 12

| cggcacgagc ttgttagtat cttctagggt ttgaaaagaa gcacagggag aagcaaaagt | 60 |
| cgaatctact tgaaatacat tcgattgctt ctctctgttt aagcttcaga gtctctgcta | 120 |
| attatgggtt cgaataattt agctaattcg attgaatcga tgttaggaat atcaatagga | 180 |
| tcagaatata tttctgaccc aattttcatt atggtcacaa ctgtagcttc aatgctgatt | 240 |
| ggatttggtt tcttcgcatg tatgaaatct tcgtcttctc aatcaaaacc tattgaaact | 300 |
| tataaaccaa taattgataa agaagaagag gagattgaag ttgatcctgg taaaattaag | 360 |
| ctcactatat tttttggtac tcagactggt actgctgaag gatttgctaa ggcattggca | 420 |
| gaagaaatta aggcaaagta caagaaagca gttgttaaag tagttgaccct ggatgactat | 480 |
| gcagccgagg atgatcaata tgaagagaaa ttaaagaaag agtctttggt gtttttcatg | 540 |
| gtagccactt atggtgatgg tgagccaact gacaatgctg cgagatttta caatggttc | 600 |
| actcaggaac atgaaagggg agagtggctt cagcaactaa cttatggtgt ttttggtttg | 660 |
| ggtaaccgtc aatacgagca tttcaacaag atcgcggtag atgtggatga gcaactcggt | 720 |
| aaacaaggtg caaagcgcat tgttcaagtg gggctcggtg acgatgatca atgcattgaa | 780 |
| gatgatttta ctgcttggcg agaattgttg tggactgaat tggatcagtt gctcaaagat | 840 |
| gaggatgctc tccttcagt ggctacaccg tatattgcta ctgttcctga atacagggta | 900 |
| gtgattcacg aaactacggt cgcggctctg gatgataaac atatactac tgctaacggc | 960 |
| gatgttgcat ttgatattct ccatccttgc agaaccattg ttgctcaaca agagagctc | 1020 |
| cacaaaccca gtctgatag atcctgtata catctggagt tcgacatatc aggctcttcc | 1080 |
| cttacatatg agactggaga tcatgttggt gtttatgctg agaactgcga tgaaactgtc | 1140 |
| gaggaagcag ggaagctgtt gggtcaaccc ctggatttgc tgttttcaat tcacacggat | 1200 |
| aaagaagacg ggtcaccccca gggaagctca ttaccacctc ctttccccagg tccttgcacc | 1260 |
| ttacgatctg ccctagcacg ctatgctgat cttttgaatc ctcctagaaa ggcttctctg | 1320 |
| attgctctgt ccgctcatgc atctgtaccc agtgaagcag agagattgcg cttttttgtca | 1380 |
| tcacctctgg gaaagaatga gtattcaaaa tgggtagttg gaagtcagag gagtcttttg | 1440 |
| gagatcatgg ccgagtttcc atcagcaaaa cccctcttg gtgttttctt tgctgcagta | 1500 |
| gccctcgct taccgcctcg atactattct atctcatcct ctcctaagtt tgctccctca | 1560 |
| agaattcatg tgacgtgtgc tttagtatat ggtcaaagcc ctaccggaag ggttcaccga | 1620 |
| ggagtgtgtt cgacatggat gaagcatgca gttcctcagg atagctgggc tcctatttt | 1680 |
| gttcgaacgt caaacttcaa gttaccagct gaccccctcaa ctccaattat catggtggga | 1740 |
| cctggtacag ggttagctcc tttcagagga tttctgcagg aaagaatggc cctcaaggaa | 1800 |
| aatggtgctc aacttggccc agcagtgctc ttttttcggat gtaggaatcg taatatggac | 1860 |
| ttcatttatg aagacgaact aaacaacttc gtggaacgag gagtaaattc ggagctagtt | 1920 |
| attgccttt cacgtgaagg ggaaaagaag gaatatgttc aacataagat gatggagaaa | 1980 |
| gcaacggatg tatggaatgt gatatcaggg acggttatc tctatgtgtg tggtgatgcc | 2040 |
| aagggaatgg ccagagatgt ccatcgcacg ttgcatacca ttgcccaaga acagggaccc | 2100 |

-continued

```
atggaatcat ctgctgccga agctgcagta agaaactcc  aagttgaaga  acgatatcta   2160
agagatgtct ggtgatcgaa tgtagcttgc caagtcccct tttcttggct ggtctgttta   2220
tggtttctat tatattattg atcctcctct gaaaatccca agcacttcca gacatccctc   2280
gattcttcct ccagtggttc caaatcgaag ctcggtataa ttgagagcag tgcaattgtg   2340
actacatgag aagcaaacat cgaataccat agaattagaa agatcaaaat tctcttatca   2400
gaacaatgtt acaggcaaaa ctgtgtttgc ttaatataaa tttcacacca tgggtgtgga   2460
caacactgaa acagtattag ctataccaac aaagttatgc aaggaaacac aaactagtta   2520
gatcttctct ttggattgat tactgtaagt tctaaccaga tgatagattg tacttaaaga   2580
ttcttgtttt cttatggcta ccgagaggag tatattaatg catttagagt tttgagaaaa   2640
aaaaaaaaaa                                                          2650
```

<210> SEQ ID NO 13
<211> LENGTH: 683
<212> TYPE: PRT
<213> ORGANISM: Papaver somniferum

<400> SEQUENCE: 13

```
Met Gly Ser Asn Asn Leu Ala Asn Ser Ile Glu Ser Met Leu Gly Ile
1               5                   10                  15

Ser Ile Gly Ser Glu Tyr Ile Ser Asp Pro Ile Phe Ile Met Val Thr
            20                  25                  30

Thr Val Ala Ser Met Leu Ile Gly Phe Gly Phe Phe Ala Cys Met Lys
        35                  40                  45

Ser Ser Ser Ser Gln Ser Lys Pro Ile Glu Thr Tyr Lys Pro Ile Ile
    50                  55                  60

Asp Lys Glu Glu Glu Ile Glu Val Asp Pro Gly Lys Ile Lys Leu
65                  70                  75                  80

Thr Ile Phe Phe Gly Thr Gln Thr Gly Thr Ala Glu Gly Phe Ala Lys
                85                  90                  95

Ala Leu Ala Glu Glu Ile Lys Ala Lys Tyr Lys Lys Ala Val Val Lys
            100                 105                 110

Val Val Asp Leu Asp Asp Tyr Ala Ala Glu Asp Gln Tyr Glu Glu
        115                 120                 125

Lys Leu Lys Lys Glu Ser Leu Val Phe Phe Met Val Ala Thr Tyr Gly
    130                 135                 140

Asp Gly Glu Pro Thr Asp Asn Ala Ala Arg Phe Tyr Lys Trp Phe Thr
145                 150                 155                 160

Gln Glu His Glu Arg Gly Glu Trp Leu Gln Gln Leu Thr Tyr Gly Val
                165                 170                 175

Phe Gly Leu Gly Asn Arg Gln Tyr Glu His Phe Asn Lys Ile Ala Val
            180                 185                 190

Asp Val Asp Glu Gln Leu Gly Lys Gln Gly Ala Lys Arg Ile Val Gln
        195                 200                 205

Val Gly Leu Gly Asp Asp Gln Cys Ile Glu Asp Phe Thr Ala
    210                 215                 220

Trp Arg Glu Leu Leu Trp Thr Glu Leu Asp Gln Leu Leu Lys Asp Glu
225                 230                 235                 240

Asp Ala Ala Pro Ser Val Ala Thr Pro Tyr Ile Ala Thr Val Pro Glu
                245                 250                 255

Tyr Arg Val Val Ile His Glu Thr Val Ala Ala Leu Asp Asp Lys
            260                 265                 270
```

-continued

```
His Ile Asn Thr Ala Asn Gly Asp Val Ala Phe Asp Ile Leu His Pro
        275                 280                 285

Cys Arg Thr Ile Val Ala Gln Gln Arg Glu Leu His Lys Pro Lys Ser
        290                 295                 300

Asp Arg Ser Cys Ile His Leu Glu Phe Asp Ile Ser Gly Ser Ser Leu
305                 310                 315                 320

Thr Tyr Glu Thr Gly Asp His Val Gly Val Tyr Ala Glu Asn Cys Asp
                325                 330                 335

Glu Thr Val Glu Glu Ala Gly Lys Leu Leu Gly Gln Pro Leu Asp Leu
            340                 345                 350

Leu Phe Ser Ile His Thr Asp Lys Glu Asp Gly Ser Pro Gln Gly Ser
        355                 360                 365

Ser Leu Pro Pro Pro Phe Pro Gly Pro Cys Thr Leu Arg Ser Ala Leu
        370                 375                 380

Ala Arg Tyr Ala Asp Leu Leu Asn Pro Pro Arg Lys Ala Ser Leu Ile
385                 390                 395                 400

Ala Leu Ser Ala His Ala Ser Val Pro Ser Glu Ala Glu Arg Leu Arg
                405                 410                 415

Phe Leu Ser Ser Pro Leu Gly Lys Asn Glu Tyr Ser Lys Trp Val Val
            420                 425                 430

Gly Ser Gln Arg Ser Leu Leu Glu Ile Met Ala Glu Phe Pro Ser Ala
        435                 440                 445

Lys Pro Pro Leu Gly Val Phe Phe Ala Ala Val Ala Pro Arg Leu Pro
450                 455                 460

Pro Arg Tyr Tyr Ser Ile Ser Ser Ser Pro Lys Phe Ala Pro Ser Arg
465                 470                 475                 480

Ile His Val Thr Cys Ala Leu Val Tyr Gly Gln Ser Pro Thr Gly Arg
                485                 490                 495

Val His Arg Gly Val Cys Ser Thr Trp Met Lys His Ala Val Pro Gln
            500                 505                 510

Asp Ser Trp Ala Pro Ile Phe Val Arg Thr Ser Asn Phe Lys Leu Pro
        515                 520                 525

Ala Asp Pro Ser Thr Pro Ile Ile Met Val Gly Pro Gly Thr Gly Leu
        530                 535                 540

Ala Pro Phe Arg Gly Phe Leu Gln Glu Arg Met Ala Leu Lys Glu Asn
545                 550                 555                 560

Gly Ala Gln Leu Gly Pro Ala Val Leu Phe Phe Gly Cys Arg Asn Arg
                565                 570                 575

Asn Met Asp Phe Ile Tyr Glu Asp Glu Leu Asn Asn Phe Val Glu Arg
            580                 585                 590

Gly Val Ile Ser Glu Leu Val Ile Ala Phe Ser Arg Glu Gly Glu Lys
        595                 600                 605

Lys Glu Tyr Val Gln His Lys Met Met Glu Lys Ala Thr Asp Val Trp
        610                 615                 620

Asn Val Ile Ser Gly Asp Gly Tyr Leu Tyr Val Cys Gly Asp Ala Lys
625                 630                 635                 640

Gly Met Ala Arg Asp Val His Arg Thr Leu His Thr Ile Ala Gln Glu
                645                 650                 655

Gln Gly Pro Met Glu Ser Ser Ala Ala Glu Ala Ala Val Lys Lys Leu
            660                 665                 670

Gln Val Glu Glu Arg Tyr Leu Arg Asp Val Trp
        675                 680
```

-continued

<210> SEQ ID NO 14
<211> LENGTH: 2558
<212> TYPE: DNA
<213> ORGANISM: Eschscholzia californica

<400> SEQUENCE: 14

```
ttcttcttcc aatcgcattc gagaaaattc aatcatcttc aacttcagga agaagaatca      60
tcagaaacac tgaagctcat catcatcctt gaaacttatc gtctttgttt gacctttga     120
aaaactatgg aacaaactgc ggttaaagtc tctttgtttg atctattttc ttcgatactt     180
aatgaaagt tggatccgtc gaacttttct tcagattcaa gtgctgctat tttgattgaa     240
aatcgtgaga ttttaatgat cttaacaact gctattgctg tttttatcgg ttgtggtttt     300
ctctacgttt ggagaagatc ttcaaataag tcgagtaaaa ttgttgaaac tcagaaattg     360
atcgttgaaa aggaaccaga acctgaagtt gatgatggaa agaagaaggt tactatcttc     420
tttggtactc aaactggtac agctgaagga ttcgcaaagg cacttgctga agaagcaaaa     480
gcaagatatg aaaaggcaat cttttaaagtg attgatctgg atgattacgg agcagatgat     540
gatgaattcg aagagaaatt gaaaaaggaa actatagctc ttttctttt ggctacctat     600
ggagatggtg aacctacaga taatgctgca agattttata atggttcac agaggagag     660
agggaaatgt ggctccagaa tcttcaattt ggtgtcttcg gtctaggcaa tagacagtat     720
gagcatttca ataaggtggc aaaggaggtg gacgagatac tcactgaaca gggtgggaag     780
cgtattgttc ccgtgggtct aggagatgat gatcaatgca tagaagatga tttcactgcg     840
tggcgggagt tggtatggcc tgaattggat cagttgctcc ttgatgaaag tgataaaaca     900
tctgtttcta ctccttacac tgccatcgta ccagaataca gggtagtatt ccatgatgct     960
actgatgcat cactacaaga caaaaactgg agcaatgcaa atggctacac tgtttacgac    1020
gttcaacacc catgcagagc caatgtcgtt gtaaagaagg agcttcacac tccagtatct    1080
gatcgttctt gtattcatct ggaatttgac atttctggca ctgggctcac gtatgaaaca    1140
ggagaccatg tcggtgttta ctctgagaat tgtgttgaag ttgtcgagga agcagagagg    1200
ctattgggtt actcatcaga caccgttttt tcaatccatg tcgataaaga ggacggctca    1260
cccattagtg gaagcgctct agctcctcct tttccaactc cctgcactct aagaacagca    1320
ctaacacgat acgctgatct gttgaattct cccaagaagg ctgctctgca tgctttggct    1380
gcttatgcat ccgatccaaa ggaagcggag cgactaaggt atcttgcgtc tcctgctggg    1440
aaggacgaat acgcccagtg gatagtagct agtcagagaa gtctgctagt ggtcatggct    1500
gaattcccat cagcaaaggc tccaattggg gttttcttttg cagcagtagc tcctcgcttg    1560
ctgccaagat actattctat ttcatcttcc aataggatgg taccatctag gattcatgtc    1620
acatgtgcat tggtgcatga aaaaacaccg gcaggtcggg ttcacaaagg agtgtgttca    1680
acctggatga agaattctgt gtcttttggaa gaaaccatg attgcagcag ctgggcacca    1740
atctttgtca ggcaatccaa cttcaaactt cctgctgatt ctacagtacc aattataatg    1800
attggtcctg ggactggatt agctccctt agggattca tgcaggagcg attagctctg    1860
aagaattctg gtgtagaatt gggacccgct atcctcttct ttggatgcag aaacagacag    1920
atggattaca tatatgaaga ggagctaaac aactttgtga agagggagc tatctccgaa    1980
gttgttgttg ctttctcacg tgagggagct accaaggaat acgtacaaca taaaatggcg    2040
gagaaggctt cctacatctg ggaaatgatc tctcaaggtg cttatcttta tgtatgtggt    2100
gatgccaagg gcatggctag agacgtacat cgaactctcc acaccattgc ccaggaacag    2160
```

-continued

```
ggatctttgg acaactcgaa gaccgaaagc ttggtgaaga atctacagat ggatggaagg    2220
tatctacgtg atgtgtggtg attgattttt tcagcacggt tacaatctag cttcatcaaa    2280
gaacgcgctt gagaagcata atcttagtt gcagagatgt tgatttcaga gaaatgctt     2340 tatatacttg aggtagcgga cattaatcct tttctctctc tctaaactgt taatcctgta    2400
aaaaagggat gctgtttgt gtttgctcgc aatcaattaa gttatattct ttggtctatg     2460
gcattcgtta gacaaatata ttaacgagtt tgtccgttat atatgacata tgaaacaaaa    2520
gaacttctgt ttggaggaag agaaaaaaaa aaaaaaaa                            2558
```

<210> SEQ ID NO 15
<211> LENGTH: 704
<212> TYPE: PRT
<213> ORGANISM: Eschscholzia californica

<400> SEQUENCE: 15

```
Met Glu Gln Thr Ala Val Lys Val Ser Leu Phe Asp Leu Phe Ser Ser
1               5                   10                  15

Ile Leu Asn Gly Lys Leu Asp Pro Ser Asn Phe Ser Ser Asp Ser Ser
            20                  25                  30

Ala Ala Ile Leu Ile Glu Asn Arg Glu Ile Leu Met Ile Leu Thr Thr
        35                  40                  45

Ala Ile Ala Val Phe Ile Gly Cys Gly Phe Leu Tyr Val Trp Arg Arg
    50                  55                  60

Ser Ser Asn Lys Ser Ser Lys Ile Val Glu Thr Gln Lys Leu Ile Val
65                  70                  75                  80

Glu Lys Glu Pro Glu Pro Glu Val Asp Asp Gly Lys Lys Val Thr
                85                  90                  95

Ile Phe Phe Gly Thr Gln Thr Gly Thr Ala Glu Gly Phe Ala Lys Ala
            100                 105                 110

Leu Ala Glu Glu Ala Lys Ala Arg Tyr Glu Lys Ala Ile Phe Lys Val
        115                 120                 125

Ile Asp Leu Asp Asp Tyr Gly Ala Asp Asp Glu Phe Glu Glu Lys
    130                 135                 140

Leu Lys Lys Glu Thr Ile Ala Leu Phe Phe Leu Ala Thr Tyr Gly Asp
145                 150                 155                 160

Gly Glu Pro Thr Asp Asn Ala Ala Arg Phe Tyr Lys Trp Phe Thr Glu
                165                 170                 175

Gly Glu Arg Glu Met Trp Leu Gln Asn Leu Gln Phe Gly Val Phe Gly
            180                 185                 190

Leu Gly Asn Arg Gln Tyr Glu His Phe Asn Lys Val Ala Lys Glu Val
        195                 200                 205

Asp Glu Ile Leu Thr Glu Gln Gly Gly Lys Arg Ile Val Pro Val Gly
    210                 215                 220

Leu Gly Asp Asp Asp Gln Cys Ile Glu Asp Asp Phe Thr Ala Trp Arg
225                 230                 235                 240

Glu Leu Val Trp Pro Glu Leu Asp Gln Leu Leu Leu Asp Glu Ser Asp
                245                 250                 255

Lys Thr Ser Val Ser Thr Pro Tyr Thr Ala Ile Val Pro Glu Tyr Arg
            260                 265                 270

Val Val Phe His Asp Ala Thr Asp Ala Ser Leu Gln Asp Lys Asn Trp
        275                 280                 285

Ser Asn Ala Asn Gly Tyr Thr Val Tyr Asp Val Gln His Pro Cys Arg
    290                 295                 300
```

-continued

```
Ala Asn Val Val Lys Lys Glu Leu His Thr Pro Val Ser Asp Arg
305                 310                 315                 320

Ser Cys Ile His Leu Glu Phe Asp Ile Ser Gly Thr Gly Leu Thr Tyr
                325                 330                 335

Glu Thr Gly Asp His Val Gly Val Tyr Ser Glu Asn Cys Val Glu Val
                340                 345                 350

Val Glu Glu Ala Glu Arg Leu Leu Gly Tyr Ser Ser Asp Thr Val Phe
            355                 360                 365

Ser Ile His Val Asp Lys Glu Asp Gly Ser Pro Ile Ser Gly Ser Ala
        370                 375                 380

Leu Ala Pro Pro Phe Pro Thr Pro Cys Thr Leu Arg Thr Ala Leu Thr
385                 390                 395                 400

Arg Tyr Ala Asp Leu Leu Asn Ser Pro Lys Ala Ala Leu His Ala
                405                 410                 415

Leu Ala Ala Tyr Ala Ser Asp Pro Lys Glu Ala Glu Arg Leu Arg Tyr
                420                 425                 430

Leu Ala Ser Pro Ala Gly Lys Asp Glu Tyr Ala Gln Trp Ile Val Ala
        435                 440                 445

Ser Gln Arg Ser Leu Leu Val Val Met Ala Glu Phe Pro Ser Ala Lys
    450                 455                 460

Ala Pro Ile Gly Val Phe Phe Ala Ala Val Ala Pro Arg Leu Leu Pro
465                 470                 475                 480

Arg Tyr Tyr Ser Ile Ser Ser Ser Asn Arg Met Val Pro Ser Arg Ile
                485                 490                 495

His Val Thr Cys Ala Leu Val His Glu Lys Thr Pro Ala Gly Arg Val
                500                 505                 510

His Lys Gly Val Cys Ser Thr Trp Met Lys Asn Ser Val Ser Leu Glu
        515                 520                 525

Glu Asn His Asp Cys Ser Ser Trp Ala Pro Ile Phe Val Arg Gln Ser
    530                 535                 540

Asn Phe Lys Leu Pro Ala Asp Ser Thr Val Pro Ile Ile Met Ile Gly
545                 550                 555                 560

Pro Gly Thr Gly Leu Ala Pro Phe Arg Gly Phe Met Gln Glu Arg Leu
                565                 570                 575

Ala Leu Lys Asn Ser Gly Val Glu Leu Gly Pro Ala Ile Leu Phe Phe
            580                 585                 590

Gly Cys Arg Asn Arg Gln Met Asp Tyr Ile Tyr Glu Glu Glu Leu Asn
        595                 600                 605

Asn Phe Val Lys Glu Gly Ala Ile Ser Glu Val Val Ala Phe Ser
    610                 615                 620

Arg Glu Gly Ala Thr Lys Glu Tyr Val Gln His Lys Met Ala Glu Lys
625                 630                 635                 640

Ala Ser Tyr Ile Trp Glu Met Ile Ser Gln Gly Ala Tyr Leu Tyr Val
                645                 650                 655

Cys Gly Asp Ala Lys Gly Met Ala Arg Asp Val His Arg Thr Leu His
                660                 665                 670

Thr Ile Ala Gln Glu Gln Gly Ser Leu Asp Asn Ser Lys Thr Glu Ser
            675                 680                 685

Leu Val Lys Asn Leu Gln Met Asp Gly Arg Tyr Leu Arg Asp Val Trp
        690                 695                 700

<210> SEQ ID NO 16
<211> LENGTH: 2100
```

<212> TYPE: DNA
<213> ORGANISM: Papaver somniferum

<400> SEQUENCE: 16

```
aagcttcaga gtctctgcta attatgggtt cgaataattt agctaattcg attgaatcga      60
tgttaggaat atcaatagga tcagaatata tttctgaccc aattttcatt atggtcacaa     120
ctgtagcttc aatgctgatt ggatttggtt tcttcgcatg tatgaaatct tcgtcttctc     180
aatcaaaacc tattgaaact tataaaccaa taattgataa agaagaagag gagattgaag     240
ttgatcctgg taaaattaag ctcactatat tttttggtac tcagactggt actgctgaag     300
gatttgctaa ggcattggca gaagaaatta aggcaaagta caagaaagca gttgttaaag     360
tagttgacct ggatgactat gcagccgagg atgatcaata tgaagagaaa ttaaagaaag     420
agtctttggt gttttcatg gtagccactt atggtgatgg tgagccaact gacaatgctg     480
cgagatttta caaatggttc actcaggaac atgaaagggg agagtggctt cagcaactaa     540
cttatggtgt ttttggtttg ggtaaccgtc aatacgagca tttcaacaag atcgcggtag     600
atgtggatga gcaactcggt aaacaaggtg caaagcgcat tgttcaagtg gggctcggtg     660
acgatgatca atgcattgaa gatgatttta ctgcttggcg agaattgttg tggactgaat     720
tggatcagtt gctcaaagat gaggatgctg ctccttcagt ggctacaccg tatattgcta     780
ctgttcctga atacagggta gtgattcacg aaactacggt cgcggctctg gatgataaac     840
acataaatac tgctaacggc gatgttgcat tgatattctc ccatccttgc agaaccattg     900
ttgctcaaca aagagagctc cacaaaccca gtctgatag atcctgtata catctggagt     960
tcgacatatc aggctcttcc cttacatatg agactggaga tcatgttggt gtttatgctg    1020
agaactgcga tgaaactgtc gaggaagcag ggaagctgtt gggtcaaccc ctggatttgc    1080
tgttttcaat tcacacggat aaagaagacg ggtcacccca gggaagctca ttaccacctc    1140
ctttcccagg tccttgcacc ttacgatctg ccctagcacg ctatgctgat cttttgaatc    1200
ctcctagaaa ggcttctctg attgctctgt ccgctcatgc atctgtaccc agtgaagcag    1260
agagattgcg cttttgtca tcacctctgg gaaagaatga gtattcaaaa tgggtagttg    1320
gaagtcagag gagtcttttg gagatcatgg ccgagtttcc atcagcaaaa ccccctcttg    1380
gtgttttctt tgctgcagta gcccctcgct taccgcctcg atactattct atctcatcct    1440
ctcctaagtt tgctccctca agaattcatg tgacgtgtgc tttagtatat ggtcaaagcc    1500
ctaccggaag ggttcaccga ggagtgtgtt cgacatggat gaagcatgca gttcctcagg    1560
atagctgggc tcctattttt gttcgaacgt caaacttcaa gttaccagct gacccctcaa    1620
ctccaattat catggtggga cctggtacag ggttagctcc tttcagagga tttctgcagg    1680
aaagaatggc cctcaaggaa aatggtgctc aacttggccc agcagtgctc tttttcggat    1740
gtaggaatcg taatatggac ttcatttatg aagacgaact aaacaacttc gtggaacgag    1800
gagtaatttc ggagctagtt attgccttt cacgtgaagg ggaaagaag gaatatgttc    1860
aacataagat gatggagaaa gcaacggatg tatggaatgt gatatcaggg gacggttatc    1920
tctatgtgtg tggtgatgcc aagggaatgg ccagagatgt ccatcgcacg ttgcatacca    1980
ttgcccaaga acagggaccc atggaatcat ctgctgccga agctgcagta aagaaactcc    2040
aagttgaaga acgatatcta agagatgtct ggtgatcgaa tgtagcttgc caatcactag    2100
```

<210> SEQ ID NO 17
<211> LENGTH: 683
<212> TYPE: PRT

<213> ORGANISM: Papaver somniferum

<400> SEQUENCE: 17

```
Met Gly Ser Asn Asn Leu Ala Asn Ser Ile Glu Ser Met Leu Gly Ile
1               5                   10                  15

Ser Ile Gly Ser Glu Tyr Ile Ser Asp Pro Ile Phe Ile Met Val Thr
            20                  25                  30

Thr Val Ala Ser Met Leu Ile Gly Phe Gly Phe Ala Cys Met Lys
        35                  40                  45

Ser Ser Ser Ser Gln Ser Lys Pro Ile Glu Thr Tyr Lys Pro Ile Ile
        50                  55                  60

Asp Lys Glu Glu Glu Ile Glu Val Asp Pro Gly Lys Ile Lys Leu
65                  70                  75                  80

Thr Ile Phe Phe Gly Thr Gln Thr Gly Thr Ala Glu Gly Phe Ala Lys
                    85                  90                  95

Ala Leu Ala Glu Glu Ile Lys Ala Lys Tyr Lys Lys Ala Val Val Lys
                100                 105                 110

Val Val Asp Leu Asp Asp Tyr Ala Ala Glu Asp Gln Tyr Glu Glu
        115                 120                 125

Lys Leu Lys Lys Glu Ser Leu Val Phe Phe Met Val Ala Thr Tyr Gly
130                 135                 140

Asp Gly Glu Pro Thr Asp Asn Ala Ala Arg Phe Tyr Lys Trp Phe Thr
145                 150                 155                 160

Gln Glu His Glu Arg Gly Glu Trp Leu Gln Gln Leu Thr Tyr Gly Val
                165                 170                 175

Phe Gly Leu Gly Asn Arg Gln Tyr Glu His Phe Asn Lys Ile Ala Val
            180                 185                 190

Asp Val Asp Glu Gln Leu Gly Lys Gln Gly Ala Lys Arg Ile Val Gln
        195                 200                 205

Val Gly Leu Gly Asp Asp Gln Cys Ile Glu Asp Asp Phe Thr Ala
        210                 215                 220

Trp Arg Glu Leu Leu Trp Thr Glu Leu Asp Gln Leu Leu Lys Asp Glu
225                 230                 235                 240

Asp Ala Ala Pro Ser Val Ala Thr Pro Tyr Ile Ala Thr Val Pro Glu
                245                 250                 255

Tyr Arg Val Val Ile His Glu Thr Thr Val Ala Ala Leu Asp Asp Lys
            260                 265                 270

His Ile Asn Thr Ala Asn Gly Asp Val Ala Phe Asp Ile Leu His Pro
        275                 280                 285

Cys Arg Thr Ile Val Ala Gln Gln Arg Glu Leu His Lys Pro Lys Ser
290                 295                 300

Asp Arg Ser Cys Ile His Leu Glu Phe Asp Ile Ser Gly Ser Ser Leu
305                 310                 315                 320

Thr Tyr Glu Thr Gly Asp His Val Gly Val Tyr Ala Glu Asn Cys Asp
                325                 330                 335

Glu Thr Val Glu Glu Ala Gly Lys Leu Leu Gly Gln Pro Leu Asp Leu
            340                 345                 350

Leu Phe Ser Ile His Thr Asp Lys Glu Asp Gly Ser Pro Gln Gly Ser
        355                 360                 365

Ser Leu Pro Pro Pro Phe Pro Gly Pro Cys Thr Leu Arg Ser Ala Leu
370                 375                 380

Ala Arg Tyr Ala Asp Leu Leu Asn Pro Pro Arg Lys Ala Ser Leu Ile
385                 390                 395                 400
```

```
Ala Leu Ser Ala His Ala Ser Val Pro Ser Glu Ala Glu Arg Leu Arg
                405                 410                 415
Phe Leu Ser Ser Pro Leu Gly Lys Asn Glu Tyr Ser Lys Trp Val Val
            420                 425                 430
Gly Ser Gln Arg Ser Leu Leu Glu Ile Met Ala Glu Phe Pro Ser Ala
        435                 440                 445
Lys Pro Pro Leu Gly Val Phe Phe Ala Ala Val Ala Pro Arg Leu Pro
    450                 455                 460
Pro Arg Tyr Tyr Ser Ile Ser Ser Ser Pro Lys Phe Ala Pro Ser Arg
465                 470                 475                 480
Ile His Val Thr Cys Ala Leu Val Tyr Gly Gln Ser Pro Thr Gly Arg
                485                 490                 495
Val His Arg Gly Val Cys Ser Thr Trp Met Lys His Ala Val Pro Gln
            500                 505                 510
Asp Ser Trp Ala Pro Ile Phe Val Arg Thr Ser Asn Phe Lys Leu Pro
        515                 520                 525
Ala Asp Pro Ser Thr Pro Ile Ile Met Val Gly Pro Gly Thr Gly Leu
    530                 535                 540
Ala Pro Phe Arg Gly Phe Leu Gln Glu Arg Met Ala Leu Lys Glu Asn
545                 550                 555                 560
Gly Ala Gln Leu Gly Pro Ala Val Leu Phe Phe Gly Cys Arg Asn Arg
                565                 570                 575
Asn Met Asp Phe Ile Tyr Glu Asp Glu Leu Asn Asn Phe Val Glu Arg
            580                 585                 590
Gly Val Ile Ser Glu Leu Val Ile Ala Phe Ser Arg Glu Gly Glu Lys
        595                 600                 605
Lys Glu Tyr Val Gln His Lys Met Met Glu Lys Ala Thr Asp Val Trp
    610                 615                 620
Asn Val Ile Ser Gly Asp Gly Tyr Leu Tyr Val Cys Gly Asp Ala Lys
625                 630                 635                 640
Gly Met Ala Arg Asp Val His Arg Thr Leu His Thr Ile Ala Gln Glu
                645                 650                 655
Gln Gly Pro Met Glu Ser Ser Ala Ala Glu Ala Ala Val Lys Lys Leu
            660                 665                 670
Gln Val Glu Glu Arg Tyr Leu Arg Asp Val Trp
        675                 680

<210> SEQ ID NO 18
<211> LENGTH: 2154
<212> TYPE: DNA
<213> ORGANISM: Eschscholzia californica

<400> SEQUENCE: 18
tgcagcccgg gggatccgcc ctatggaaca aactgcggtt aaagtctctt tgtttgatct      60
attttcttcg atacttaatg gaaagttgga tccgtcgaac ttttcttcag attcaagtgc     120
tgctattttg attgaaaatc gtgagatttt aatgatctta caactgcta ttgctgtttt      180
tatcggttgt ggttttctct acgtttggag aagatcttca aataagtcga gtaaaattgt     240
tgaaactcag aaattgatcg ttgaaaagga accagaacct gaagttgatg atggaaagaa     300
gaaggttact atcttctttg gtactcaaac tggtacagct gaaggattcg caaaggcact     360
tgctgaagaa gcaaaagcaa gatatgaaaa ggcaatcttt aaagtgattg atctggatga     420
ttacggagca gatgatgatg aattcgaaga gaaattgaaa aaggaaacta gctctcttt      480
cttttttggct acctatggag atggtgaacc tacagataat gctgcaagat tttataaatg     540
```

-continued

```
gttcacagag ggagagaggg aaatgtggct ccagaatctt caatttggtg tcttcggtct       600
aggcaataga cagtatgagc atttcaataa ggtggcaaag gaggtggacg agatactcac       660
tgaacagggt gggaagcgta ttgttcccgt gggtctagga gatgatgatc aatgcataga       720
agatgatttc actgcgtggc gggagttggt atggcctgaa ttggatcagt tgctccttga       780
tgaaagtgat aaaacatctg tttctactcc ttacactgcc atcgtaccag aatacagggt       840
agtattccat gatgctactg atgcatcact acaagacaaa aactggagca atgcaaatgg       900
ctacactgtt tacgacgttc aacacccatg cagagccaat gtcgttgtaa agaaggagct       960
tcacactcca gtatctgatc gttcttgtat tcatctggaa tttgacattt ctggcactgg      1020
gctcacgtat gaaacaggag accatgtcgg tgtttactct gagaattgtg ttgaagttgt      1080
cgaggaagca gagaggctat tgggttactc atcagacacc gtttttttcaa tccatgtcga    1140 taaagaggac ggctcaccca ttagtggaag cgctctagct cctccttttc caactccctg      1200
cactctaaga acagcactaa cacgatacgc tgatctgttg aattctccca agaaggctgc      1260
tctgcatgct ttggctgctt atgcatccga tccaaaggaa gcggagcgac taaggtatct      1320
tgcgtctcct gctgggaagg acgaatacgc ccagtggata gtagctagtc agagaagtct      1380
gctagtggtc atggctgaat tcccatcagc aaaggctcca attggggttt tctttgcagc      1440
agtagctcct cgcttgctgc caagatacta ttctatttca tcttccaata ggatggtacc      1500
atctaggatt catgtcacat gtgcattggt gcatgaaaaa acaccggcag gtcgggttca      1560
caaaggagtg tgttcaacct ggatgaagaa ttctgtgtct ttggaagaaa accatgattg      1620
cagcagctgg gcaccaatct ttgtcaggca atccaacttc aaacttcctg ctgattctac      1680
agtaccaatt ataatgattg gtcctgggac tggattagct ccctttaggg gattcatgca      1740
ggagcgatta gctctgaaga attctggtgt agaattggga cccgctatcc tcttctttgg      1800
atgcagaaac agacagatgg attacatata tgaagaggag ctaaacaact ttgtgaaaga      1860
gggagctatc tccgaagttg ttgttgctttt ctcacgtgag ggagctacca aggaatacgt      1920
acaacataaa atggcggaga aggcttccta catctgggaa atgatctctc aaggtgctta      1980
tctttatgta tgtggtgatg ccaagggcat ggctagagac gtacatcgaa ctctccacac      2040
cattgcccag gaacagggat cttttggaca ctcgaagacc gaaagcttgg tgaagaatct      2100
acagatggat ggaaggtatc tacgtgatgt gtggtgattg gggctagagc ggcc            2154
```

<210> SEQ ID NO 19
<211> LENGTH: 704
<212> TYPE: PRT
<213> ORGANISM: Eschscholzia californica

<400> SEQUENCE: 19

```
Met Glu Gln Thr Ala Val Lys Val Ser Leu Phe Asp Leu Phe Ser Ser
1               5                   10                  15

Ile Leu Asn Gly Lys Leu Asp Pro Ser Asn Phe Ser Ser Asp Ser Ser
            20                  25                  30

Ala Ala Ile Leu Ile Glu Asn Arg Glu Ile Leu Met Ile Leu Thr Thr
        35                  40                  45

Ala Ile Ala Val Phe Ile Gly Cys Gly Phe Leu Tyr Val Trp Arg Arg
    50                  55                  60

Ser Ser Asn Lys Ser Ser Lys Ile Val Glu Thr Gln Lys Leu Ile Val
65                  70                  75                  80

Glu Lys Glu Pro Glu Pro Glu Val Asp Asp Gly Lys Lys Lys Val Thr
```

```
            85                  90                  95
Ile Phe Phe Gly Thr Gln Thr Gly Thr Ala Glu Gly Phe Ala Lys Ala
            100                 105                 110

Leu Ala Glu Glu Ala Lys Ala Arg Tyr Glu Lys Ala Ile Phe Lys Val
            115                 120                 125

Ile Asp Leu Asp Asp Tyr Gly Ala Asp Asp Glu Phe Glu Glu Lys
            130                 135                 140

Leu Lys Lys Glu Thr Ile Ala Leu Phe Phe Leu Ala Thr Tyr Gly Asp
145                 150                 155                 160

Gly Glu Pro Thr Asp Asn Ala Ala Arg Phe Tyr Lys Trp Phe Thr Glu
                    165                 170                 175

Gly Glu Arg Glu Met Trp Leu Gln Asn Leu Gln Phe Gly Val Phe Gly
                    180                 185                 190

Leu Gly Asn Arg Gln Tyr Glu His Phe Asn Lys Val Ala Lys Glu Val
                    195                 200                 205

Asp Glu Ile Leu Thr Glu Gln Gly Gly Lys Arg Ile Val Pro Val Gly
                    210                 215                 220

Leu Gly Asp Asp Asp Gln Cys Ile Glu Asp Asp Phe Thr Ala Trp Arg
225                 230                 235                 240

Glu Leu Val Trp Pro Glu Leu Asp Gln Leu Leu Leu Asp Glu Ser Asp
                    245                 250                 255

Lys Thr Ser Val Ser Thr Pro Tyr Thr Ala Ile Val Pro Glu Tyr Arg
                    260                 265                 270

Val Val Phe His Asp Ala Thr Asp Ala Ser Leu Gln Asp Lys Asn Trp
                    275                 280                 285

Ser Asn Ala Asn Gly Tyr Thr Val Tyr Asp Val Gln His Pro Cys Arg
290                 295                 300

Ala Asn Val Val Lys Lys Glu Leu His Thr Pro Val Ser Asp Arg
305                 310                 315                 320

Ser Cys Ile His Leu Glu Phe Asp Ile Ser Gly Thr Gly Leu Thr Tyr
                    325                 330                 335

Glu Thr Gly Asp His Val Gly Val Tyr Ser Glu Asn Cys Val Glu Val
                    340                 345                 350

Val Glu Glu Ala Glu Arg Leu Leu Gly Tyr Ser Ser Asp Thr Val Phe
                    355                 360                 365

Ser Ile His Val Asp Lys Glu Asp Gly Ser Pro Ile Ser Gly Ser Ala
                    370                 375                 380

Leu Ala Pro Pro Phe Pro Thr Pro Cys Thr Leu Arg Thr Ala Leu Thr
385                 390                 395                 400

Arg Tyr Ala Asp Leu Leu Asn Ser Pro Lys Lys Ala Ala Leu His Ala
                    405                 410                 415

Leu Ala Ala Tyr Ala Ser Asp Pro Lys Glu Ala Glu Arg Leu Arg Tyr
                    420                 425                 430

Leu Ala Ser Pro Ala Gly Lys Asp Glu Tyr Ala Gln Trp Ile Val Ala
                    435                 440                 445

Ser Gln Arg Ser Leu Leu Val Val Met Ala Glu Phe Pro Ser Ala Lys
                    450                 455                 460

Ala Pro Ile Gly Val Phe Phe Ala Ala Val Ala Pro Arg Leu Leu Pro
465                 470                 475                 480

Arg Tyr Tyr Ser Ile Ser Ser Ser Asn Arg Met Val Pro Ser Arg Ile
                    485                 490                 495

His Val Thr Cys Ala Leu Val His Glu Lys Thr Pro Ala Gly Arg Val
                    500                 505                 510
```

-continued

```
His Lys Gly Val Cys Ser Thr Trp Met Lys Asn Ser Val Ser Leu Glu
            515                 520                 525

Glu Asn His Asp Cys Ser Ser Trp Ala Pro Ile Phe Val Arg Gln Ser
        530                 535                 540

Asn Phe Lys Leu Pro Ala Asp Ser Thr Val Pro Ile Ile Met Ile Gly
545                 550                 555                 560

Pro Gly Thr Gly Leu Ala Pro Phe Arg Gly Phe Met Gln Glu Arg Leu
                565                 570                 575

Ala Leu Lys Asn Ser Gly Val Glu Leu Gly Pro Ala Ile Leu Phe Phe
            580                 585                 590

Gly Cys Arg Asn Arg Gln Met Asp Tyr Ile Tyr Glu Glu Leu Asn
        595                 600                 605

Asn Phe Val Lys Glu Gly Ala Ile Ser Glu Val Val Ala Phe Ser
        610                 615                 620

Arg Glu Gly Ala Thr Lys Glu Tyr Val Gln His Lys Met Ala Glu Lys
625                 630                 635                 640

Ala Ser Tyr Ile Trp Glu Met Ile Ser Gln Gly Ala Tyr Leu Tyr Val
                645                 650                 655

Cys Gly Asp Ala Lys Gly Met Ala Arg Asp Val His Arg Thr Leu His
                660                 665                 670

Thr Ile Ala Gln Glu Gln Gly Ser Leu Asp Asn Ser Lys Thr Glu Ser
            675                 680                 685

Leu Val Lys Asn Leu Gln Met Asp Gly Arg Tyr Leu Arg Asp Val Trp
690                 695                 700
```

<210> SEQ ID NO 20
<211> LENGTH: 149
<212> TYPE: PRT
<213> ORGANISM: Arabidopsis thaliana

<400> SEQUENCE: 20

```
Gly Ser Pro Leu Glu Ser Ala Val Pro Pro Phe Pro Gly Pro Cys
1               5                   10                  15

Thr Leu Gly Thr Gly Leu Ala Arg Tyr Ala Asp Leu Leu Asn Pro Pro
                20                  25                  30

Arg Lys Ser Ala Leu Val Ala Leu Ala Ala Tyr Ala Thr Glu Pro Ser
            35                  40                  45

Glu Ala Glu Lys Leu Lys His Leu Thr Ser Pro Asp Gly Lys Asp Glu
        50                  55                  60

Tyr Ser Gln Trp Ile Val Ala Ser Gln Arg Ser Leu Leu Glu Val Met
65                  70                  75                  80

Ala Ala Phe Pro Ser Ala Lys Pro Pro Leu Gly Val Phe Phe Ala Ala
                85                  90                  95

Ile Ala Pro Arg Leu Gln Pro Arg Tyr Tyr Ser Ile Ser Ser Cys Gln
                100                 105                 110

Asp Trp Ala Pro Ser Arg Val His Val Thr Ser Ala Leu Val Tyr Gly
            115                 120                 125

Pro Thr Pro Thr Gly Arg Ile His Lys Gly Val Cys Ser Thr Trp Met
        130                 135                 140

Lys Asn Ala Val Pro
145
```

<210> SEQ ID NO 21
<211> LENGTH: 149
<212> TYPE: PRT

<213> ORGANISM: Catharanthus roseus

<400> SEQUENCE: 21

```
Gly Thr Pro Leu Ala Gly Ser Ser Leu Pro Pro Phe Pro Pro Cys
1               5                   10                  15

Thr Leu Arg Thr Ala Leu Thr Arg Trp Ala Asp Leu Leu Asn Thr Pro
            20                  25                  30

Lys Lys Ser Ala Leu Leu Ala Leu Ala Ala Tyr Ala Ser Asp Pro Asn
            35                  40                  45

Glu Ala Asp Arg Leu Lys Tyr Leu Ala Ser Pro Ala Gly Lys Asp Glu
        50                  55                  60

Tyr Ala Gln Ser Leu Val Ala Asn Gln Arg Ser Leu Leu Glu Val Met
65                  70                  75                  80

Ala Glu Phe Pro Ser Ala Lys Pro Pro Leu Gly Val Phe Phe Ala Ala
                85                  90                  95

Ile Ala Pro Arg Leu Gln Pro Arg Phe Tyr Ser Ile Ser Ser Ser Pro
                100                 105                 110

Arg Met Ala Pro Ser Arg Ile His Val Thr Cys Ala Leu Val Tyr Glu
            115                 120                 125

Lys Thr Pro Gly Gly Arg Ile His Lys Gly Val Cys Ser Thr Trp Met
        130                 135                 140

Lys Asn Ala Ile Pro
145
```

<210> SEQ ID NO 22
<211> LENGTH: 149
<212> TYPE: PRT
<213> ORGANISM: Helianthus tuberosus

<400> SEQUENCE: 22

```
Gly Thr Pro Leu Gly Gly Pro Thr Leu Gln Pro Pro Phe Pro Pro Cys
1               5                   10                  15

Thr Leu Arg Lys Ala Leu Thr Asn Tyr Ala Asp Leu Leu Ser Ser Pro
            20                  25                  30

Lys Lys Ser Thr Leu Leu Ala Leu Ala Ala His Ala Ser Asp Ala Thr
            35                  40                  45

Glu Ala Asp Arg Leu Gln Phe Leu Ala Ser Arg Glu Gly Lys Asp Glu
        50                  55                  60

Tyr Ala Glu Trp Ile Val Ala Asn Gln Arg Ser Leu Leu Glu Val Met
65                  70                  75                  80

Glu Ala Phe Pro Ser Ala Lys Pro Pro Leu Gly Val Phe Phe Ala Ala
                85                  90                  95

Ile Ala Pro Arg Leu Gln Pro Arg Tyr Tyr Ser Ile Ser Ser Ser Pro
                100                 105                 110

Lys Met Val Pro Asn Arg Ile His Val Thr Cys Ala Leu Val Tyr Glu
            115                 120                 125

Lys Thr Pro Gly Gly Arg Ile His Lys Gly Ile Cys Ser Thr Trp Met
        130                 135                 140

Lys Asn Ala Val Pro
145
```

<210> SEQ ID NO 23
<211> LENGTH: 149
<212> TYPE: PRT
<213> ORGANISM: Vigna radiata

<400> SEQUENCE: 23

```
Gly Thr Pro Leu Gly Gly Pro Thr Leu Gln Pro Pro Phe Pro Pro Cys
1               5                   10                  15

Thr Leu Arg Lys Ala Leu Thr Asn Tyr Ala Asp Leu Leu Ser Ser Pro
            20                  25                  30

Lys Lys Ser Thr Leu Leu Ala Leu Ala Ala His Ala Ser Asp Ala Thr
        35                  40                  45

Glu Ala Asp Arg Leu Gln Phe Leu Ala Ser Arg Glu Gly Lys Asp Glu
    50                  55                  60

Tyr Ala Glu Trp Ile Val Ala Asn Gln Arg Ser Leu Leu Glu Val Met
65                  70                  75                  80

Glu Ala Phe Pro Ser Ala Lys Pro Pro Leu Gly Val Phe Phe Ala Ala
                85                  90                  95

Ile Ala Pro Arg Leu Gln Pro Arg Tyr Tyr Ser Ile Ser Ser Ser Pro
                100                 105                 110

Lys Met Val Pro Asn Arg Ile His Val Thr Cys Ala Leu Val Tyr Glu
            115                 120                 125

Lys Thr Pro Gly Gly Arg Ile His Lys Gly Ile Cys Ser Thr Trp Met
        130                 135                 140

Lys Asn Ala Val Pro
145

<210> SEQ ID NO 24
<211> LENGTH: 149
<212> TYPE: PRT
<213> ORGANISM: Vicia sativa

<400> SEQUENCE: 24

Gly Thr Ser Leu Gly Gly Ser Leu Leu Pro Pro Phe Pro Gly Pro Cys
1               5                   10                  15

Thr Val Arg Thr Ala Leu Ala Cys Tyr Ala Asp Leu Leu Asn Pro Pro
            20                  25                  30

Arg Lys Ala Ala Ile Val Ala Leu Ala Ala His Ala Ser Glu Pro Ser
        35                  40                  45

Glu Ala Glu Arg Leu Lys Phe Leu Ser Ser Pro Gln Gly Lys Asp Glu
    50                  55                  60

Tyr Ser Lys Trp Val Val Gly Ser Gln Arg Ser Leu Leu Glu Val Met
65                  70                  75                  80

Ala Asp Phe Pro Ser Ala Lys Pro Pro Leu Gly Val Phe Phe Ala Ala
                85                  90                  95

Ile Ala Pro Arg Leu Gln Pro Arg Tyr Tyr Ser Ile Ser Ser Ser Pro
                100                 105                 110

Arg Pro Ala Pro Gln Arg Val His Val Thr Cys Ala Leu Val Glu Gly
            115                 120                 125

Pro Thr Pro Thr Gly Arg Ile His Lys Gly Val Cys Ser Thr Trp Met
        130                 135                 140

Lys Ser Ala Thr Pro
145

<210> SEQ ID NO 25
<211> LENGTH: 706
<212> TYPE: PRT
<213> ORGANISM: Eschscholzia californica

<400> SEQUENCE: 25

Met Glu Gln Thr Ala Val Lys Val Ser Leu Phe Asp Leu Phe Ser Ser
1               5                   10                  15
```

```
Ile Leu Asn Gly Lys Leu Asp Pro Ser Asn Phe Ser Ser Asp Ser Ser
            20                  25                  30

Ala Ala Ile Leu Ile Glu Asn Arg Glu Ile Leu Met Ile Leu Thr Thr
            35                  40                  45

Ala Ile Ala Val Phe Ile Gly Cys Gly Phe Leu Tyr Val Trp Arg Arg
        50                  55                  60

Ser Ser Asn Lys Ser Ser Lys Ile Val Glu Thr Gln Lys Leu Ile Val
65                  70                  75                  80

Glu Lys Glu Pro Glu Pro Glu Val Asp Asp Gly Lys Lys Val Thr
                85                  90                  95

Ile Phe Phe Gly Thr Gln Thr Gly Thr Ala Glu Gly Phe Ala Lys Ala
                100                 105                 110

Leu Ala Glu Glu Ala Lys Ala Arg Tyr Glu Lys Ala Ile Phe Lys Val
            115                 120                 125

Ile Asp Leu Asp Asp Tyr Gly Ala Val Asp Asp Glu Phe Glu Glu Lys
130                 135                 140

Leu Lys Lys Glu Thr Ile Ala Leu Phe Phe Leu Ala Thr Tyr Gly Asp
145                 150                 155                 160

Gly Glu Pro Thr Asp Asn Ala Ala Arg Phe Tyr Lys Trp Phe Thr Glu
                165                 170                 175

Gly Lys Glu Arg Glu Met Trp Leu Gln Asn Leu Gln Phe Gly Val Phe
            180                 185                 190

Gly Leu Gly Asn Arg Gln Tyr Glu His Phe Asn Lys Val Ala Lys Glu
        195                 200                 205

Val Asp Glu Ile Leu Thr Glu Gln Gly Gly Lys Arg Ile Val Pro Val
    210                 215                 220

Gly Leu Gly Asp Asp Asp Gln Cys Ile Glu Asp Asp Phe Thr Ala Trp
225                 230                 235                 240

Arg Glu Leu Val Trp Pro Glu Leu Asp Gln Leu Leu Leu Asp Glu Ser
                245                 250                 255

Asp Lys Gln Ser Val Ser Thr Pro Tyr Thr Ala Ile Val Pro Glu Tyr
            260                 265                 270

Arg Val Val Phe His Asp Ala Thr Asp Ala Ser Leu Gln Asp Lys Asn
        275                 280                 285

Trp Ser Asn Ala Asn Gly Tyr Thr Val Tyr Asp Val Gln His Pro Cys
290                 295                 300

Arg Ala Asn Val Val Lys Lys Glu Leu His Thr Pro Val Ser Asp
305                 310                 315                 320

Arg Ser Cys Ile His Leu Glu Phe Asp Ile Ser Gly Thr Gly Leu Thr
                325                 330                 335

Tyr Glu Thr Gly Asp His Val Gly Val Tyr Ser Glu Asn Cys Val Glu
            340                 345                 350

Val Val Glu Glu Ala Glu Arg Leu Leu Gly Tyr Ser Ser Asp Thr Val
        355                 360                 365

Phe Ser Ile His Val Asp Lys Glu Asp Gly Ser Pro Ile Ser Gly Ser
370                 375                 380

Ala Leu Ala Pro Pro Phe Pro Thr Pro Cys Thr Leu Arg Thr Ala Leu
385                 390                 395                 400

Thr Arg Tyr Ala Asp Leu Leu Asn Ser Pro Lys Lys Ala Ala Leu His
            405                 410                 415

Ala Leu Ala Ala Tyr Ala Ser Asp Pro Lys Glu Ala Glu Arg Leu Arg
        420                 425                 430
```

-continued

```
Tyr Leu Ala Ser Pro Ala Gly Lys Asp Glu Tyr Ala Gln Trp Ile Val
            435                 440                 445

Ala Ser Gln Arg Ser Leu Leu Val Val Met Ala Glu Phe Pro Ser Ala
        450                 455                 460

Lys Ala Pro Ile Gly Val Phe Ala Ala Val Ala Pro Arg Leu Leu
465                 470                 475                 480

Pro Arg Tyr Tyr Ser Ile Ser Ser Asn Arg Met Val Pro Ser Arg
                    485                 490                 495

Ile His Val Thr Cys Ala Leu Val His Glu Lys Thr Pro Ala Gly Arg
                500                 505                 510

Val His Lys Gly Val Val Cys Ser Thr Trp Met Lys Asn Ser Val Ser
            515                 520                 525

Leu Glu Glu Asn His Asp Cys Ser Ser Trp Ala Pro Ile Phe Val Arg
        530                 535                 540

Gln Ser Asn Phe Lys Leu Pro Ala Asp Ser Thr Val Pro Ile Ile Met
545                 550                 555                 560

Ile Gly Pro Gly Thr Gly Leu Ala Pro Phe Arg Gly Phe Met Gln Glu
                565                 570                 575

Arg Leu Ala Leu Lys Asn Ser Val Glu Leu Gly Pro Ala Ile Leu
                    580                 585                 590

Phe Phe Gly Cys Arg Asn Arg Gln Met Asp Tyr Ile Tyr Glu Glu Glu
            595                 600                 605

Leu Asn Asn Phe Val Lys Glu Gly Ala Ile Ser Glu Val Val Ala
        610                 615                 620

Phe Ser Arg Glu Gly Ala Thr Lys Glu Tyr Val Gln His Lys Met Ala
625                 630                 635                 640

Glu Lys Ala Ser Tyr Ile Trp Glu Met Ile Ser Gln Gly Ala Tyr Leu
                645                 650                 655

Tyr Val Cys Gly Asp Ala Lys Gly Met Ala Arg Asp Val His Arg Thr
                    660                 665                 670

Leu His Thr Ile Ala Gln Glu Gln Gly Ser Leu Asp Asn Ser Lys Thr
            675                 680                 685

Glu Ser Leu Val Lys Asn Leu Gln Met Asp Gly Arg Tyr Leu Arg Asp
        690                 695                 700

Val Trp
705
```

<210> SEQ ID NO 26
<211> LENGTH: 682
<212> TYPE: PRT
<213> ORGANISM: Papaver somniferum

<400> SEQUENCE: 26

```
Met Gly Ser Asn Asn Leu Ala Asn Ser Ile Glu Ser Met Leu Gly Ile
1               5                   10                  15

Ser Ile Gly Ser Glu Tyr Ile Ser Asp Pro Ile Phe Ile Met Val Thr
            20                  25                  30

Thr Val Ala Ser Met Leu Ile Gly Phe Gly Phe Phe Val Cys Met Lys
        35                  40                  45

Ser Ser Ser Ser Gln Ser Lys Pro Ile Glu Thr Tyr Lys Pro Ile Ile
    50                  55                  60

Asp Lys Glu Glu Glu Glu Ile Glu Val Asp Pro Gly Lys Ile Lys Leu
65                  70                  75                  80

Thr Ile Phe Phe Gly Thr Gln Thr Gly Thr Ala Glu Gly Phe Ala Lys
                85                  90                  95
```

-continued

```
Ala Leu Ala Glu Glu Ile Lys Ala Lys Tyr Lys Lys Ala Val Val Lys
            100                 105                 110
Val Val Asp Leu Asp Asp Tyr Ala Ala Glu Asp Gln Tyr Glu Glu
        115                 120                 125
Lys Leu Lys Lys Glu Ser Leu Val Phe Phe Met Val Ala Thr Tyr Gly
130                 135                 140
Asp Gly Glu Pro Thr Asp Asn Ala Ala Arg Phe Tyr Lys Trp Phe Thr
145                 150                 155                 160
Gln Glu His Glu Arg Gly Glu Trp Leu Gln Gln Leu Thr Tyr Gly Val
                165                 170                 175
Phe Gly Leu Gly Asn Arg Gln Tyr Glu His Phe Asn Lys Ile Ala Val
                180                 185                 190
Asp Val Asp Glu Gln Leu Gly Lys Gln Gly Ala Lys Arg Ile Val Gln
            195                 200                 205
Val Gly Leu Gly Asp Asp Asp Gln Cys Ile Glu Asp Asp Phe Thr Ala
        210                 215                 220
Trp Arg Glu Leu Leu Trp Thr Glu Leu Asp Gln Leu Leu Lys Asp Glu
225                 230                 235                 240
Asp Ala Ala Pro Ser Val Ala Thr Pro Tyr Ala Ile Thr Val Pro Glu
                245                 250                 255
Tyr Arg Val Val Ile His Glu Thr Thr Val Ala Ala Leu Asp Asp Lys
                260                 265                 270
His Ile Asn Thr Ala Asn Gly Asp Val Ala Phe Asp Ile Leu His Pro
            275                 280                 285
Cys Arg Thr Ile Val Ala Gln Gln Arg Glu Leu His Lys Pro Lys Ser
        290                 295                 300
Asp Arg Asp Cys Ile His Leu Glu Phe Asp Ile Ser Gly Ser Ser Leu
305                 310                 315                 320
Thr Tyr Glu Thr Gly Asp His Val Gly Val Tyr Ala Glu Asn Cys Asp
                325                 330                 335
Glu Thr Val Glu Glu Ala Gly Lys Leu Leu Gly Gln Pro Leu Asp Leu
            340                 345                 350
Leu Phe Ser Ile His Thr Asp Lys Glu Asp Gly Ser Pro Gln Gly Ser
        355                 360                 365
Ser Leu Pro Pro Phe Pro Gly Pro Cys Thr Leu Arg Ser Ala Leu Ala
370                 375                 380
Arg Tyr Ala Asp Leu Leu Asn Pro Pro Arg Lys Ala Ser Leu Ile Ala
385                 390                 395                 400
Leu Ser Ala His Ala Ser Val Pro Ser Glu Ala Glu Arg Leu Arg Phe
                405                 410                 415
Leu Ser Ser Pro Leu Gly Lys Asn Glu Tyr Ser Lys Trp Val Val Gly
            420                 425                 430
Ser Gln Arg Ser Leu Leu Glu Ile Met Ala Glu Phe Pro Ser Ala Lys
        435                 440                 445
Pro Pro Leu Gly Val Phe Phe Ala Ala Val Ala Pro Arg Leu Pro Pro
450                 455                 460
Arg Tyr Tyr Ser Ile Ser Ser Ser Pro Lys Phe Ala Pro Ser Arg Ile
465                 470                 475                 480
His Val Thr Cys Ala Leu Val Tyr Gly Gln Ser Pro Thr Gly Arg Phe
                485                 490                 495
His Arg Gly Val Cys Ser Thr Trp Met Lys His Ala Val Pro Gln Asp
            500                 505                 510
```

-continued

Ser Trp Ala Pro Ile Phe Val Arg Thr Ser Asn Phe Lys Leu Pro Ala
        515                 520                 525

Asp Pro Ser Thr Pro Ile Ile Met Val Gly Pro Gly Thr Gly Leu Ala
530                 535                 540

Pro Phe Arg Gly Phe Leu Gln Glu Arg Met Ala Leu Lys Glu Asn Gly
545                 550                 555                 560

Ala Gln Leu Gly Pro Ala Val Leu Phe Phe Gly Cys Arg Asn Arg Asn
                565                 570                 575

Met Asp Phe Ile Tyr Glu Asp Glu Leu Asn Asn Phe Val Glu Arg Gly
                580                 585                 590

Val Ile Ser Glu Leu Val Ile Ala Phe Ser Arg Glu Gly Glu Lys Lys
            595                 600                 605

Glu Tyr Val Gln His Lys Met Met Glu Lys Ala Pro Asp Val Trp Asn
        610                 615                 620

Val Ile Ser Gly Asp Gly Tyr Leu Tyr Val Cys Gly Asp Ala Lys Gly
625                 630                 635                 640

Met Ala Arg Asp Val His Arg Thr Leu His Thr Ile Ala Gln Glu Gln
                645                 650                 655

Gly Ser Met Glu Ser Ser Ala Ala Glu Ala Ala Val Lys Lys Leu Gln
                660                 665                 670

Val Glu Glu Arg Tyr Leu Arg Asp Val Trp
            675                 680

<210> SEQ ID NO 27
<211> LENGTH: 19
<212> TYPE: DNA
<213> ORGANISM: Artificial Sequence
<220> FEATURE:
<223> OTHER INFORMATION: PCR primer
<221> NAME/KEY: misc_feature
<222> LOCATION: (3)..(3)
<223> OTHER INFORMATION: n = Inosine
<221> NAME/KEY: misc_feature
<222> LOCATION: (5)..(5)
<223> OTHER INFORMATION: n = Inosine
<221> NAME/KEY: misc_feature
<222> LOCATION: (7)..(7)
<223> OTHER INFORMATION: n = Inosine
<221> NAME/KEY: misc_feature
<222> LOCATION: (8)..(8)
<223> OTHER INFORMATION: n = Inosine

<400> SEQUENCE: 27
cantncnncc tcctttccc                                              19

<210> SEQ ID NO 28
<211> LENGTH: 19
<212> TYPE: DNA
<213> ORGANISM: Artificial Sequence
<220> FEATURE:
<223> OTHER INFORMATION: PCR primer
<221> NAME/KEY: misc_feature
<222> LOCATION: (3)..(3)
<223> OTHER INFORMATION: n = Inosine
<221> NAME/KEY: misc_feature
<222> LOCATION: (5)..(5)
<223> OTHER INFORMATION: n = Inosine
<221> NAME/KEY: misc_feature
<222> LOCATION: (7)..(7)
<223> OTHER INFORMATION: n = Inosine
<221> NAME/KEY: misc_feature
<222> LOCATION: (8)..(8)
<223> OTHER INFORMATION: n = Inosine

<400> SEQUENCE: 28
ctntncnncc tcctttccc                                                19

<210> SEQ ID NO 29
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (15)..(15)
<223> OTHER INFORMATION: n=Inosine

<400> SEQUENCE: 29
acctacttct tacgncaagg                                               20

<210> SEQ ID NO 30
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (15)..(15)
<223> OTHER INFORMATION: n = Inosine

<400> SEQUENCE: 30
acctacttct cacgntgcgg                                               20

<210> SEQ ID NO 31
<211> LENGTH: 29
<212> TYPE: DNA
<213> ORGANISM: Artificial Sequence
<220> FEATURE:
<223> OTHER INFORMATION: PCR primer
<221> NAME/KEY: misc_feature
<222> LOCATION: (6)..(6)
<223> OTHER INFORMATION: n = Inosine
<221> NAME/KEY: misc_feature
<222> LOCATION: (9)..(9)
<223> OTHER INFORMATION: n = Inosine
<221> NAME/KEY: misc_feature
<222> LOCATION: (12)..(12)
<223> OTHER INFORMATION: n = Inosine
<221> NAME/KEY: misc_feature
<222> LOCATION: (15)..(15)
<223> OTHER INFORMATION: n = Inosine
<221> NAME/KEY: misc_feature
<222> LOCATION: (18)..(18)
<223> OTHER INFORMATION: n = Inosine
<221> NAME/KEY: misc_feature
<222> LOCATION: (21)..(21)
<223> OTHER INFORMATION: n = Inosine
<221> NAME/KEY: misc_feature
<222> LOCATION: (22)..(22)
<223> OTHER INFORMATION: n = Inosine
<221> NAME/KEY: misc_feature
<222> LOCATION: (24)..(24)
<223> OTHER INFORMATION: n = Inosine

<400> SEQUENCE: 31
aaacgncgnt ancgnggnsc nngngttgg                                     29

<210> SEQ ID NO 32
<211> LENGTH: 29
<212> TYPE: DNA
<213> ORGANISM: Artificial Sequence
<220> FEATURE:
<223> OTHER INFORMATION: PCR primer
<221> NAME/KEY: misc_feature
<222> LOCATION: (6)..(6)
<223> OTHER INFORMATION: n = Inosine
<221> NAME/KEY: misc_feature

```
<222> LOCATION: (9)..(9)
<223> OTHER INFORMATION: n = Inosine
<221> NAME/KEY: misc_feature
<222> LOCATION: (12)..(12)
<223> OTHER INFORMATION: n = Inosine
<221> NAME/KEY: misc_feature
<222> LOCATION: (15)..(15)
<223> OTHER INFORMATION: n = Inosine
<221> NAME/KEY: misc_feature
<222> LOCATION: (18)..(18)
<223> OTHER INFORMATION: n = Inosine
<221> NAME/KEY: misc_feature
<222> LOCATION: (21)..(21)
<223> OTHER INFORMATION: n = Inosine
<221> NAME/KEY: misc_feature
<222> LOCATION: (22)..(22)
<223> OTHER INFORMATION: n = Inosine
<221> NAME/KEY: misc_feature
<222> LOCATION: (24)..(24)
<223> OTHER INFORMATION: n = Inosine

<400> SEQUENCE: 32
aagcgncgnt ancgnggnsc nngngtcgg                                    29
```